US012560600B2

(12) United States Patent
Butler et al.

(10) Patent No.: US 12,560,600 B2
(45) Date of Patent: Feb. 24, 2026

(54) RAPID AND SENSITIVE DETECTION OF VIRAL PARTICLES BY COUPLING REDOX CYCLING AND ELECTROPHORETIC ENRICHMENT

(71) Applicant: The Penn State Research Foundation, University Park, PA (US)

(72) Inventors: Derrick James Butler, State College, PA (US); Aida Ebrahimi, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 18/836,599

(22) PCT Filed: Feb. 7, 2023

(86) PCT No.: PCT/US2023/062093
§ 371 (c)(1),
(2) Date: Aug. 7, 2024

(87) PCT Pub. No.: WO2023/177943
PCT Pub. Date: Sep. 21, 2023

(65) Prior Publication Data
US 2025/0147018 A1    May 8, 2025

Related U.S. Application Data

(60) Provisional application No. 63/320,856, filed on Mar. 17, 2022.

(51) Int. Cl.
*G01N 33/543* (2006.01)
*G01N 27/327* (2006.01)
*G01N 33/569* (2006.01)

(52) U.S. Cl.
CPC ..... *G01N 33/5438* (2013.01); *G01N 27/3277* (2013.01); *G01N 33/56983* (2013.01); *G01N 2333/005* (2013.01)

(58) Field of Classification Search
CPC ......... G01N 33/5438; G01N 33/56983; G01N 27/3277
See application file for complete search history.

(56) References Cited

U.S. PATENT DOCUMENTS

| | | | | |
|---|---|---|---|---|
| 2009/0092965 A1* | 4/2009 | Weiss | ................... | G01N 27/327 |
| | | | | 435/5 |
| 2009/0293590 A1* | 12/2009 | Zeng | .................... | G01N 29/022 |
| | | | | 73/24.06 |
| 2021/0123883 A1 | 4/2021 | Tabib-Azar | | |

FOREIGN PATENT DOCUMENTS

| | | | | |
|---|---|---|---|---|
| WO | 2015160085 A1 | 10/2015 | | |
| WO | WO-2019200021 A1 * | 10/2019 | ........... | C12N 5/0619 |
| WO | 2022049540 A1 | 3/2022 | | |

OTHER PUBLICATIONS

M. Morita, Enhancement of Redox Cycling Currents at Interdigitated Electrodes with Elevated Fingers, Electrochem. Soc. 2014, 161 , p. H178-82. (Year: 2014).*

(Continued)

*Primary Examiner* — C. Sun
(74) *Attorney, Agent, or Firm* — Buchanan Ingersoll & Rooney PC

(57)        ABSTRACT

Embodiments relate to a biosensor. The biosensor includes an electrochemical system having a generator electrode, a collector electrode, and electrolyte. The generator electrode includes a particle capture region having an aspect ratio that is greater than 1. The particle capture region is a portion of the generator electrode configured to attract a particle supported within the electrolyte. The electrochemical system is operated so as to bias one of the generator electrode or the (Continued)

collector electrode below its formal potential while biasing the other electrode above its formal potential. The biosensor includes a processing module configured to measure electric current generated by the electrochemical system.

8 Claims, 56 Drawing Sheets

(56)                References Cited

OTHER PUBLICATIONS

Butler, D. et al., Rapid and sensitive detection of viral particles by coupling redox cycling and electrophoretic enrichment, Biosensors and Bioelectronics 208, 2022, 1-9, Elsevier B.V.

Lee, G. et al., Chronoamperometry-Based Redox Cycling for Application to Immunoassays, ACS Sens., 2018, 3, 106-112, American Chemical Society.

Yamamoto, S. et al., Redox Cycling Realized in Paper-Based Biochemical Sensor for Selective Detection of Reversible Redox MoleculesWithout Micro/Nano Fabrication Process, Sensors, 2018, 18, 730, 1-13.

International Search Report and Written Opinion for PCT/US2023/062093 filed Feb. 7, 2023, dated Jun. 28, 2023.

* cited by examiner

RAPID AND SENSITIVE DETECTION OF VIRAL PARTICLES BY COUPLING REDOX CYCLING AND ELECTROPHORETIC ENRICHMENT

CROSS-REFERENCE TO RELATED APPLICATIONS

This patent application is a U.S. national stage application under 35 U.S.C. § 371 for International Patent Application No. PCT/US2023/062093, filed on Feb. 7, 2023, which is related to and claims the benefit of U.S. provisional patent application 63/320,856, filed on Mar. 17, 2022, the entire contents of each is incorporated by reference.

STATEMENT REGARDING FEDERALLY SPONSORED RESEARCH OR DEVELOPMENT

This invention was made with government support under Grant Nos. EB031354 and GM132793 awarded by the National Institutes of Health. The Government has certain rights in the invention

FIELD OF THE INVENTION

Embodiments relate to a biosensing system that operates electrodes having specific geometries within a redox cycling electrochemical environment in a biased manner to perform a quench current so as to provide an improved sensing mechanism.

BACKGROUND OF THE INVENTION

Prompt and accurate detection of viruses is critical for upholding public safety and minimizing widespread outbreaks of infectious diseases. This is especially relevant in the backdrop of the current COVID-19 pandemic—caused by Severe Acute Respiratory Syndrome Coronavirus 2 (SARS-CoV-2) —which is responsible for more than 428 million infections and 5.9 million deaths globally at the time of writing. Although the COVID-19 pandemic has been the most widespread in recent history, outbreaks caused by other viruses, such as influenza, Dengue, human immunodeficiency virus (HIV), and Ebola place additional stress on the global healthcare system. Widespread testing is a cornerstone of the effort to mitigate the devastating impact of present and future pandemics. Simple-to-use, sensitive, and rapid diagnostics that can be manufactured at relatively low cost and at a large scale are critical to better monitor the spread of infection and minimize the burden on healthcare systems.

Current strategies for detecting viral infections include polymerase chain reaction (PCR), reverse transcription polymerase chain reaction (RT-PCR), enzyme linked immunosorbent assays (ELISA), isothermal amplification, and immunochromatography, among others. While effective, many of these techniques require significant overhead and have limited operational capacity outside of clinical settings. Therefore, electrochemical sensors are being increasingly used for virus detection, especially in point-of-need (PON) applications that require prompt results, minimal sample preparation, and simple-to-use equipment. The operating principle typically relies on changes in the current or impedance of a redox probe as virus particles attach to the electrode surface. To increase the appeal of electrochemical sensors for PON applications, electrode miniaturization is actively being pursued to further reduce sample volume requirements, improve spatial resolution, especially in sensor arrays, and explore previously inaccessible regions, such as the interior of individual cells. However, due to the reduced capture area of miniaturized electrochemical sensors, the likelihood of a virion diffusing to the sensor is reduced. In an effort to improve the sensitivity, redox cycling can be employed.

Redox cycling leverages two independently biased working electrodes spaced in close proximity to one another. One electrode is biased above the formal potential ($E^0$) of the redox probe while the other is biased below, allowing the oxidized and reduced species to cycle between the electrodes. This recycling amplifies the current and can lead to increased signal-to-noise ratios. As a result, redox cycling has been applied for the detection of a variety of analytes, including dopamine, catechol, ferri/ferrocyanide ($[Fe(CN)_6]^{3-/4-}$), paracetamol, nitrate/nitrite, and clozapine with amplification factors ranging from 1-2 to well over 6000. For example, Lee et al. recently demonstrated an amperometric redox cycling sensor based on an interdigitated electrode (IDE) design for detecting the hepatitis B virus surface antigen. The sensor was combined with a commercial ELISA kit and demonstrated more than 10-fold higher sensitivity in dual-electrode mode compared to single-electrode mode, highlighting the potential of this technique for improving virus detection.

The charged surface of virions makes them prime candidates for electrophoretic manipulation. The surface charge is highly dependent on the medium properties, especially pH. Typically, viruses have an isoelectric point below pH 7, making them negatively charged at physiological pH values. As a result, the virus particles are preferentially attracted to the anode where they can attach to the electrode surface. Such particle collisions can alter the electrochemical landscape of the electrode and cause detectable changes in the local capacitance and charge transfer. This strategy, e.g., particle collision method, has been applied in the detection of bacteria, such as *Escherichia coli*, mammalian cells, and viruses, with the ultimate end goal being single entity detection in as little time as possible.

SUMMARY OF THE INVENTION

Embodiments relate to an electrochemical system arrangement in which finite element analysis (FEA) can be used to design electrodes of the system such that the advantages of redox cycling and electrophoretic enrichment are optimized for rapid detection and counting of single virus particles. The detection scheme can be based on a current quenching strategy whereby the electrochemical current from the cyclic reduction and oxidation of a redox couple ($[Fe(CN)_6]^{3-/4-}$ as model) can be suppressed as virus particles are captured at the electrode surface. Similar "current blocking" strategies have been exploited in prior art using individual microelectrodes.

Embodiments disclosed herein utilize two mushroom-like, generator-collector microelectrode configurations: 1) a ring-disk; and 2) an IDE. The ring-disk configuration may be more suitable for application in a digital microfluidic platform, whereas the IDE configuration may be more suitable for a traditional microfluidic channel. The mushroom-like design can be based on a scalable, templated electrodeposition strategy and yields tunable geometries that improve the redox cycling characteristics through reduced generator-collector spacing. The present disclosure demonstrates that various design parameters, including electrode geometry, testing geometry (e.g., microchannel, droplet), and experimental conditions (e.g., voltammetric scan rate, electrolyte concentration) are explored to better understand their effect on the amplification factor ($\Gamma$), collector efficiency ($\eta$), and optimization a biosensing system. Depending on the experimental parameters and electrode geometry, single virus collisions can be detected on the order of seconds. The computational results herein provide design rules and assist in guiding development of biosensors suitable for single particle counting, with potential applications including virus detection, immunoassays, and nanoparticle-based molecular diagnostics.

An exemplary embodiment can relate to an electrochemical system. The system can include a first working electrode, a second working electrode, and electrolyte. The first working electrode can include a particle capture region having an aspect ratio that is greater than 1. The particle capture region can be a portion of the first working electrode configured to attract a particle supported within the electrolyte.

In some embodiments, the first working electrode can be a generator electrode. The second working electrode can be a collector electrode.

In some embodiments, the electrochemical system can be a redox system.

In some embodiments, the electrochemical system can be a component of a biosensor. The particle capture region of the first working electrode can be a virion capture region.

In some embodiments, the first working electrode can include a pillar that is an elongate member having an aspect ratio that is less than 1. The particle capture region can be located at a distal end of the pillar.

In some embodiments, the particle capture region can have a toroid shape, a semi-toroid shape, a spherical shape, a semi-spherical shape, or a dome shape.

In some embodiments, a combination of the pillar with the particle capture region can exhibit a mushroom shape.

In some embodiments, the second working electrode can include an annular member.

In some embodiments, the second working electrode can include an elongate tube and the annular member. The annular member can be located at a distal end of the elongate tube. The second working electrode can at least partially surround the first working electrode.

In some embodiments, the second working electrode can surround the first working electrode in a concentric manner.

In some embodiments, the annular member can have a toroid shape, a semi-toroid shape, a spherical shape, a semi-spherical shape, or a dome shape.

In some embodiments, a combination of the elongate tube with the annular member can have a cross-section that exhibits a cross-sectional mushroom shape.

In some embodiments, the first working electrode can include a pillar extending from a generator electrode base. The pillar can be an elongate member having an aspect ratio that is less than 1. The particle capture region can be located at a distal end of the pillar. The second working electrode can include a pillar extending from a collector electrode base. The pillar can be an elongate member having an aspect ratio that is less than 1. The pillar can include a region located at a distal end thereof, the region having an aspect ratio that is greater than 1.

In some embodiments, the particle capture region of the first working electrode does not make physical contact with the second working electrode. The region of the second working electrode does not make physical contact with the first working electrode.

In some embodiments, the first working electrode can include plural pillars. The second working electrode can include plural pillars.

An exemplary embodiment can relate to a biosensor. The biosensor can include an electrochemical system. The system can include a generator electrode, a collector electrode, and electrolyte. The generator electrode can include a particle capture region having an aspect ratio that is greater than 1. The particle capture region can be a portion of the generator electrode configured to attract a particle supported within the electrolyte. The biosensor can include a processing module configured to measure electric current generated by the electrochemical system.

In some embodiments, the processing module can be configured to operate the electrochemical system such that one of the collector electrode or the generator electrode is biased below its formal potential while the other electrode is biased above its formal potential.

In some embodiments, the biosensor can be configured as a lab-on-a chip platform, a point-of-care detection apparatus, or an assay apparatus.

An exemplary embodiment can relate to a method of particle detection. The method can involve biasing one of a generator electrode or a collector electrode of an electrochemical system below its formal potential while biasing the other electrode of the electrochemical system above its formal potential, the electrochemical system including an analyte supported by an electrolyte. The method can involve introducing particles into the electrolyte of the electrochemical system. The method can involve quenching electrical current flow of the electrochemical system by particles travelling from the electrolyte and attaching to the generator electrode at a particle capture region and blocking or hindering transferring electrons from a redox molecule to the generator electrode. The method can involve resupplying analyte of the electrolyte by an oxidized molecule travelling from the generator electrode through the electrolyte and back to the collector electrode. The method can involve detecting a change in capacitance and/or electron charge transfer in the electrochemical system due to the particles attaching to the generator electrode. Spacing between the generator electrode and the collector electrode at the particle capture region can be set to increase the likelihood of confinement of the particles at the particle capture region, facilitate steady-state electron charge transfer of the electrochemical system, and decrease the likelihood of redox species depletion within the electrochemical system.

In some embodiments, the method can involve adjusting a pH of the medium to modulate a charge exhibited by the particles so that the charged particles are preferentially attracted to the generator electrode.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present innovation will be more apparent from the following more particular description thereof, presented in conjunction with the following drawings. Like reference numbers used in the drawings may identify like components.

FIGS. 25-28 show raw chronoamperometric scans in an exemplary ring-disk 1 μl droplet configuration for varying particle charge, wherein FIG. 25 shows the generator current, FIG. 26 shows the collector current, and FIGS. 27 and 28 show close-up of specific capture events as indicated by the arrows.

FIGS. 29-32 show raw chronoamperometric scans in an exemplary ring-disk 1 μl droplet configuration for varying particle number, wherein FIG. 29 shows the generator current, FIG. 30 shows the collector current, and FIGS. 31 and 32 show close-up of specific capture events as indicated by the arrows.

FIGS. 33-38 show raw chronoamperometric scans in an exemplary ring-disk 1 μl droplet configuration for varying particle size, wherein FIG. 33 shows the generator current, FIGS. 34 and 35 show close-ups of individual capture events, FIG. 36 shows the collector current, and FIGS. 37 and 38 show close-ups of individual capture events.

FIGS. 41-43 show the effect of various virus properties on the amperometric detection of capture events in a 1 μl droplet, wherein FIG. 41 shows the background subtracted current (ΔI) obtained from chronoamperometric measurements demonstrating the effect of the virus surface charge (q), FIG. 42 shows the effect of virus size ($d_p$), and FIG. 43 shows the effect of virus number (N).

DETAILED DESCRIPTION OF THE INVENTION

The following description is of exemplary embodiments that are presently contemplated for carrying out the present invention. This description is not to be taken in a limiting sense, but is made merely for the purpose of describing the general principles and features of the present invention. The scope of the present invention is not limited by this description.

Figure 1:
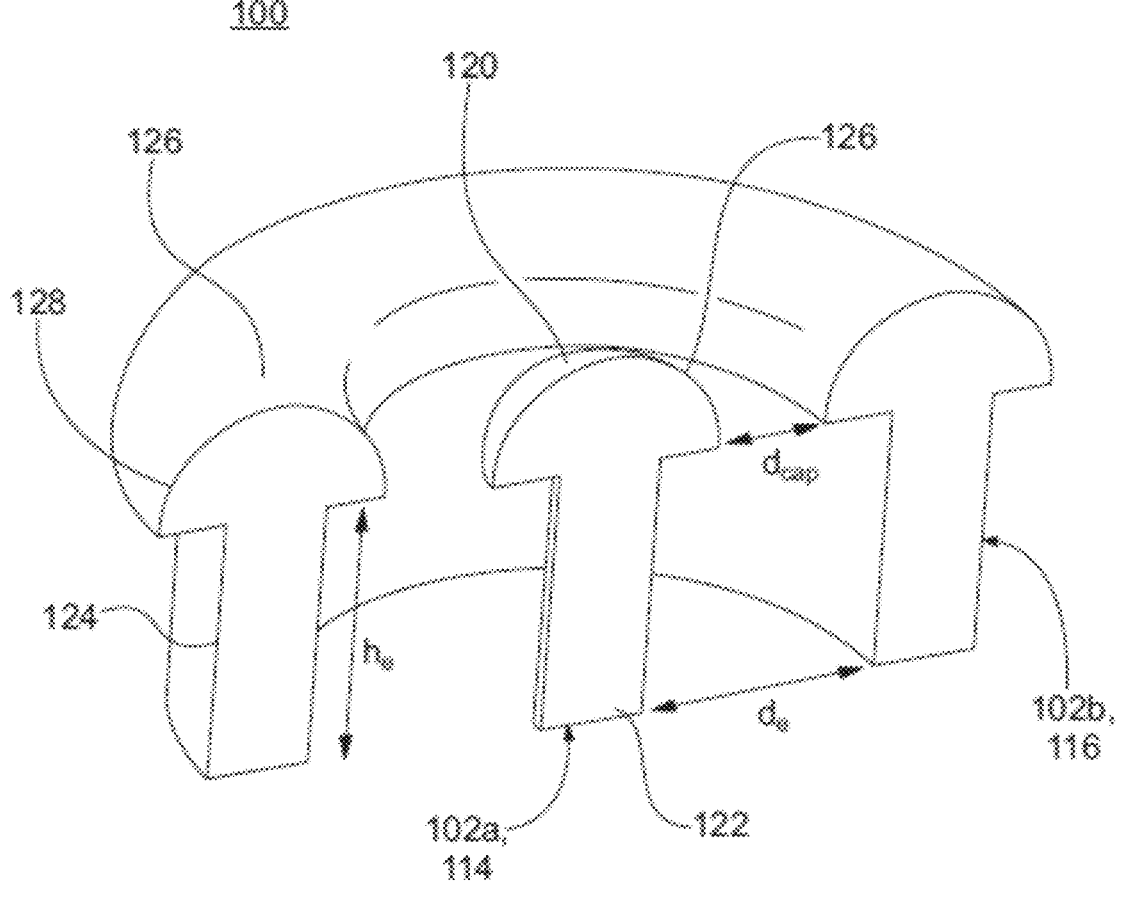
FIG. 1 shows an exemplary embodiment of a ring disk (cross-section) sensor geometry.
Figure 2:
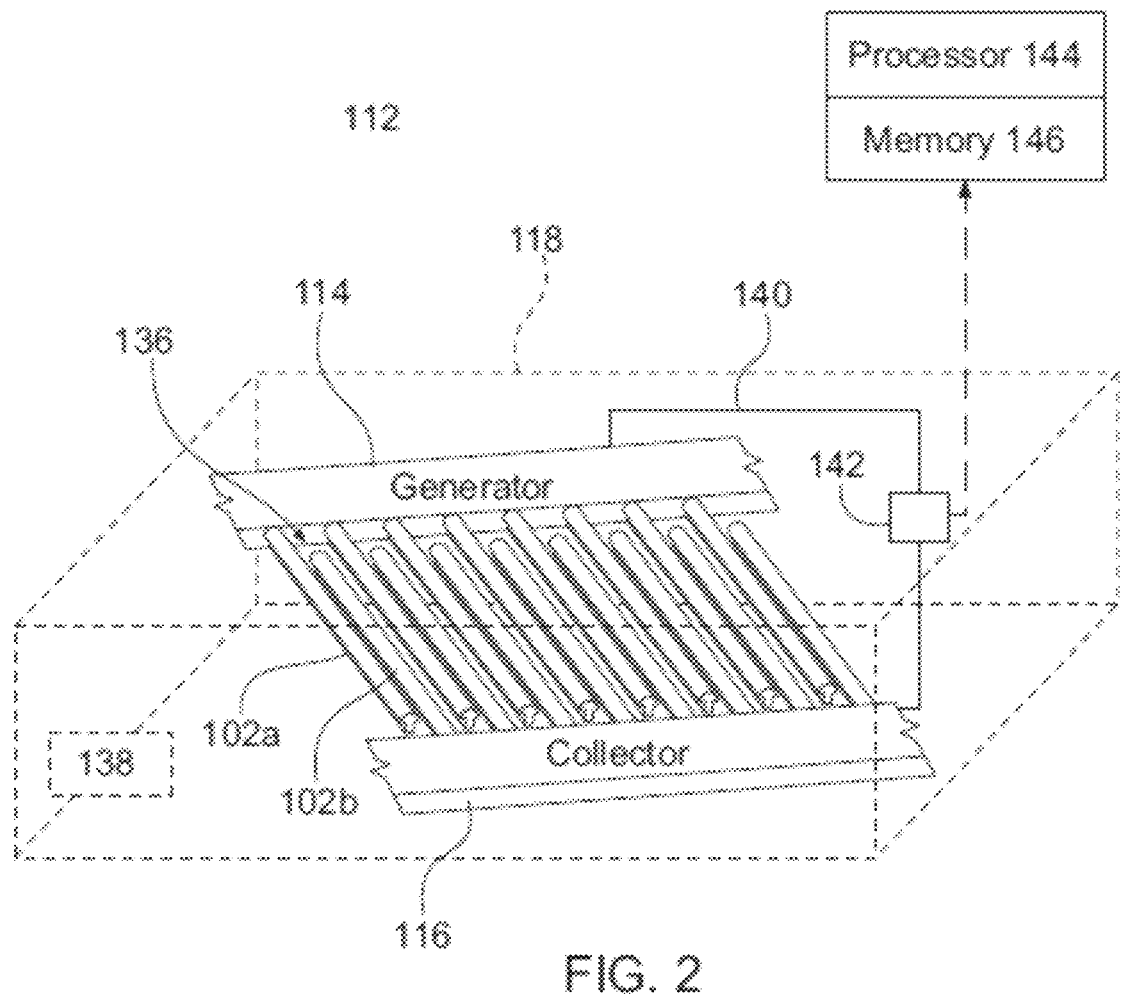
FIG. 2 shows an exemplary IDE sensor geometry.
Figure 3:
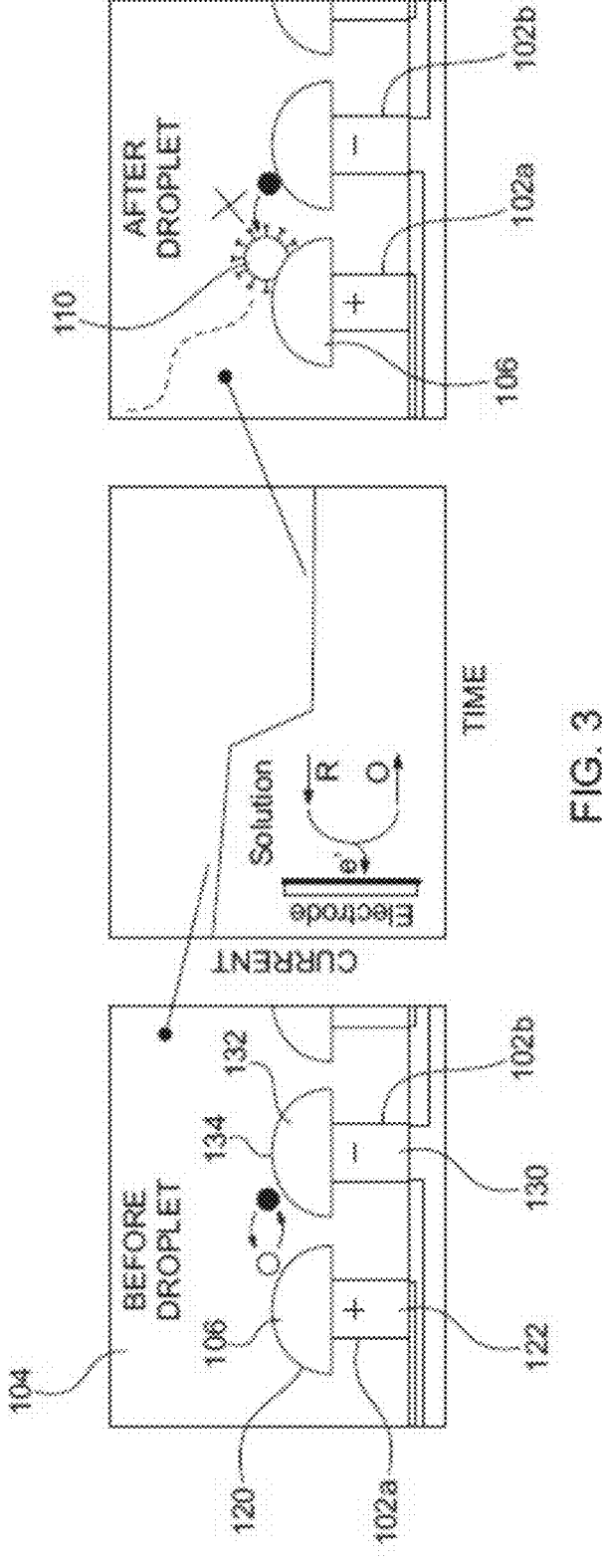
FIG. 3 illustrates an exemplary current quenching sensing mechanism before and after virus attachment.

Referring to FIGS. 1-3, an exemplary embodiment can relate to an electrochemical system 100. The system 100 can include a first working electrode 102a, a second working electrode 102b, and electrolyte 104. The first working electrode 102a can include a particle capture region 106 having an aspect ratio (a width to height ratio) that is greater than 1. The particle capture region 106 can be a portion of the first working electrode 102a configured to attract a particle 110 supported within the electrolyte 104. As will be explained herein, embodiments of the system 100 can be part of a biosensor 112. The biosensor 112 can be configured to detect presence, amount, and/or concentration of a biological substance (e.g., a virus). The system 100 can be configured such that the first working electrode 102a attracts the particle 110 (e.g., the virus). For instance, the first working electrode 102a can be positively charged and the particle 110 negatively charged, wherein the electrolyte 104 is configured to support the particle 110. Attraction of the particle 110 to the first working electrode 102a can cause the particle 110 to attach thereto and block or hinder the electron transfer between the redox molecule and electrode 102a. For instance, system 100 has electrolyte 104 that contains a redox molecule (or "probe") that transfers electrons with the electrodes 102a, 102b through a redox reaction. This is taking place even in the absence of any virus or particles 110. When the particles 110 attaches to the electrode, the redox reaction is "blocked" in that region, which results in a decrease in electrical current. The attachment of the particle 110 to the first working electrode 102a alters capacitance and/or electron charge transfer of the system 100, which allows for detection of the presence, amount, and/or concentration of the particle 110.

The system 100 can be configured as a redox system 100 (e.g., a system in which chemical reaction cause electrons move between two reactants of the system, wherein transfer of electrons is quantified by changes in oxidation states of reacting species). The first working electrode 102a can be a generator electrode 114, and the second working electrode 102b can be a collector electrode 116. The electrodes 102a, 102b can be housed within a casing 118. The casing 118 can contain electrolyte 104. The electrolyte 104 is medium containing ions that is electrically conducting through the movement of those ions. The redox molecule serves as the ions in this case, whereas the particle 110 blocks or reduces electron transfer. The casing 118 can be configured to contain other features and components of the electrochemical system 100 or biosensor 112, such as electrical contacts, processing modules, membranes, filters, etc. to facilitate proper and efficient operation of the system 100 or biosensor 112.

As noted herein, the electrochemical system 100 can be a component of a biosensor 112. Thus, the particle capture region 106 of the first working electrode 102a can be a virion capture region 106. In an exemplary embodiment, the first working electrode 102a can include a pillar 122 that is an elongate member having an aspect ratio that is less than 1. The particle capture region 106 can be located at a distal end 120 of the pillar 122. For instance, the first working electrode 102a can be a column, bar, or tube formation having a distal end 120. The distal end 120 can be the particle 110 (e.g., virion) capture region 106-a region of the first working electrode 102a to which the particle 110 attaches. Again, this region 106 can have an aspect ratio greater than 1. For instance, the particle capture region 106 can have a toroid shape, a semi-toroid shape, a spherical shape, a semi-spherical shape, or a dome shape. In an exemplary embodiment, a combination of the pillar 122 with the particle capture region 106 can exhibit a mushroom shape.

It is understood that the particle 110 can attach to any portion of the electrode 102a. However, the particle capture region 106 is a portion of the electrode 102a that, when the particle 110 attaches, generates the improved functionality (increase the likelihood of confinement of the particles 110, facilitate steady-state electron charge transfer of the electrochemical system 100, and decrease the likelihood of redox species depletion within the electrochemical system 100) due to its geometry and/or aspect ratio. Thus, the particle capture region 106 can be thought of as a preferred region for particle capture.

As shown in FIG. 1, the system 100 can be configured such that the second working electrode 102b includes an annular member 126. For instance, the second working electrode 102b can include an elongate tube 124 and an annular member 126. The annular member 126 can be located at a distal end 120 of the elongate tube 124. The elongate tube 124 can have sidewalls 128 defining an interior space, wherein the second working electrode 102b at least partially surrounds the first working electrode 102a. This can include surrounding the first working electrode 102a in a concentric manner. Thus, the first working electrode 102a can be a pillar 122 positioned within the interior space defined by the sidewalls 128 such that the sidewalls 128 and the annular member 126 surround, or at least partially surround, the pillar 122 and/or the particle capture region 106. The annular member 126 can have a toroid shape, a semi-toroid shape, a spherical shape, a semi-spherical shape, or a dome shape. In an exemplary embodiment, a combination of the elongate tube 124 with the annular member 126 can have a cross-section that exhibits a cross-sectional mushroom shape. This particular first and second electrode 102a, 102b configuration can form what may be referred to herein as a ring-disk formation or ring-disk configuration.

The system 100 configuration described and illustrated for the ring-disk formation is exemplary. It is understood that other arrangements and configurations can be used. For instance, the first and/or the second working electrode 102a, 102b can be tubular, square, hexagonal, etc. in shape. The first working electrode 102a can have one or more particle capture regions 106. The second working electrode 102b can have one or more annular members 126. The particle capture region 106 or the annular member 126 can be located anywhere along the first working electrode 102a or second working electrode 102b, respectively. The pillars, elongate tubes, the particle capture regions, annular members, etc. can be of any shape, provided the aspect ratios are as described above. There can be any number of first working electrodes 102a and any number of second working electrodes 102b. The second working electrode 102b can have the particle capture region 106 configuration while the first working electrode 102a has the annular member 126 configuration. Which electrode 102a, 102b has the particle capture region 106 depends on the application, and in particular the charge (positive or negative) on the particle 110 and the charge (positive or negative) of the electrodes 102a, 102b.

Any of the electrodes 102a, 102b disclosed herein can be made from a conductive, stable material, such as graphite, gold, silver, platinum, carbon, copper, titanium, etc.

As shown in FIG. 2, the first working electrode 102a can include a first working electrode pillar 122 extending from a generator electrode base 114. The first working electrode pillar 122 can be an elongate member having an aspect ratio that is less than 1. The particle capture region 106 can be located at a distal end 120 of the first working electrode pillar 122. The second working electrode 102b can include a second working electrode pillar 130 extending from a collector electrode base 116. The second working electrode pillar 130 can be an elongate member having an aspect ratio that is less than 1. The second working electrode pillar 130 can include a region 132 located at a distal end 134 thereof.

The region 132 can have an aspect ratio that is greater than 1. This embodiment can form what may be referred to herein as an interdigitated electrode (IDE) configuration. With the IDE configuration, the first and second electrodes 102a, 102b can each have geometries that are the same or similar to the first working electrode 102a of the ring-disk formation or ring-disk configuration. Notably, with the IDE configuration, the second working electrode 102b is not configured to and does not surround the first working electrode 102a. Instead, the second working electrode 102b is positioned adjacent or next to the first working electrode 102a without surrounding it. The electrodes 102a, 102b in the IDE configuration extend from a generator electrode base 114 and a collector electrode base 116, respectively. The bases 114, 116 are positioned such that their respective electrodes 102a, 102b extend towards the other base—e.g., the first working electrode 102a extends from the generator electrode base 114 and towards the collector electrode base 116, and the second working electrode 102b extends from the collector electrode base 116 and towards the generator electrode base 114.

With the IDE embodiment, the particle capture region 106 of the first working electrode 102a does not make physical contact with the second working electrode 102b (e.g., does not make contact with the collector electrode base 116). The region 132 of the second working electrode 102b does not make physical contact with the first working electrode 102a (e.g., does not make contact with the generator electrode base 114). These non-contact arrangements can form a fluidic channel 136 through which the electrolyte 104 resides and/or flows. For instance, the system 100 can form a microfluidic device with the first working electrode 102a extending from a generator electrode base 114 and the second working electrode 102b extending from a collector electrode base 116, wherein the generator electrode base 114 subtends the collector electrode base 116 and arranged such that the first working electrode 102a extends from the generator electrode base 114 and towards the collector electrode base 116 and the second working electrode 102b extends from the collector electrode base 116 and towards the generator electrode base 114. The bases 114, 116 and electrodes 102a, 102b can be housed within a casing 118. The spacing discussed above forms the fluidic channel 136 and the casing 118 contains electrolyte within the system 100 to allow it to reside and/or flow within the fluidic channel 136.

In an exemplary embodiment, the first working electrode 102a can include plural pillars 122. The second working electrode 102b can include plural pillars 130. For instance, the system 100 can form a microfluidic device having several first working electrodes 102a and several second working electrodes 102b. Each of these electrodes 102a, 102b may be referred to as an electrode digit. The arrangement of electrodes 102a, 102b can be such that they are interposed. Any number of first working electrodes 102a (or digits) can be interposed between two second working electrodes 102b (or digits). Similarly, any number of second working electrodes 102b (or digits) can be interposed between two first working electrodes 102a (or digits). This interposed arrangement can form the exemplary IDE configuration shown in FIG. 2. It is contemplated for the IDE configuration to form a row of interposed first and second working electrodes 102a, 102b. It is further contemplated for the first and second electrodes 102a, 102b to alternate within the interposed arrangement—e.g., as one follows the row, the arrangement is: a first working electrode 102a, a second working electrode 102b, a first working electrode 102a, a second working electrode 102b, etc.

The system 100 configuration described and illustrated for the IDE formation is exemplary. It is understood that other arrangements and configurations can be used. For instance, the first and/or the second working electrode 102a, 102b can be tubular, square, hexagonal, etc. in shape. The first working electrode 102a can have one or more particle capture regions 106. The second working electrode 102b can have one or more regions 132. The particle capture region 106 or the region 132 can be located anywhere along the first working electrode 102a or second working electrode 102b, respectively. The pillars 122, 130, the particle capture regions 106 and/or the regions 132 can be of any shape, provided the aspect ratios are as described above. There can be any number of first working electrodes 102a and any number of second working electrodes 102b. The second working electrode 102b can have the particle capture region 106 while the first working electrode 102a has the region 132. Which electrode 102a, 102b has the particle capture region 106 depends on the application, and in particular the charge (positive or negative) on the particle 110 and the charge (positive or negative) of the electrodes 102a, 102b. The arrangement of interposed electrodes 102a, 102b can form one or more rows (straight rows, curved rows, serpentine rows, etc.), one or more arrays (square array, circular array, etc.), or any other matrix formation. The arrangement of interposed electrode 102a, 102b can be alternating (first, second, first, second) or have some other type of arrangement.

An exemplary embodiment can relate to a biosensor 112. The biosensor can include an embodiment of the electrochemical system 100. The biosensor 112 can have an inlet 138 configured to receive a medium. The medium can be a sample that may or may not have the particle 110, as it is contemplated for the biosensor 112 to be used to determine the presence, amount, and/or concentration of the particle 110 in the sample. The medium is introduced into the inlet 138 such that it mixes with the electrolyte 104, wherein the electrolyte 104 supports the particle 110. The biosensor 112 can have electrical contacts 140 or leads connected to the electrodes 102a, 102b or electrode bases 114, 116. The electrical contacts 140 can be connected to a potentiostat to both measure one or more electrical characteristics—e.g. current, voltage, impedance, etc., and control the potential applied to the working electrode(s) 102a, 102b. This potentiostat can be in connection with or be part of a processing module 142. The processing module 142 can generate signals representative of the electrical characteristic(s) and process and/or store the signals. For instance, the processing module 142 can measure the current generated by the system 100 before introduction of the medium and measure the current generated by the system 100 after introduction of the medium. A change in current, no change in current, the amount of change in current, etc. can be used as a proxy for presence, amount, and/or concentration of the particle 110 in the sample. The processing module 142 can perform further signal processing and generate data related to the system 100—e.g., trend analysis, regression analysis, etc. The signals and/or the data can be transmitted to memory for storage or further processing, transmitted to another processor, displayed on a display device in textual or graphical format, used to generate an alarm (audio, visual, textual, etc.), etc. The biosensor 112 can be configured as a lab-on-a-chip platform, a point-of-care detection apparatus, an assay apparatus, etc.

The processing module 142 can include a processor 144 and memory 146, for example. Any of the processors 144 disclosed herein can be part of or in communication with a machine (e.g., a computer device, a logic device, a circuit, an operating module (hardware, software, and/or firmware), etc.). The processor 144 can be hardware (e.g., processor, integrated circuit, central processing unit, microprocessor, core processor, computer device, etc.), firmware, software, etc. configured to perform operations by execution of instructions embodied in computer program code, algorithms, program logic, control, logic, data processing program logic, artificial intelligence programming, machine learning programming, artificial neural network programming, automated reasoning programming, etc. The processor 144 can receive, process, and/or store data related to the system 100 and/or biosensor 112, for example.

Any of the processors 144 disclosed herein can be a scalable processor, a parallelizable processor, a multi-thread processing processor, etc. The processor 144 can be a computer in which the processing power is selected as a function of anticipated network traffic (e.g., data flow). The processor 144 can include any integrated circuit or other electronic device (or collection of devices) capable of performing an operation on at least one instruction, which can include a Reduced Instruction Set Core (RISC) processor, a CISC microprocessor, a Microcontroller Unit (MCU), a CISC-based Central Processing Unit (CPU), a Digital Signal Processor (DSP), a Graphics Processing Unit (GPU), a Field Programmable Gate Array (FPGA), etc. The hardware of such devices may be integrated onto a single substrate (e.g., silicon "die"), or distributed among two or more substrates. One or more functional aspects of the processor 144 may be implemented solely as software or firmware associated with the processor.

The processor 144 can include one or more processing or operating modules. A processing or operating module can be a software or firmware operating module configured to implement any of the functions disclosed herein. The processing or operating module can be embodied as software and stored in memory 146, the memory 146 being operatively associated with the processor 144. A processing module can be embodied as a web application, a desktop application, a console application, etc.

The processor 144 can include or be associated with a computer or machine readable medium. The computer or machine readable medium can include memory 146. Any of the memory 146 discussed herein can be computer readable memory configured to store data. The memory 146 can include a volatile or non-volatile, transitory or non-transitory memory, and be embodied as an in-memory, an active memory, a cloud memory, etc. Examples of memory 146 can include flash memory, Random Access Memory (RAM), Read Only Memory (ROM), Programmable Read only Memory (PROM), Erasable Programmable Read only Memory (EPROM), Electronically Erasable Programmable Read only Memory (EEPROM), FLASH-EPROM, Compact Disc (CD)-ROM, Digital Optical Disc DVD), optical storage, optical medium, a carrier wave, magnetic cassettes, magnetic tape, magnetic disk storage or other magnetic storage devices, or any other medium which can be used to store the desired information and which can accessed by the processor 144.

The memory 146 can be a non-transitory computer-readable medium. The term "computer-readable medium" (or "machine-readable medium") as used herein is an extensible term that refers to any medium or any memory, that participates in providing instructions to the processor 144 for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, transmission media, etc. The computer or machine readable medium can be configured to store one or more instructions thereon. The instructions can be in the form of algorithms, program logic, etc. that cause the processor to execute any of the functions disclosed herein.

Embodiments of the memory 146 can include a processor module and other circuitry to allow for the transfer of data to and from the memory 146, which can include to and from other components of a communication system. This transfer can be via hardwire or wireless transmission. The communication system can include transceivers, which can be used in combination with switches, receivers, transmitters, routers, gateways, wave-guides, etc. to facilitate communications via a communication approach or protocol for controlled and coordinated signal transmission and processing to any other component or combination of components of the communication system. The transmission can be via a communication link. The communication link can be electronic-based, optical-based, opto-electronic-based, quantum-based, etc. Communications can be via Bluetooth, near field communications, cellular communications, telemetry communications, Internet communications, etc.

Transmission of data and signals can be via transmission media. Transmission media can include coaxial cables, copper wire, fiber optics, etc. Transmission media can also take the form of acoustic or light waves, such as those generated during radio-wave and infrared data communications, or other form of propagated signals (e.g., carrier waves, digital signals, etc.).

Any of the processors 144 can be in communication with other processors of other devices (e.g., a computer device, a computer system, a laptop computer, a desktop computer, etc.). Any of the processors 144 can have transceivers or other communication devices/circuitry to facilitate transmission and reception of wireless signals. Any of the processors 144 can include an Application Programming Interface (API) as a software intermediary that allows two or more applications to talk to each other. Use of an API can allow software of one processor 144 to communicate with software of another processor 144.

The processing module 142 can also control operations of the electrochemical system 100. It is contemplated for the processing module 142 to operate the electrochemical system 100 such that one of the collector electrode 116 or the generator electrode 114 is biased below its formal potential while the other electrode 116, 114 is biased above its formal potential. For instance, one electrode 114, 116 can be biased above the formal potential ($E_0$) of the redox probe while the other is biased below, allowing the oxidized and reduced species to cycle between the electrodes 114, 116. This recycling can amplify the current, which can lead to increased signal-to-noise ratios.

As can be appreciated from the present disclosure, embodiments can relate to a method of particle 110 detection. The method can involve biasing one of a generator electrode 114 or a collector electrode 116 of an electrochemical system 100 below its formal potential while biasing the other electrode 114, 116 of the electrochemical system 100 above its formal potential. The method can involve introducing particles 110 into the electrolyte 104 of the electrochemical system 100. The method can involve quenching electrical current flow of the electrochemical system 100 by particles 110 travelling from the electrolyte 104 and attaching to the generator electrode 114 at a particle capture region 106 and blocking or hindering the transfer of electrons from a redox molecule (e.g., ($[Fe(CN)_6]^{3-/4-}$) to the generator electrode 114. The method can involve resupplying the analyte of the electrolyte 104 by an oxidized redox molecule travelling from the generator electrode 114 through the electrolyte 104 and back to the collector electrode 116. The method can involve detecting a change in capacitance and/or electron charge transfer in the electrochemical system 100 due to the particles 110 attaching to the generator electrode 114. Spacing between the generator electrode 114 and the collector electrode 116 at the particle capture region 106 can be set to increase the likelihood of confinement of the particles 110 at the particle capture region 106, facilitate steady-state electron charge transfer of the electrochemical system, and decrease the likelihood of redox species depletion within the electrochemical system 100.

It is contemplated for the particle 110 to be a virion, and the virion to be introduced into the electrochemical system 100 via a medium. Chemical engineering can be done to change or enhance the charge of the virion. For instance, the pH of the medium supporting the virion can be adjusted to cause the virion to be negatively or positively charged. Thus, the method can involve adjusting the pH of the medium to modulate a charge exhibited by the particles 110 so that the charged particles 110 are preferentially attracted to the generator electrode 114. With the particle 110 being a virion, the electrolyte 104 in the electrochemical system 100 can be KCl, saline, NaCl, etc. with $[Fe(CN)_6]^{4-}$ as the analyte. Other analytes or redox molecules could work as long as their redox reaction is reversible. The important consideration would be the formal potential of the particular analyte, such that the generator and collector electrodes 114, 116 can be biased appropriately above and below the formal potential.

EXAMPLES

The following describes and illustrates exemplary configurations and test results of the devices and systems disclosed herein.

As will be explained in more detail, the sensing strategy relies on a current quenching mechanism. When a virus particle attaches to the electrode surface (mainly driven by the electrophoretic force on the charged virions), it blocks additional redox reactions from occurring in that location. As a result, the current is reduced by a factor proportional to the particle surface area. The current steps can be modeled as, $$I_{total}(t) = I_{bg}(t) * \left(1 - \frac{n_p(t) * 4\pi r_p^2}{A_e}\right)$$

where $I_{total}(t)$ is the recorded chronoamperometric current, $I_{bg}(t)$ is the baseline current that is measured without any particles attached, $n_p(t)$ is the number of particles that attach to the electrode surface, which is a function of time, $r_p$ is the virus particle radius, and $A_e$ is the total electrode area.

Thus, the steps in the amperometric current can be proportional to the particle surface area and the electrode area. Consequently, a smaller electrode (e.g., small $A_e$) will be more sensitive to particle capture because the particle will block a larger portion of the total area than would be the case with an electrode of large area, such as a macroelectrode. The area of the electrode in the droplet configuration is computed by integrating the 2D surface in a revolved geometry over the interval of $2\pi$. The area is integrated over an interval of $\pi$ due to the symmetry used for the exemplary designs. For the IDE, the area is computed by integrating over the 2D cross-section and extending 0.5 mm in the perpendicular out-of-plane direction. Simulations are use for testing and the results off which are explained in detail below. A free triangular mesh is used for all simulations. For the axisymmetric 1 µl droplet configuration (the ring-disk), the mesh contains ~12000 elements with ~1000 boundary elements. The mesh elements in the regions surrounding the electrode boundaries are limited to 50 nm or less to ensure sufficient resolution of steep spatial gradients. For the interdigitated geometry, a maximum mesh element of 300 nm is used, which results in ~107000 total mesh elements with ~17000 boundary elements. For the virus particle capture simulations, an initial timestep of $10^{-9}$ to $10^{-12}$ s is used in order to capture the initial changes in particle motion from their stationary positions at $t_0$.

FIG. 1 shows an exemplary embodiment of a ring disk (cross-section) sensor geometry. FIG. 2 shows an exemplary IDE sensor geometry. FIG. 3 illustrates an exemplary current quenching sensing mechanism before and after virus attachment. When a virus particle attaches, it blocks or hinders mass transfer that drives the redox cycling. As a result, the magnitude of the electrochemical current is reduced. An example oxidation reaction is included in the inset. Reduced species (R) travels from the bulk solution to the electrode surface where it transfers an electron (e−) to form the oxidized species (O), which then travels back to the bulk solution. The exemplary generator-collector ring-disk configuration includes of two concentric 3D microelectrodes, an inner "disk" and outer "ring" for the droplet-based design. For this configuration, a 1 µl hemispherical droplet (unless otherwise specified) containing 1 mM $[Fe(CN)_6]^{4-}$ in a supporting KCl electrolyte is used. For the exemplary interdigitated electrode (IDE) design, two electrodes with comb-like fingers are placed in an alternating pattern and contained within a microfluidic channel. At the top of each electrode is a mushroom-like cap that can be formed by a template-driven over-electrodeposition. The width of the electrodes ($w_e$) is 2 µm which is within the resolution of standard photolithography methods. The electrode cap distance ($d_{cap}$) can be controlled through the electrodeposition parameters (e.g., deposition time, temperature, applied potential).

Due to the azimuthal symmetry of the ring-disk configuration, electrochemical characterization is performed using a 2D axisymmetric geometry and/or a 2D cross-sectional geometry. 2D cross-sectional geometry may be used due to discrepancies in the electric field at the axis of symmetry when using an axisymmetric geometry, which causes incorrect particle behavior. Note that the current for the ring-disk configuration is computed by integrating over a revolved geometry to ensure correct current values. For the IDE, a 2D cross-sectional geometry is used with an out-of-plane thickness of 0.5 mm. The IDE is 1 mm in length and is comprised of nearly 250 digits. Each electrode digit has a width $w_e$=2 µm with 2 µm spacing between adjacent digits ($\alpha$). The height of the microfluidic channel above the IDE is set to 15 µm and 1.07 mm in length in the simulations.

15

16

Electrochemical Simulations

Figure 4:
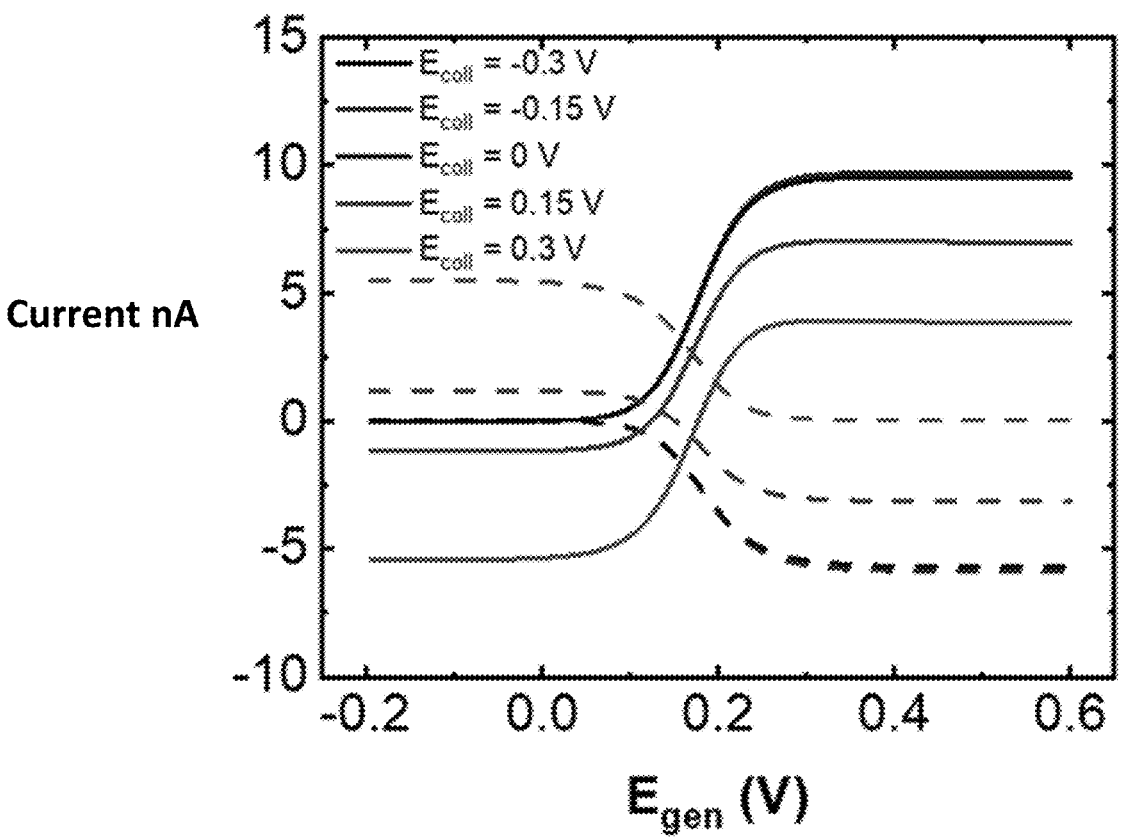
FIG. 4 shows the effect of varying the collector bias ($E_{coll}$) with the ring-disk configuration.

Finite element analysis (FEA) is performed using COMSOL Multiphysics versions 5.5 and 5.6 with the Tertiary Current Distribution electrochemistry module. An electroneutrality condition is maintained throughout the electrolyte (e.g., $\Sigma_i z_i c_i = 0$, where $z_i$ and $c_i$ are the charge number and concentration of species i). As a result, the concentration of Cl in the KCl, electrolyte is determined by the solver such that this condition is upheld. The $K^+$ concentration in the supporting electrolyte is made up of the KCl concentration, along with contributions from the $[Fe(CN)_6]^{4-}$. Electrochemical analysis is carried out in a generator-collector configuration whereby the two working electrodes are biased independently. For instance, the collector is held at a bias $E_{coll} = -0.15$ V while the generator ($E_{gen}$) is swept across a range of potentials, except when studying the effect of collector bias where other values of $E_{coll}$ are used (see FIG. 4). FIG. 4 shows the effect of varying the collector bias ($E_{coll}$) with the ring-disk configuration. The solid lines represent the generator current while the dashed lines are the corresponding collector current. Parameters: 1 mM $[Fe(CN)_6]^{4-}$, 1 mm KCl, scan rate=50 mV s$^{-1}$, $d_{cap}$=0.5 µm, $d_e$=2 µm, $h_e$=8.5 µm.

Figure 5:
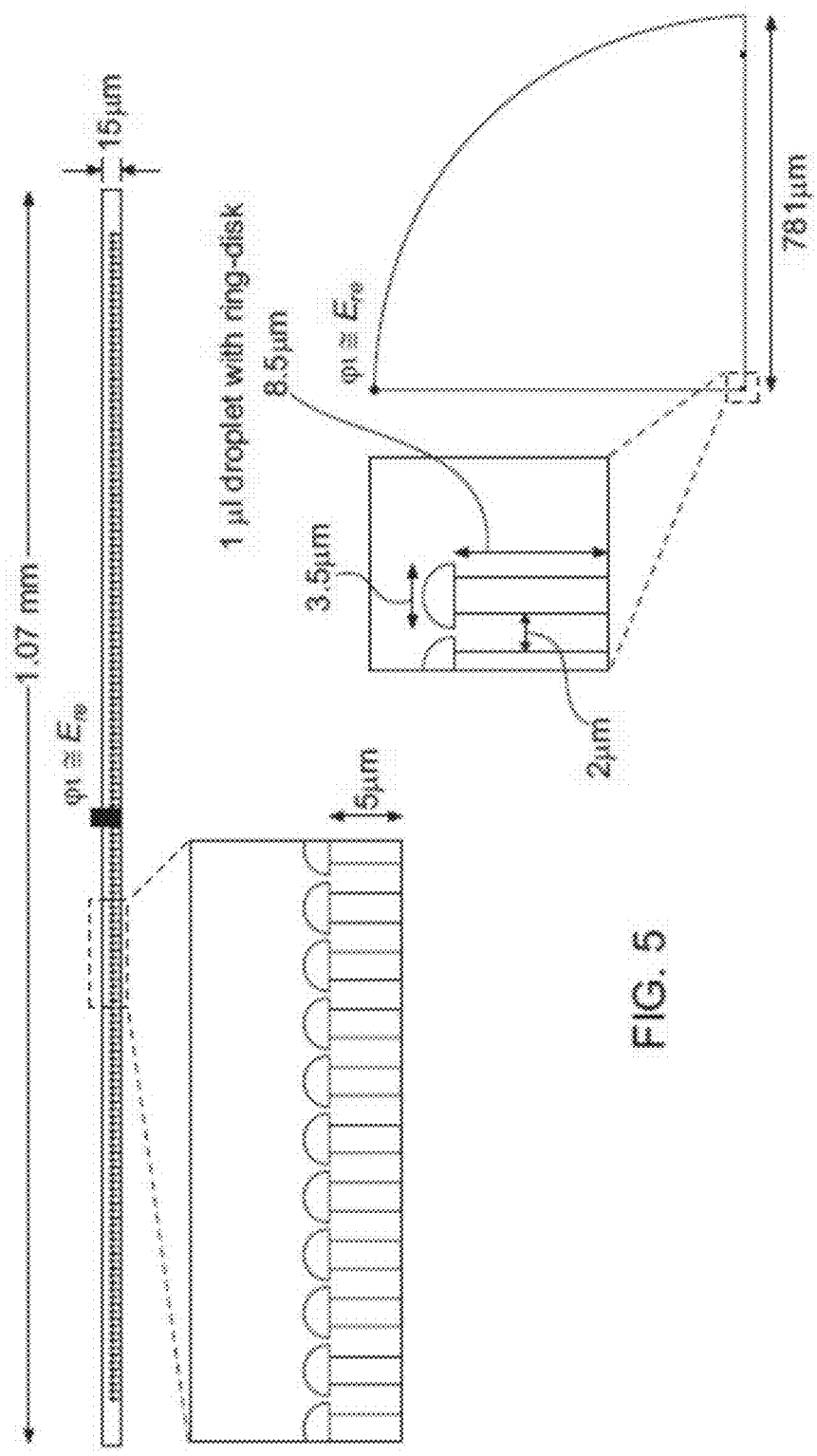
FIG. 5 shows exemplary IDE and 1 μl droplet model geometries.

The amplification factor ($\Gamma$) and collector efficiency ($\eta$) are calculated at the end of the voltammetric sweep, where $E_{gen}$=0.6 V. For the chronoamperometric measurements, $E_{coll}$=−0.15 V and $E_{gen}$=0.6 V are used. All simulations are referenced to an Ag/AgCl reference electrode ($E_{re}$=0.197 V). The electrolyte potential ($\phi_l$) is set equal to $E_{re}$ at points at the top-center of the droplet (x=0), or at the top of the microchannel in the IDE configuration (x=0). See FIG. 5 for more details. FIG. 5 shows exemplary IDE and 1 µl droplet model geometries. The points where the electrolyte potential ($\phi_l$) is equal to the reference electrode potential ($E_{re}$) are indicated.

The mass transport of species i is governed by the Nernst-Planck equation for diffusive and migrative transport, $$ J_i = -D_i \nabla c_i - u_{m,i} z_i c_i F \nabla \phi_l \qquad (1) $$

where $J_i$ is the flux, D is the diffusion coefficient, µm is the mobility, F is Faraday's constant, and $\phi_l$ is the electrolyte potential. The mobility µm of species i is related to the diffusion coefficient through the Nernst-Einstein relationship, $$ u_{m,i} = \frac{D_i}{RT} \qquad (2) $$

where R is the molar gas constant, and T is the temperature. The one-electron electrochemical reaction at the electrode-electrolyte interface can be written as follows, $$ [Fe(CN)_6]^{3-} + e^- \leftrightarrow [Fe(CN)_6]^{4-} \qquad (3) $$

which has a formal potential $E^0$=0.173 V vs. Ag/AgCl. The resulting electrochemical current from this reaction is modeled using Butler-Volmer kinetics, $$ i = i_0 \left[ \exp\left( \frac{\alpha_a n F \eta}{RT} \right) - \exp\left( -\frac{(1 - \alpha_a)) n F \eta}{RT} \right) \right] \qquad (4) $$

where $i_0$ is the exchange current (dependent upon $k^0$, the reaction rate constant), $\alpha_a$ is the anodic transfer coefficient, n is the number of electrons transferred in the reaction, and $\eta$ is the overpotential. The overpotential is expressed as, $$ \eta = \varphi_s - \varphi_l - E_{eq} \qquad (5) $$

where $\phi_s$ is the potential on the electrode boundary, $\phi_l$ is the potential in the electrolyte domain, and $E_{eq}$ is the equilibrium potential of the redox reaction as determined by the Nernst equation, $$ E_{eq} = E^0 - \frac{RT}{nF} \log\left( \frac{c_{red}}{c_{ox}} \right) \qquad (6) $$

where $c_{ox}$ and $c_{red}$ represent the concentration of oxidized and reduced species, respectively. The values of electrochemical parameters used are presented in Table 1.

TABLE 1

The electrochemical parameters used in simulations

| Parameter | Value |
|---|---|
| $c_{red}*$ | 1 mM |
| $k^0$ | 0.1 cm s$^{-1}$ |
| $D_{ox}$ | $7.2 \times 10^{-6}$ cm$^2$ s$^{-1}$ |
| $D_{red}$ | $6.4 \times 10^{-6}$ cm$^2$ s$^{-1}$ |
| $\alpha_a$ | 0.50 |
| n | 1 |

Joule heating and heat transfer effects are coupled to the other physics modules through a heat transfer in fluids physics module. The heat generated by current flow through the electrolyte is dissipated through the electrode and bottom substrate boundaries. A heat transfer coefficient (h) of 10 W m$^{-2}$ K$^{-1}$ is used. An external temperature ($T_{ext}$) of 298 K is used. The remaining boundaries are assumed to be insulating.

Modeling the Virus Particle in an Electric Field

The virus particles are subject to a random release at t=0 as the simulation begins. Each virus particle experiences drag ($F_D$), electrophoretic ($F_{EP}$), and dielectrophoretic ($F_{DEP}$) forces. The Stokes drag force equation can be expressed as, $$ F_D = 6 \mu \pi r_p (\vec{u} - \vec{v}) \qquad (7) $$

where µ is the fluid viscosity, $r_p$ is the particle radius, $\vec{u}$ is the fluid velocity, and $\vec{v}$ is the particle velocity. For the electrolyte solution in the droplet configuration, a 30% wt. water-glycerol mixture is used to limit evaporation during practical experiments. In this case, a viscosity of $2.13 \times 10^{-3}$ Pa s is calculated based on the formulation presented in ref. The density of the solution is 1.07 g cm$^{-3}$, and the dielectric constant used is 68. The virus particle density is 1.3 g cm$^{-3}$. For the IDE design, which is embedded in a microfluidic channel, simulations are done in an aqueous KCl electrolyte without added glycerol. The enclosed nature of the microfluidic channel eliminates the need for the use of glycerol.

The electrophoretic force on a particle is given as, $$F_{EP} = -eq\nabla\phi_l \tag{8}$$

where e is the elementary charge, q is the charge number of the particle, and $\phi_l$ is again the electrolyte potential, which is obtained by coupling with the electrochemical module. The dielectrophoretic force can be written as, $$F_{DEP} = 2\pi r_p^3 \varepsilon_0 \mathrm{Re}(\varepsilon_m)\mathrm{Re}(K)\nabla|\vec{E}|^2 \tag{9}$$

where so is the permittivity of free space, $\varepsilon_m$ is the dielectric constant of the medium, K is the Clausius-Mossotti function $$\left(K = \frac{\varepsilon_p^* - \varepsilon_m^*}{\varepsilon_p^* + 2\varepsilon_m^*}\right)$$

where $\varepsilon_p$ is the dielectric constant of the particle), and $\vec{E}$ is the electric field. The asterisk denotes the complex dielectric constant given as $\varepsilon_r^* = \varepsilon_r - j\sigma/\omega$ where j, $\sigma$, and $\omega$ represent the imaginary unit, electrical conductivity, and angular frequency, respectively. The dielectric constant of the droplet solution (glycerol-water mixture) is 68, whereas the dielectric constant for the aqueous electrolyte in the IDE microchannel is obtained from the COMSOL material library.

The virus particles are modeled as an inner sphere with an encapsulating outer layer with dielectric constants of $\varepsilon_1=75$ and $\varepsilon_2=7.5$, respectively, unless otherwise noted. The effective dielectric constant of a sphere with an outer shell can be calculated with Eq. 10, $$\varepsilon_{p,eff} = \varepsilon_2^* \frac{(r_2/r_1)^3 + 2\frac{\varepsilon_1^* - \varepsilon_2^*}{\varepsilon_1^* + 2\varepsilon_2^*}}{(r_2/r_1)^3 - \frac{\varepsilon_1^* - \varepsilon_2^*}{\varepsilon_1^* + 2\varepsilon_2^*}} \tag{10}$$

where $r_2$ is the total particle radius from center to outer shell, $r_2$ is the radius of just the inner sphere, and $\varepsilon_1$ and $\varepsilon_2$ are the dielectric constants of the shell and core, respectively.

Figure 6:
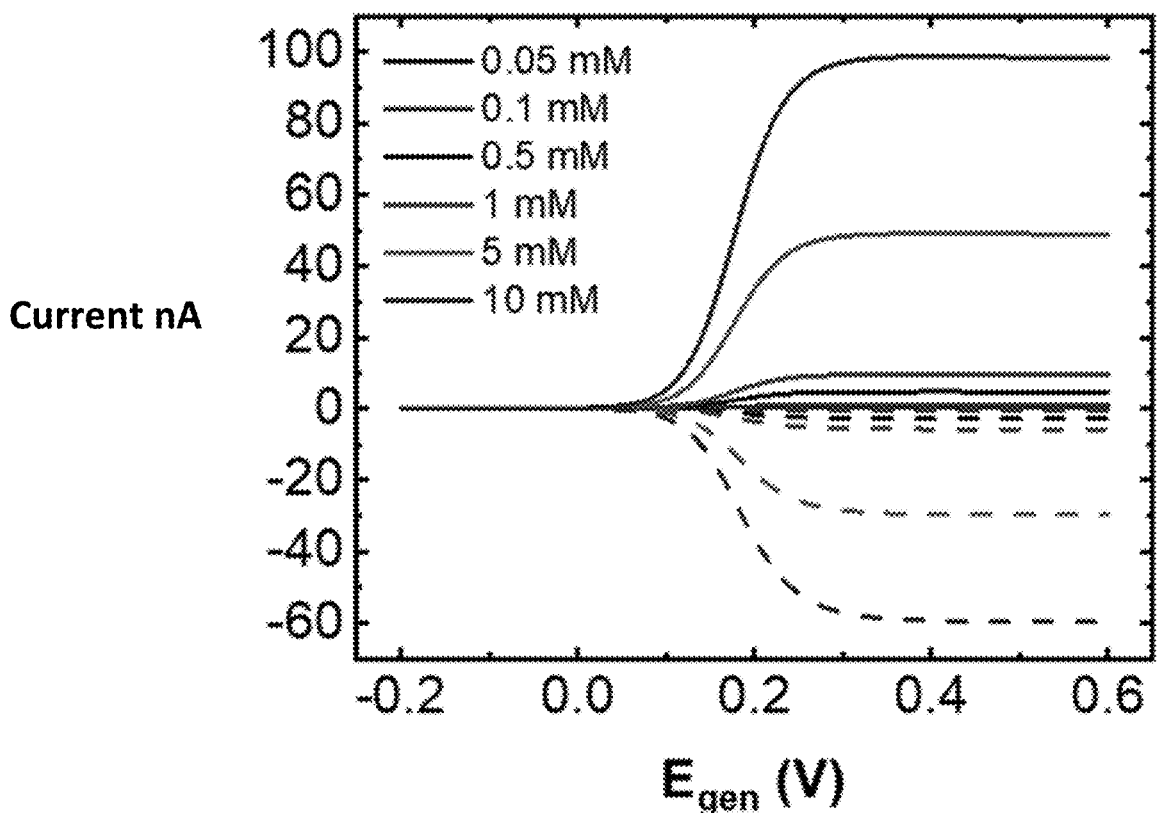
FIG. 6 shows the effect of $[Fe(CN)_6]^{4-}$ concentration on the electrochemical response of an exemplary generator-collector ring-disk geometry.

Electrochemical Analysis of the Ring-Disk (Droplet) Generator-Collector Configuration Before introducing the virus particles into the models, the baseline electrochemical properties are evaluated in the absence of virus particles. The disk and ring microelectrodes are located at the center of a 1 µl hemispherical droplet containing 1 mM $[Fe(CN)_6]^{4-}$ ($E^0=0.173$ V vs. Ag/AgCl) in a supporting KCl electrolyte (1 mM) (see FIG. 6 for the effect of $[Fe(CN)_6]^{4-}$ concentration). FIG. 6 shows the effect of $[Fe(CN)_6]^{4-}$ concentration on the electrochemical response of the generator-collector ring-disk geometry. The solid lines represent the generator current while the dashed lines are the corresponding collector current. Parameters: 1 mM KCl, $E_{coll}=\sim 0.15$ V, scan rate=50 m V s$^{-1}$, $d_{cap}=0.5$ µm, $d_e=2$ µm, $h_e=8.5$ µm.

At the top, both electrodes have a mushroom-like cap that can be created via a template-driven overgrowth during electrodeposition, similar to reports from Garimella et al. An advantage of this overgrowth is that the spacing between generator and collector electrode caps ($d_{cap}$) is tunable and can be decreased beyond the predefined pillar spacing by controlling the electrodeposition current and duration. Decreasing the generator-collector spacing is crucial for the diffusion-driven redox cycling process, while the high aspect ratio of the three-dimensional electrodes enables better confinement of redox species and results in an increased amplification factor ($\Gamma=I_{dual-mode}/I_{single-mode}$), where $I_{dual-mode}$ and $I_{single-mode}$ represent the steady-state current with and without redox cycling, respectively.

Figure 7:
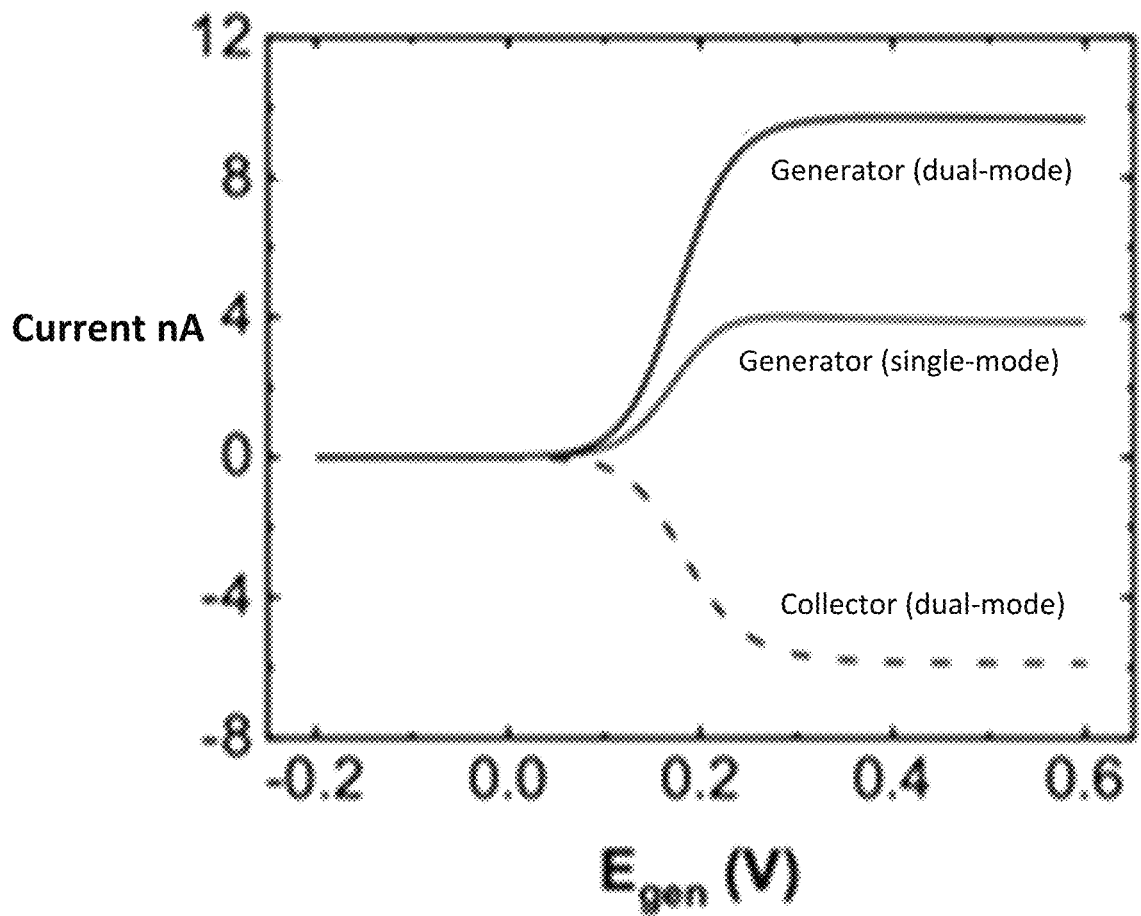
FIG. 7 is a representative voltammogram of an exemplary ring-disk microelectrode configuration in single- and dual-mode (1 mM $[Fe(CN)_6]^{4-}$, 1 mM KCl, scan rate=50 mVs$^{-1}$, $E_{coll}$=–0.15 V or floating).
Figure 8:
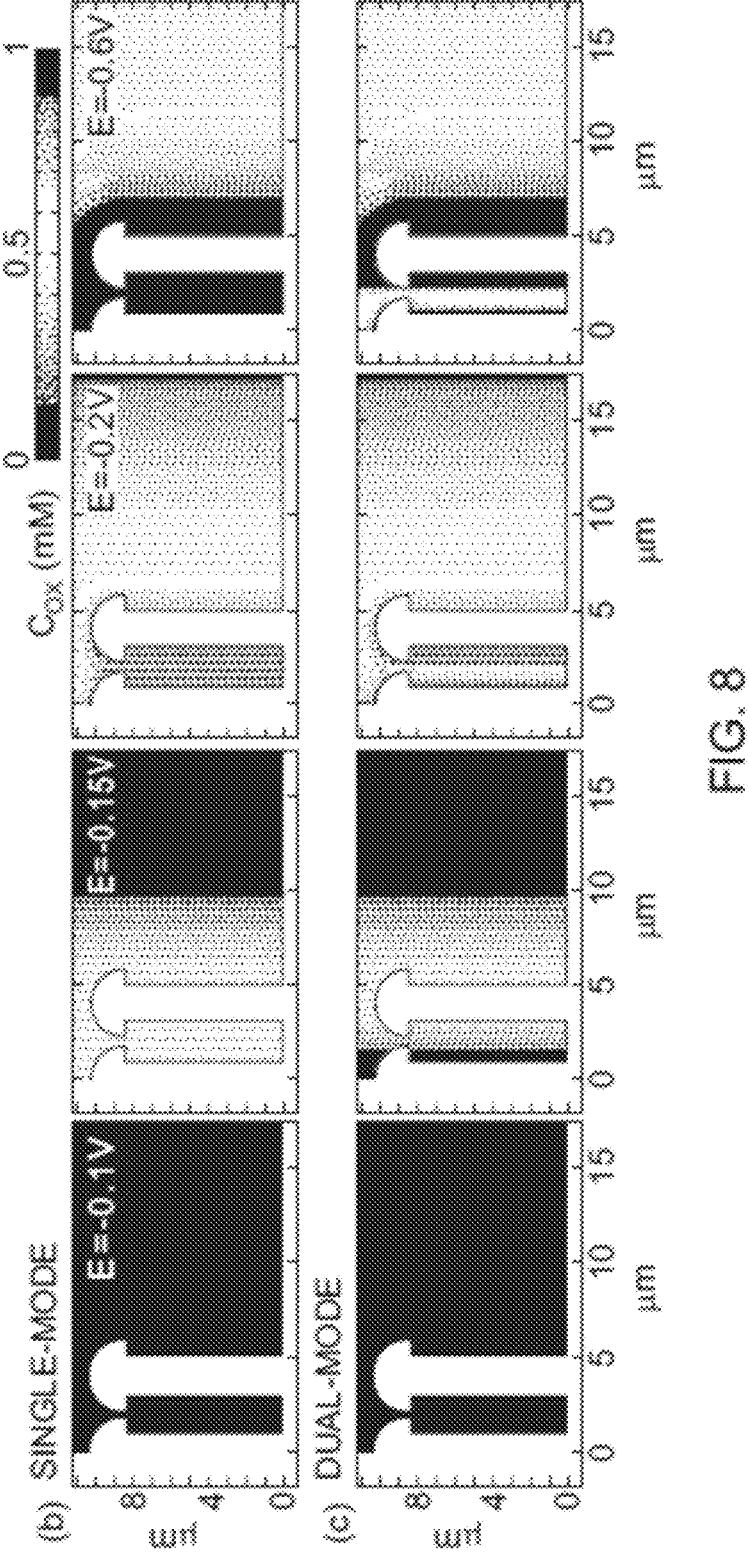
FIG. 8 shows concentration profiles of $[Fe(CN)_6]^{3-}$ for single-mode and dual-mode over the course of a voltammetric scan.

FIG. 7 is a representative voltammogram of the ring-disk microelectrode configuration in single- and dual-mode (1 mM $[Fe(CN)_6]^{4-}$, 1 mM KCl, scan rate=50 mVs$^{-1}$, $E_{coll}=\sim 0.15$ V or floating). FIG. 8 shows the resulting concentration profiles of $[Fe(CN)_6]^{3-}$ for single-mode and dual-mode over the course of the voltammetric scan. Note that the formal potential of the redox probe is around 0.17 V.

FIG. 7 demonstrates the enhancement of the Faradaic current resulting from the recycling of redox-active species compared to a single electrode. The linear sweep voltammograms (LSV) are carried out at a scan rate of 50 mV s$^{-1}$ (see FIG. 9 for effect of scan rate) with $E_{gen}$ ranging from −0.2 to 0.6 V while $E_{coll}$ is either held constant at −0.15 V in dual-mode (see FIG. 4 for effect of different generator biases) or left floating in single-mode. The current shows the typical steady-state behavior encountered with microelectrodes. The subsequent concentration profiles for the oxidized species ($c_{ox}$) are shown in FIG. 8 at four points during the potential scan. As expected in the dual-mode configuration, a steep concentration gradient starting around $E_{gen}=0.2$ V is seen between generator and collector electrodes that is not seen in single-mode. Because the flux of a species at an electrode is dependent on the concentration gradient, redox cycling can result in substantial amplification factors and explains the increased generator current seen in FIG. 7.

Figure 9:
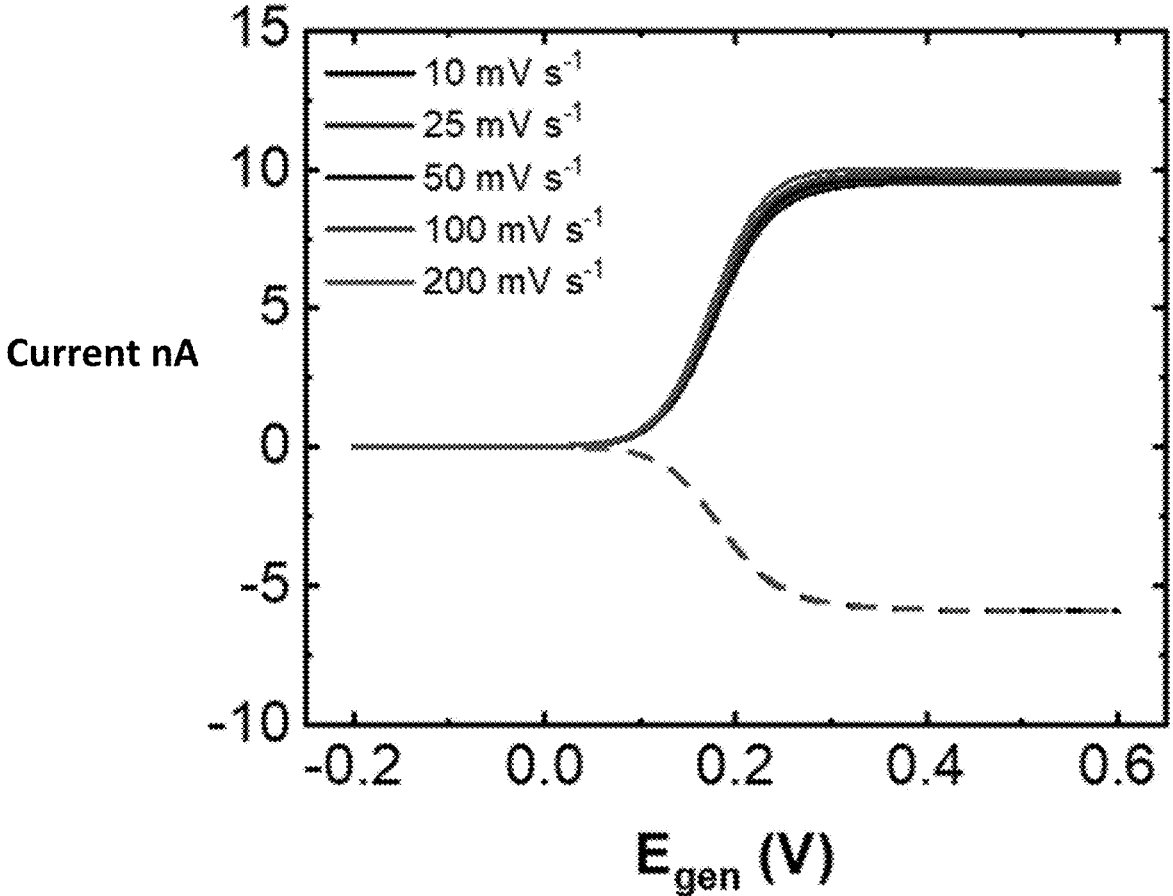
FIG. 9 shows the effect of voltammetric scan rate with an exemplary ring-disk configuration.

FIG. 9 shows the effect of the voltammetric scan rate with the ring-disk configuration. The solid lines represent the generator current and dashed lines represent the collector current. Parameters: 1 mM $[Fe(CN)_6]^{4-}$, 1 mm KCl, $E_{coll}=\sim 0.15$ V, $d_{cap}=0.5$ µm, $d_e=2$ µm, $h_e=8.5$ µm.

Figure 10:
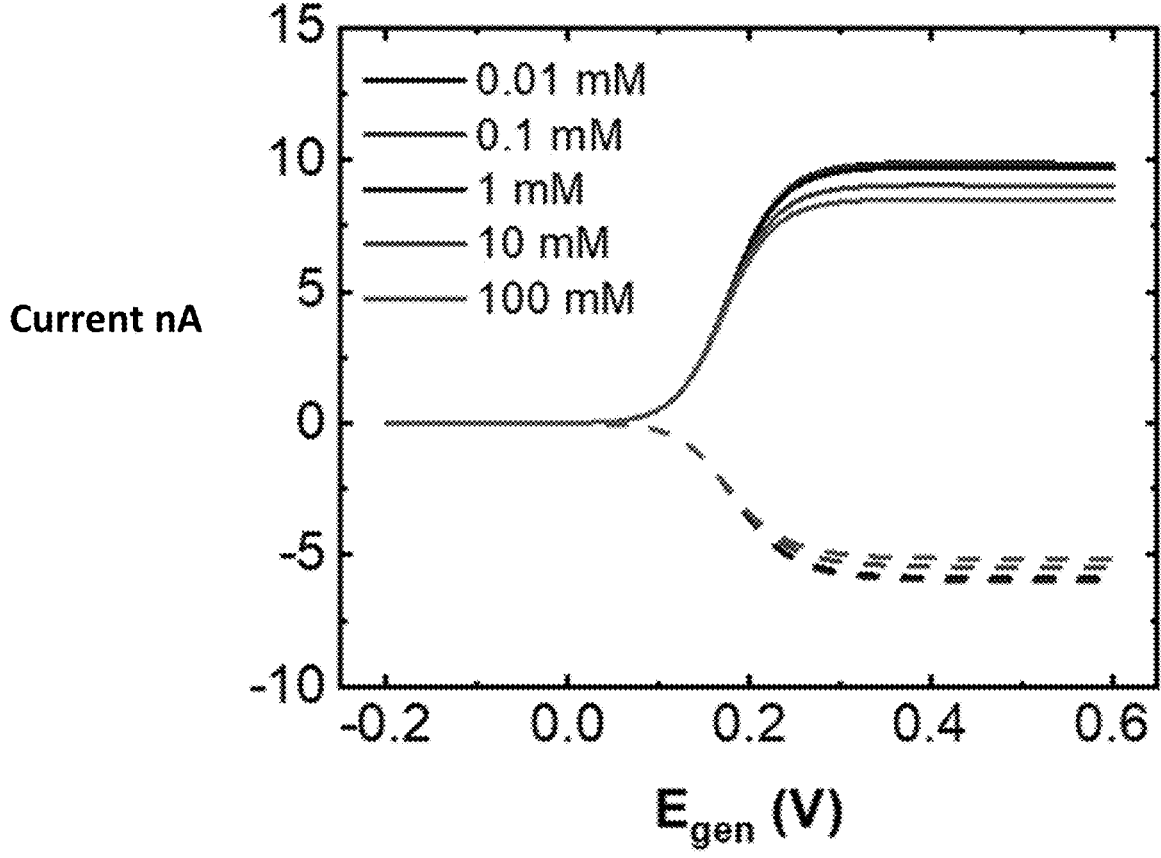
FIG. 10 shows the effect of KCl electrolyte concentration on electrochemical response of an exemplary generator-collector ring-disk geometry.
Figure 11:
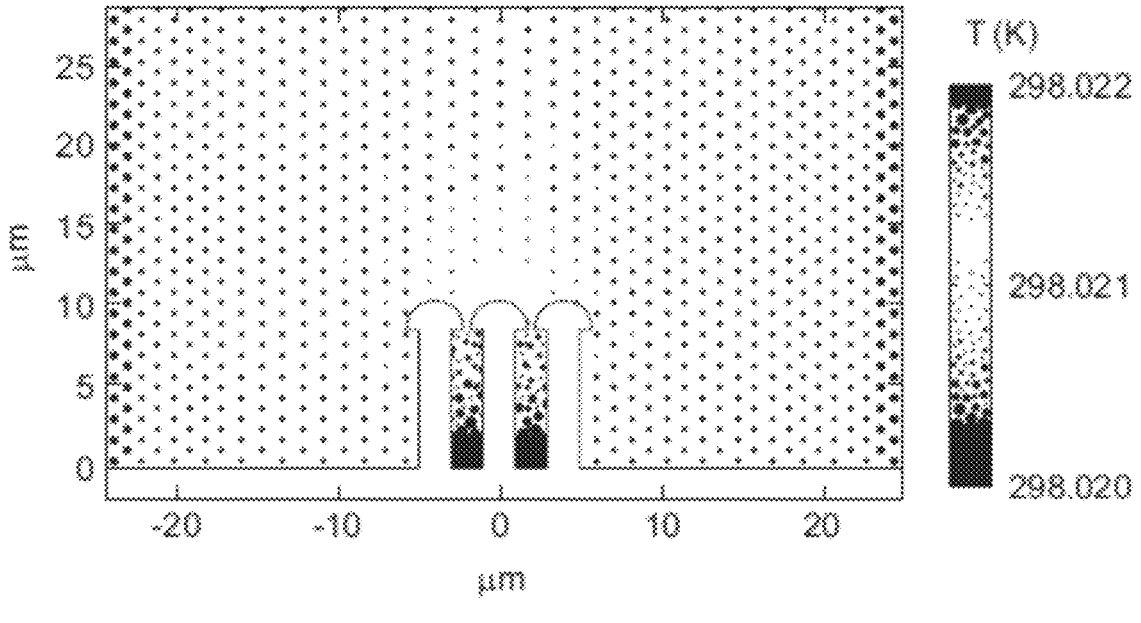
FIG. 11 shows the effect of Joule heating after 1200 s during a chronoamperometric scan in an exemplary 1 μl droplet configuration.
Figure 12:
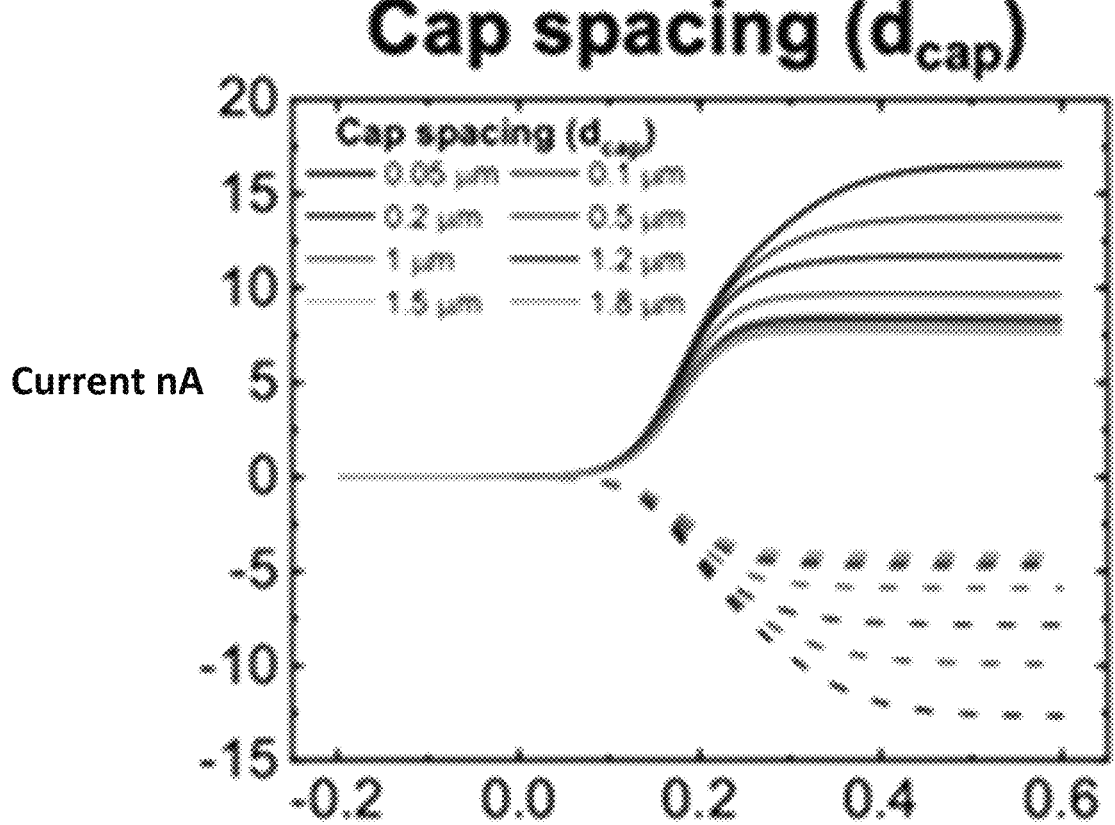
FIGS. 12-20 show effects of exemplary generator-collector geometries on the redox cycling characteristics, wherein FIGS. 12-14 relate to the linear sweep voltammograms (Parameters: 1 mM $[Fe(CN)_6]^{4-}$, 1 mm KCl, scan rate=50 mV s$^{-1}$, $E_{coll}$=–0.15 V) demonstrating the effect of cap spacing ($d_{cap}$), electrode height ($h_e$), and electrode spacing ($d_e$), respectively, wherein FIGS. 15-17 relate to the subsequent amplification factors (Γ), and wherein FIGS. 18-20 relate to collector efficiencies (η) as functions of electrode geometry.
Figure 13:
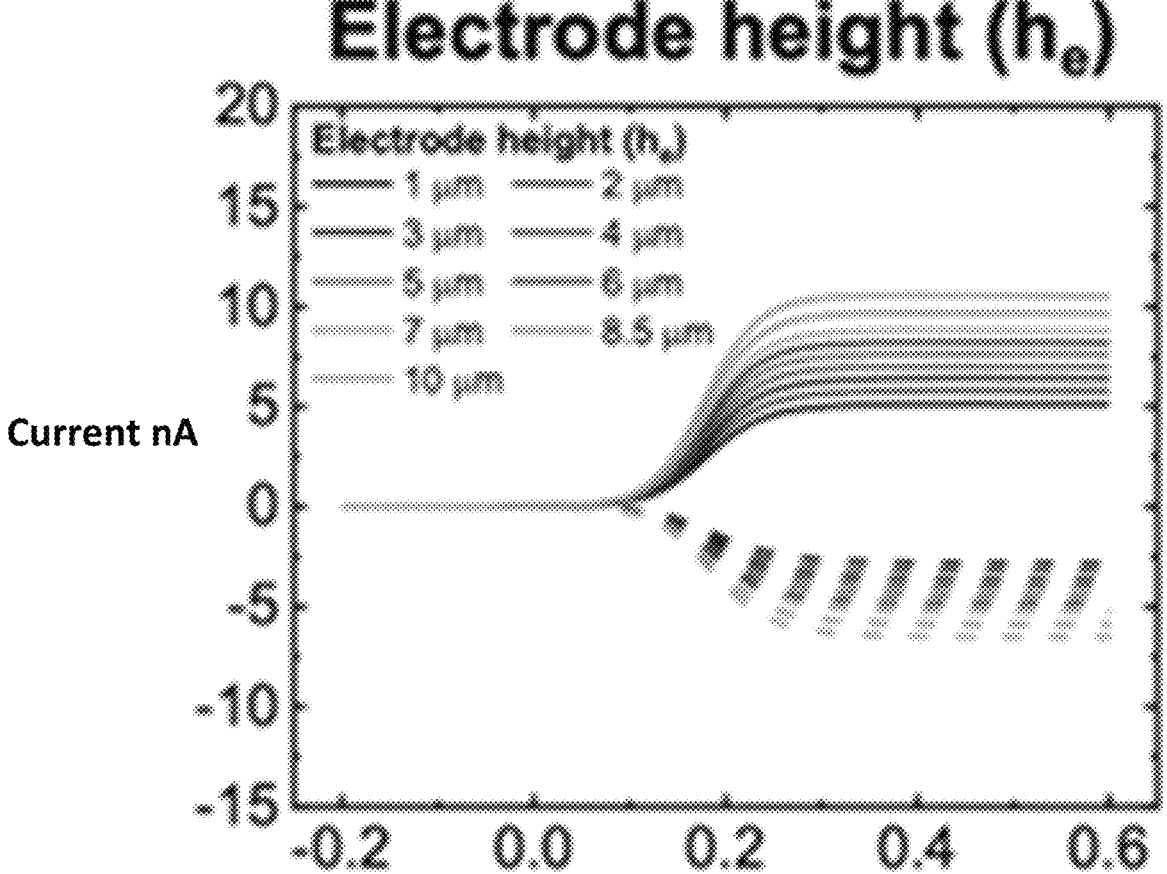
Figure 14:
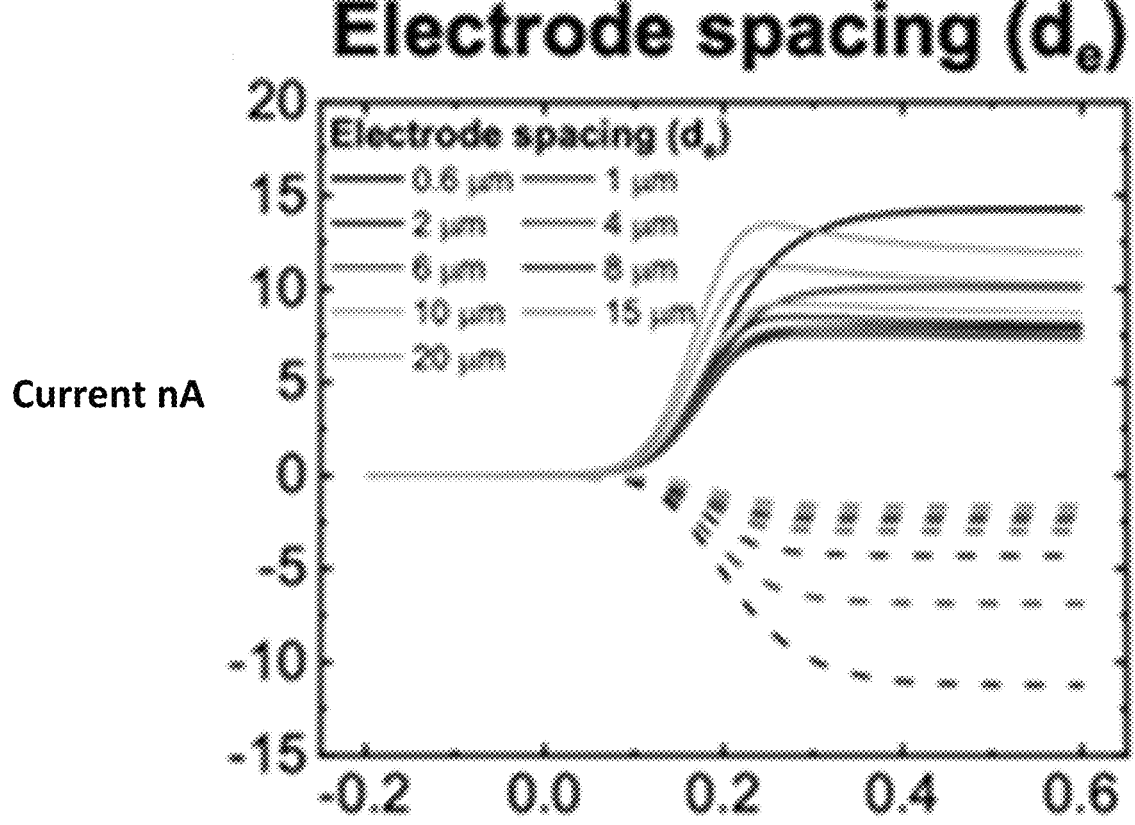
Figure 15:
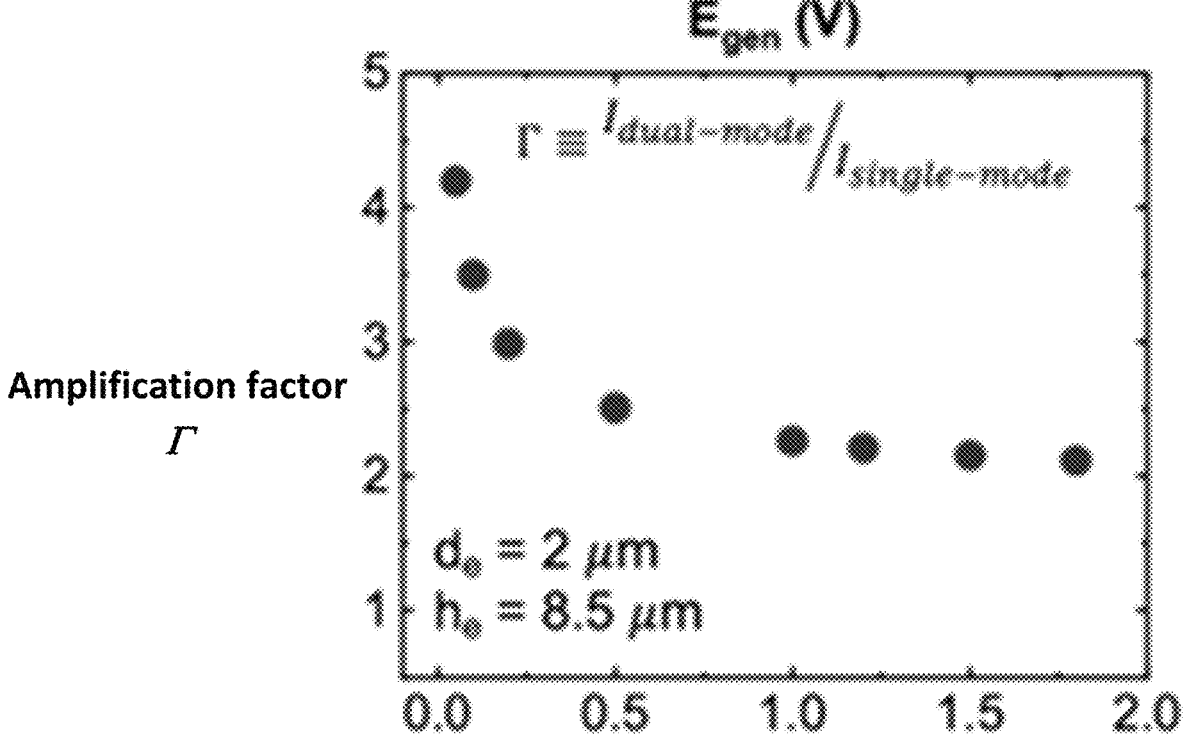
Figure 16:
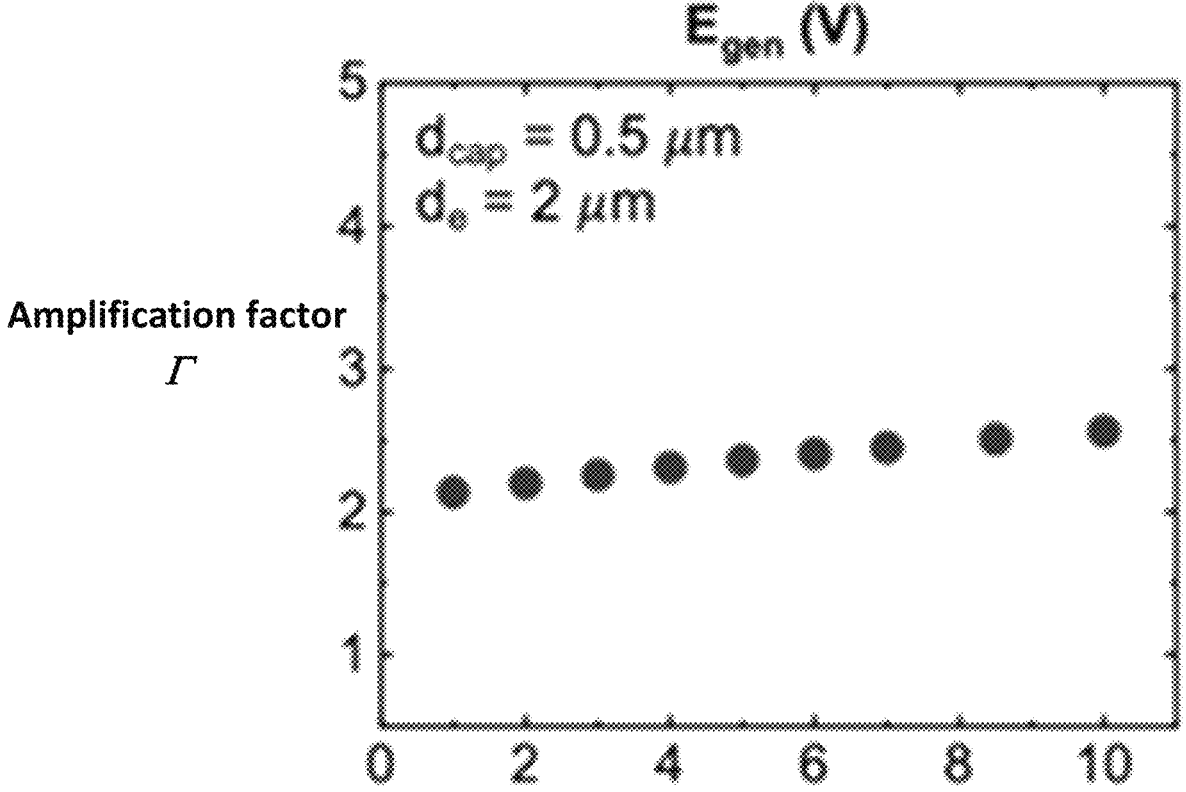
Figure 17:
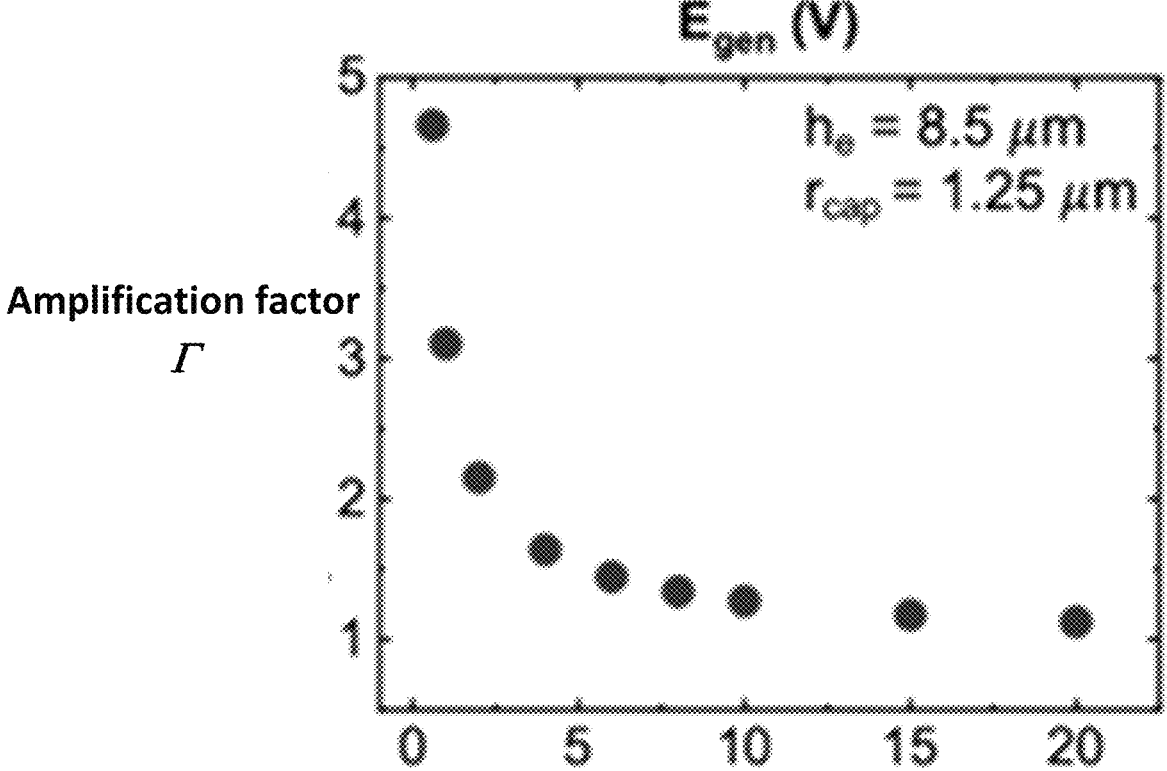
Figure 18:
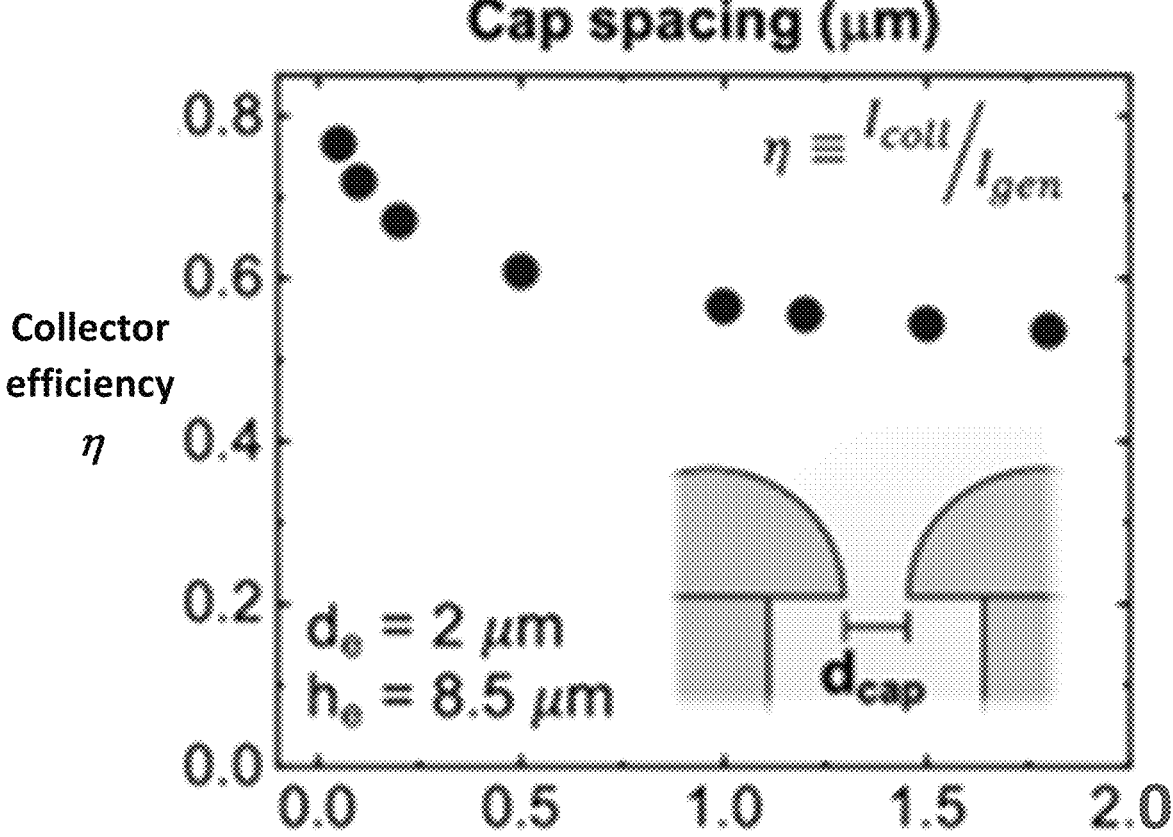
Figure 19:
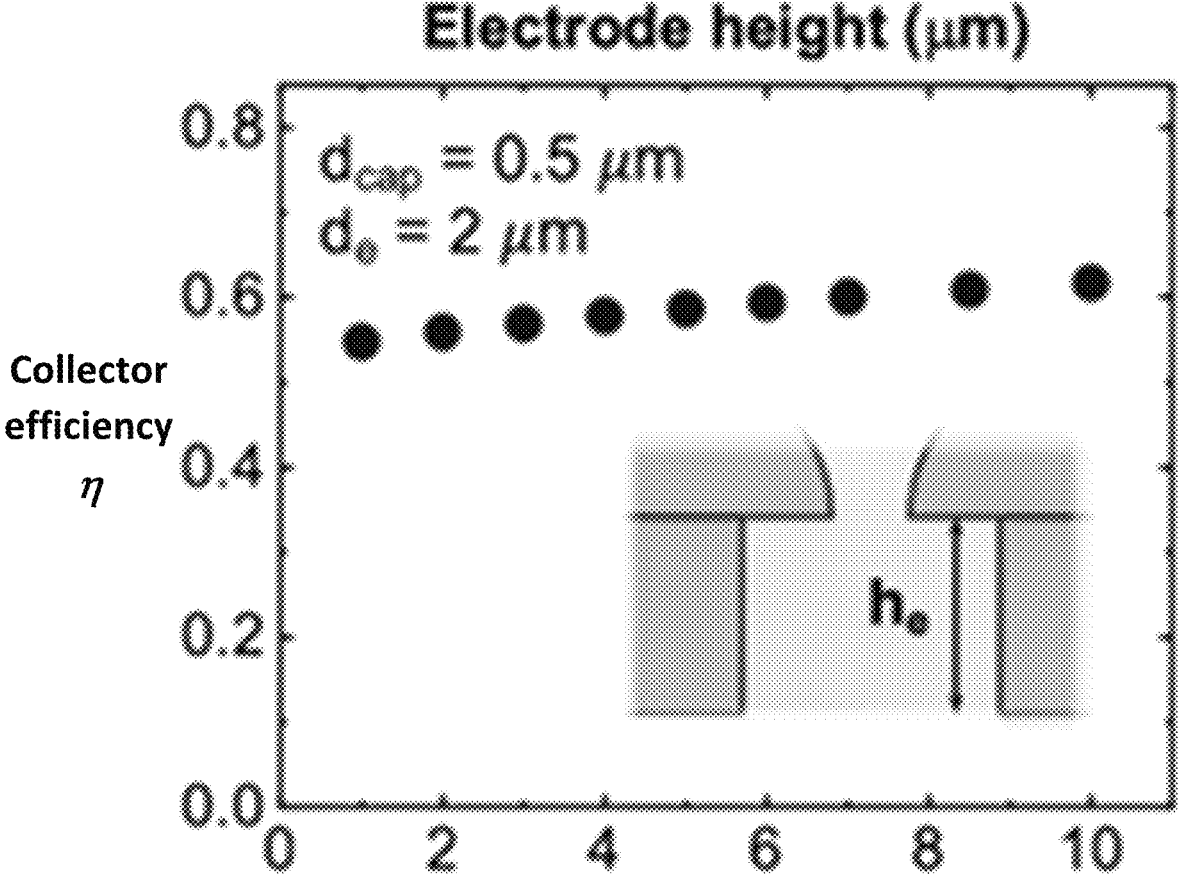
Figure 20:
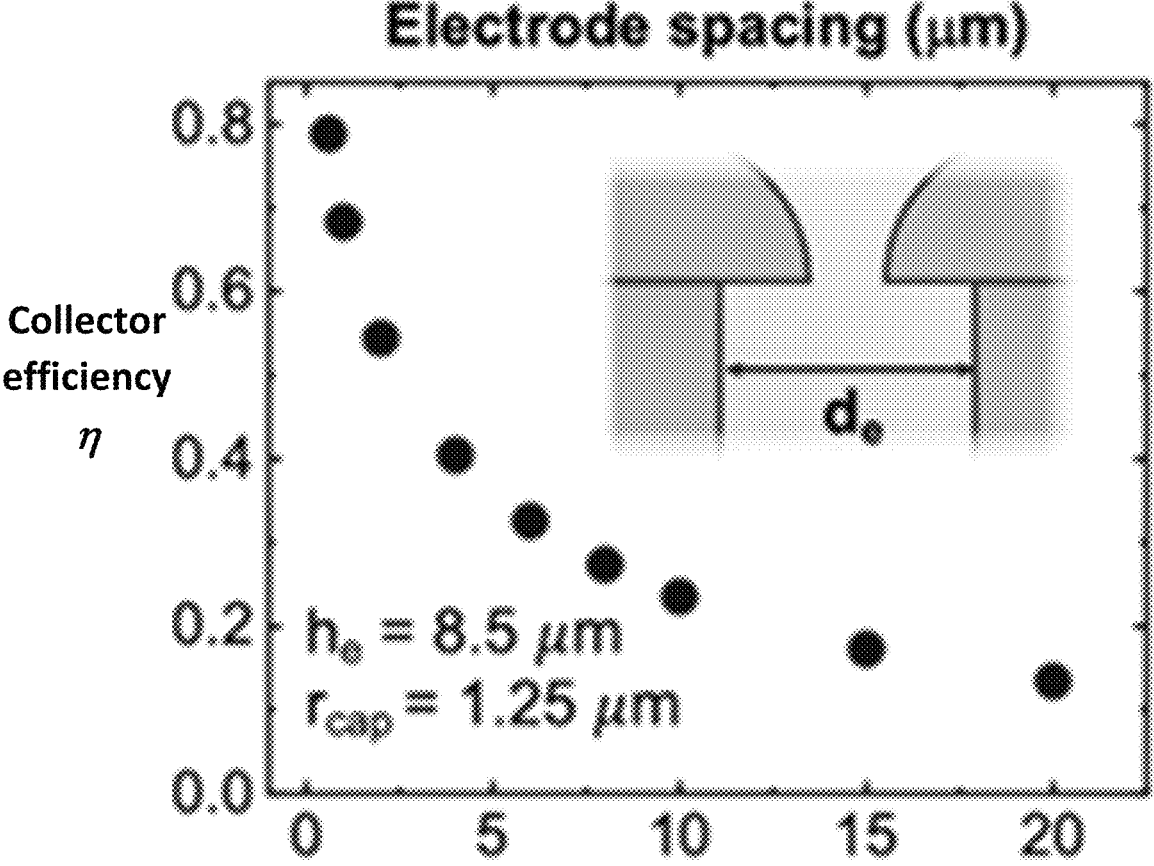

Typically, in electrochemical experiments, a sufficiently conductive electrolyte is used to minimize the ohmic drop in solution. FIG. 10 demonstrates the effect of KCl electrolyte concentration on the voltammetric current and shows the effect of the KCl electrolyte concentration on the electrochemical response of the generator-collector ring-disk geometry. The solid lines represent the generator current while the dashed lines are the corresponding collector current. Parameters: 1 mM $[Fe(CN)_6]^{4-}$, $E_{coll}=\sim 0.15$ V, scan rate=50 mV s$^{-1}$, $d_{cap}=0.5$ µm, $d_e=2$ µm, $h_e=8.5$ µm. As the KCl concentration increases, the steady-state current magnitude slightly decreases. This may be due to less migrative transport of the charged redox probe as electrolyte concentration increases. As a result, at lower KCl concentration, a larger portion of the current-carrying ions will be $[Fe(CN)_6]^{3-/4-}$ rather than K$^+$ and Cl$^-$. The lower electrolyte concentration also supports a larger electric field, which can be advantageous for the electrophoretic transport of the virus particles. Moreover, because Joule heating of the electrolyte scales with conductivity $\sigma_m(Q\propto\sigma_m$, where Q represents the heat generated), it is advantageous to use a lower conductivity electrolyte to minimize these effects. FIG. 11 shows the temperature in the electrolyte after a 1200 s amperometric scan. More specifically, FIG. 11 shows effect of Joule heating after 1200 s during the chronoamperometric scan in the 1 μl droplet configuration. Parameters: 1 mM KCl, 1 mM $[Fe(CN)_6]^{4-}$, $E_{gen}$=0.6 V, $E_{coll}$=−0.15 V, $d_{cap}$=0.5 μm, $d_e$=2 μm, $h_e$=8.5 μm. Only minor temperature differences of a few mK are seen in the immediate region surrounding the electrode, which are not likely to cause any significant degradation in operational performance.

FIGS. 12-20 highlight the effects of electrode geometry, which plays an important role in determining the redox cycling capabilities. More specifically, the figures show generator-collector geometry on the redox cycling characteristics, wherein FIGS. 12-14 relate to the linear sweep voltammograms (Parameters: 1 mM $[Fe(CN)_6]^{4-}$, 1 mm KCl, scan rate=50 m V $s^{-1}$, $E_{coll}$=−0.15 V) demonstrating the effect of cap spacing ($d_{cap}$), electrode height ($h_e$), and electrode spacing ($d_e$), respectively, wherein FIGS. 15-17 relate to the subsequent amplification factors (Γ), and wherein FIGS. 18-20 relate to collector efficiencies (η) as functions of electrode geometry. The impact of cap spacing ($d_{cap}$), electrode height ($h_e$), and electrode spacing ($d_e$) are evaluated. Regarding the cap spacing, the amplification factor Γ ranges from ~4.2 at $d_{cap}$=0.05 μm down to ~2.05 for $d_{cap}$=1.8 μm, the largest spacing studied. Likewise, the collector efficiency ($η=I_{coll}/I_{gen}$) follows a similar trend, ranging from 0.78 for $d_{cap}$=0.05 μm down to 0.55 for $d_{cap}$=1.8 μm. Although a smaller $d_{cap}$ leads to improved redox cycling behavior, decreasing $d_{cap}$ beyond a few 100 nm could be difficult to control during the overgrowth electrodeposition. To improve process robustness and consistency, spacings of 0.1 μm and above may be more suitable for experimental realization of the proposed system from technical standpoint.

Figure 21:
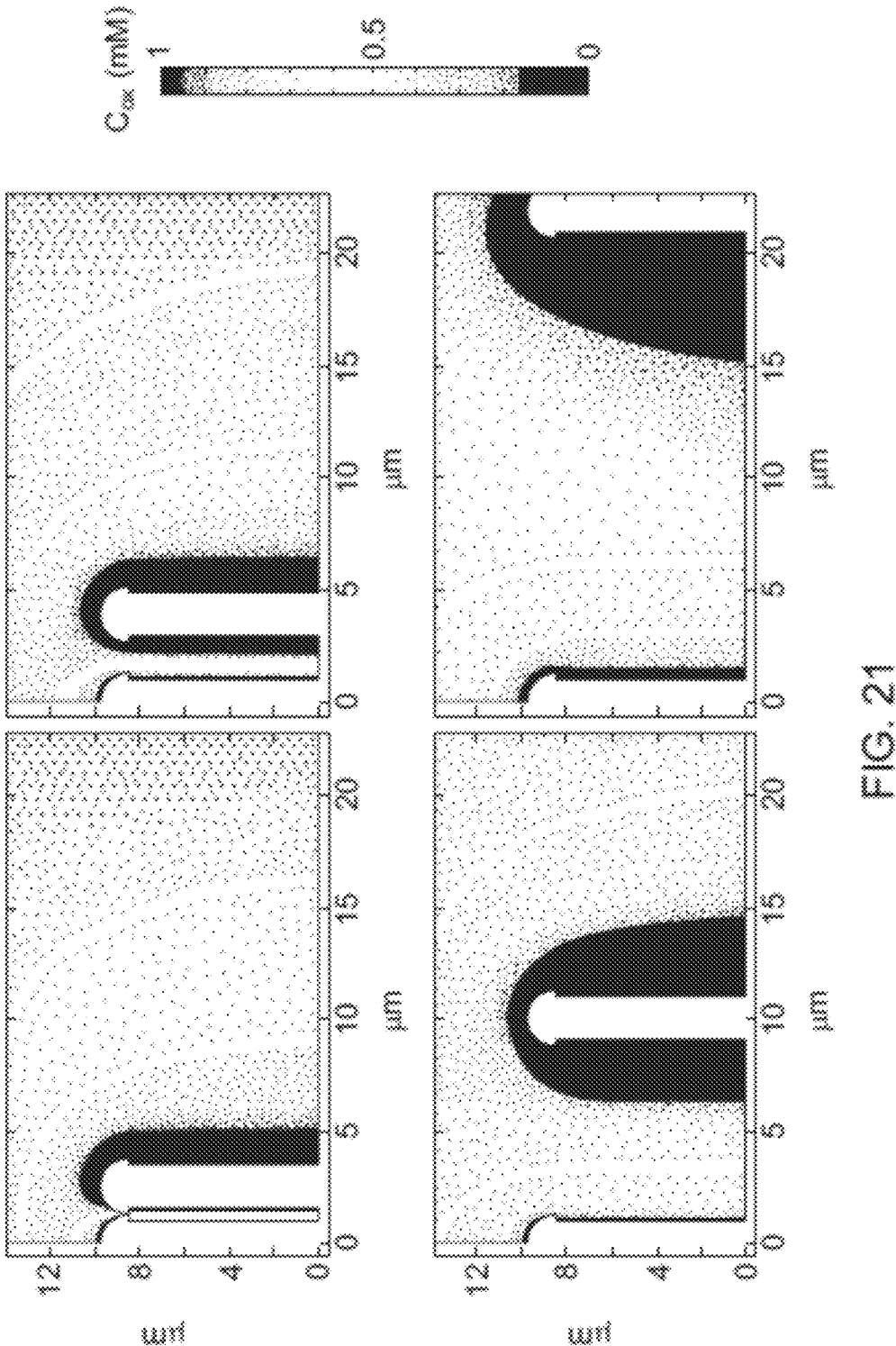
FIG. 21 shows concentration profiles of $c_{ox}$ at $E_{gen}$=0.6 V for varying electrode spacings demonstrating how the overlap in diffusion layers changes as the electrode spacing increases.

More substantial differences in η and Γ are seen when varying the electrode spacing $d_e$. For $d_e$=20 μm, F is less than 1.2 and n~0.13, whereas decreasing $d_e$ to 0.6 μm increases Γ nearly four-fold to ~4.8 and η to ~0.8. Interestingly, around $d_e$=8 μm and larger, the cycling between collector and generator is minimized due to decreased overlap in diffusion layers (see FIG. 21). FIG. 21 shows concentration profiles of $c_{ox}$ at $E_{gen}$=0.6 V for varying electrode spacings demonstrating how the overlap in diffusion layers changes as the electrode spacing increases. Parameters: 1 mM KCl, 1 mM $[Fe(CN)_6]^{4-}$, $E_{coll}$=−0.15 V, scan rate=50 m V $s^{-1}$, $r_{cap}$=1.25 μm, $h_e$=8.5 μm. This is evident by the onset of an oxidation peak in the LSV data seen at 8 μm, and especially at 15 and 20 μm, as opposed to the steady-state sigmoidal behavior typically seen with microelectrodes.

Figure 22:
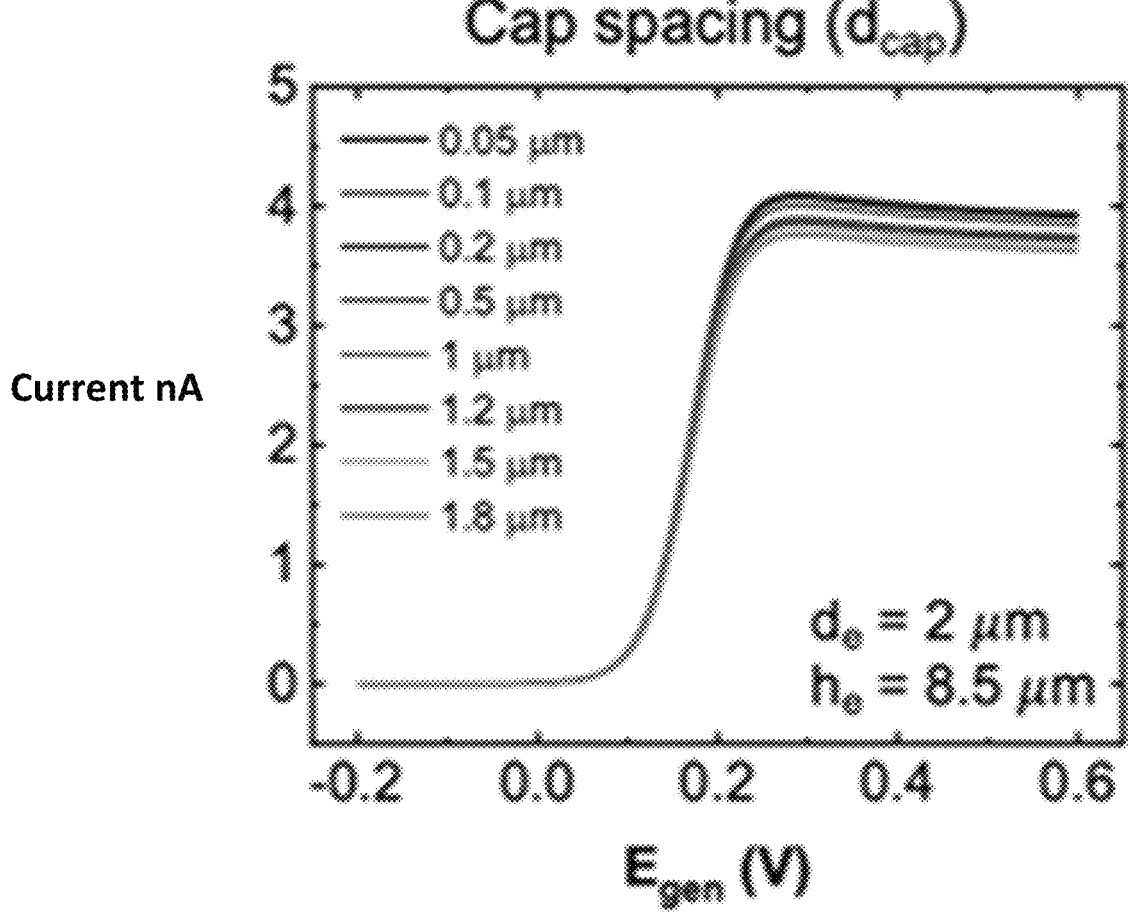
FIG. 22 shows the effect of cap spacing ($d_{cap}$)
Figure 23:
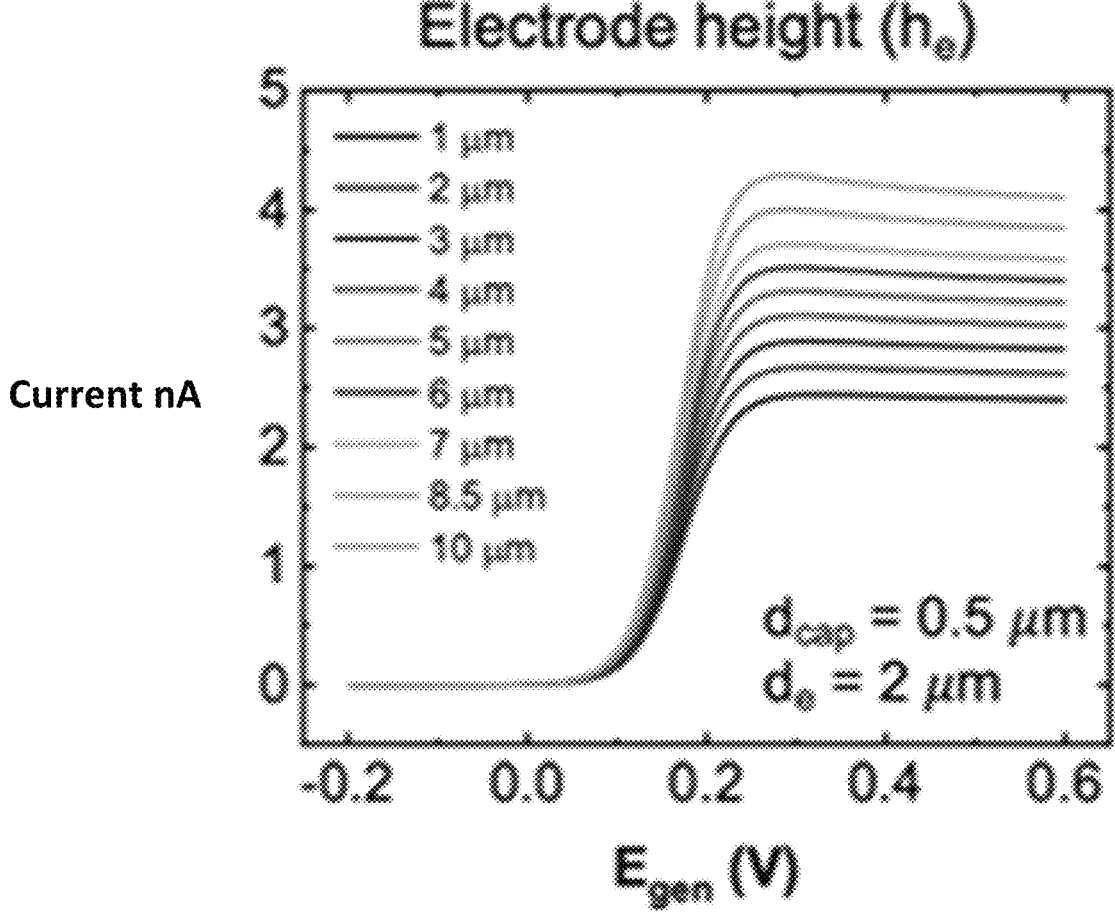
FIG. 23 shows the effect of electrode height ($h_e$)
Figure 24:
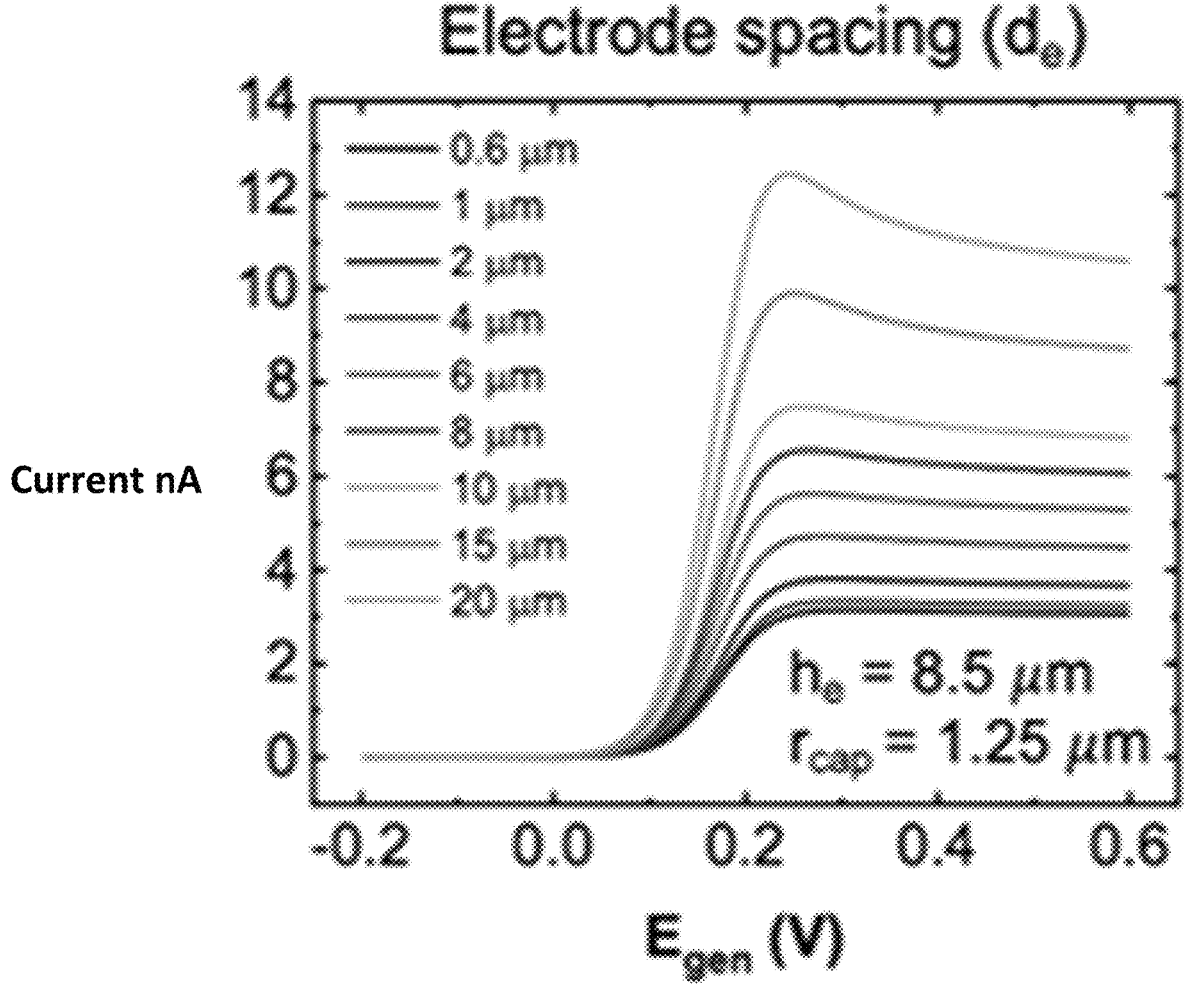
FIG. 24 shows the effect of electrode spacing ($d_e$) in the single-mode configuration.

This points to mass transfer limitations similar to those seen with macroelectrodes. The onset of an oxidation peak can also be seen in the single-mode configurations presented in FIGS. 22-24, thus signifying the importance of redox cycling in maintaining steady-state conditions and minimizing depletion of the redox species. FIG. 22 shows the effect of cap spacing ($d_{cap}$), FIG. 23 shows the effect of electrode height ($h_e$), and FIG. 24 shows the effect of electrode spacing ($d_e$) in the single-mode configuration. The parameters for FIGS. 22-24 are: 1 mM KCl, 1 mM $[Fe(CN)_6]^{4-}$, scan rate=50 mV $s^{-1}$, $E_{coll}$=floating. To ensure adequate amplification and collection is upheld, an electrode spacing of 2 μm or less is recommended.

The electrode height ($h_e$) does have implications on η and Γ, albeit much less of an impact than $d_e$. Across the range of $h_e$ from 1-10 μm studied in this work, Γ only varies from ~2.1 to 2.6 with the collector efficiency following a similar trend. However, this may be advantageous as increasing the height beyond 10 μm could present fabrication challenges associated with thickness of photoresist (e.g., electrodeposition mold layer). With the above factors taken into consideration, in addition to potential challenges that could occur during the device fabrication process, a generator-collector electrode spacing of $d_e$=2 μm, electrode height of $h_e$=8.5 μm, and cap spacing of $d_{cap}$=0.5 μm is used for subsequent simulations.

Electrochemical Analysis in the Presence of Virus Particles (Droplet Configuration)

After evaluating the electrochemical properties of the microelectrodes, virus particles were introduced into the simulation to better understand the detection capability of the proposed system. The virus particles are modelled as spherical core-shell structure, each layer having unique dielectric properties. Typically, the outer shell has a dielectric constant on the order of $ε_2$=5-10 while the $ε_1$ is around 70-80. Of particular interest for electrophoretic transport are the virus charge (q), virus count (N), and virus size ($d_p$). Some reports have estimated the net surface charge of different viruses, such as Cowpea Mosaic Virus (CPMV), which is estimated to have a charge of (negative) 200e (where e is the elementary unit of charge) per virion (or 0.013 C $m^{-2}$). Similarly, for Cowpea Chlorotic Mottle Virus (CCMV), a surface charge of (negative) 150e-200e is estimated based on electrophoretic mobility ($μ_{EP}$) data at neutral pH. For Tobacco Mosaic Virus (TMV) the surface charge density is even higher, at 0.043 C $m^{-2}$. The charged nature of the virus particles serves as the basis for electrophoretic enrichment.

Figure 25:
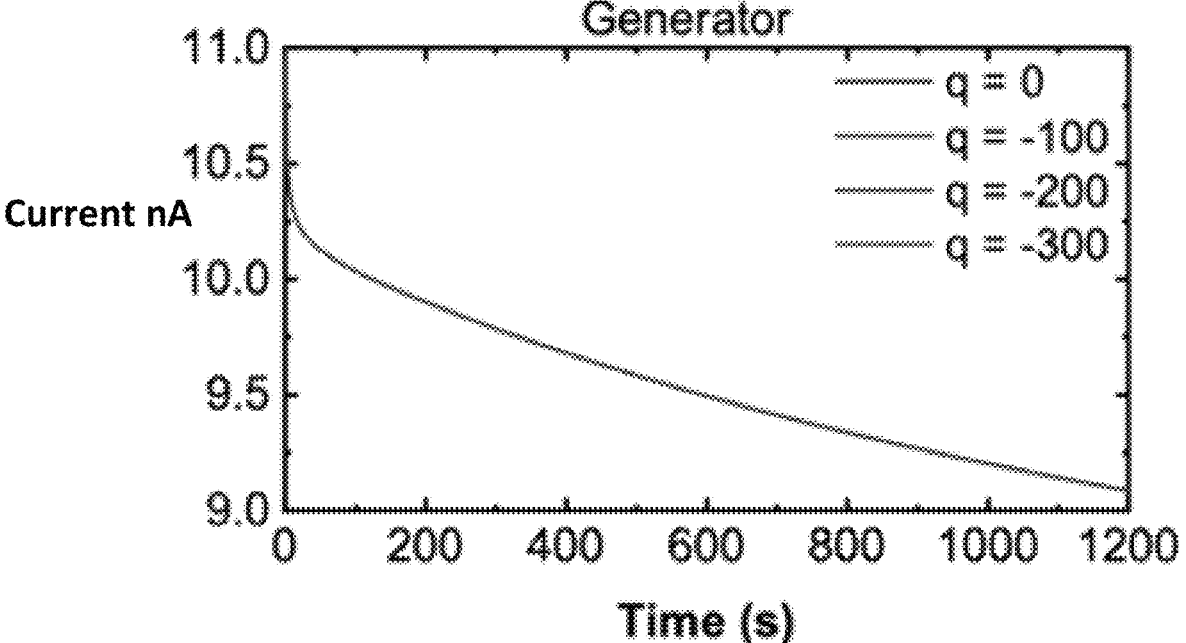
Figure 26:
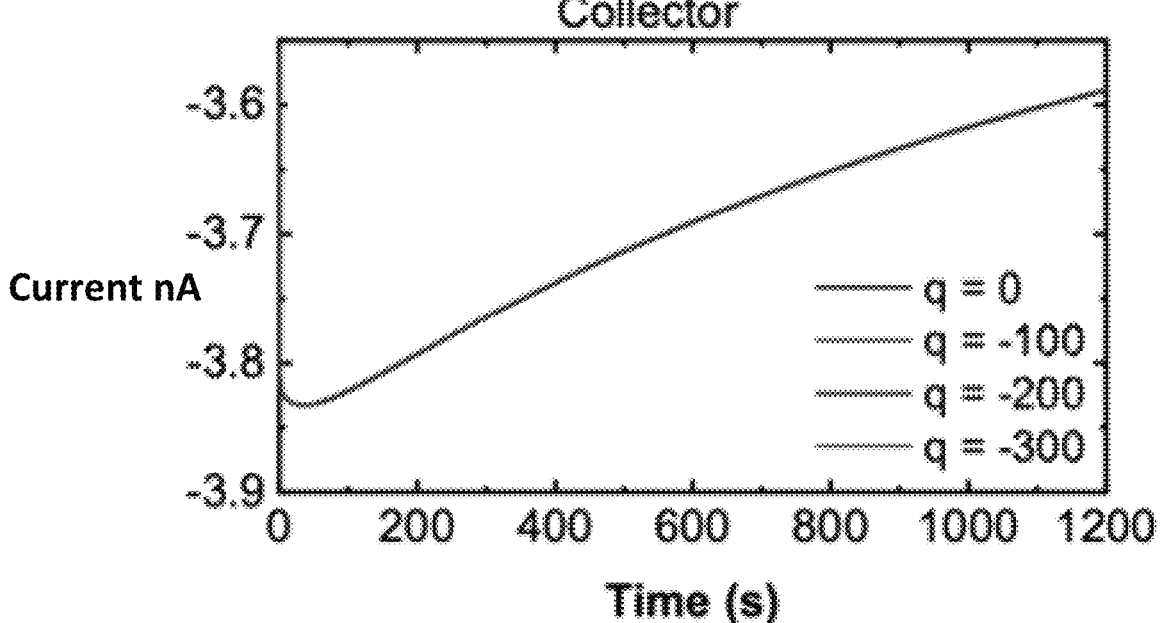
Figure 27:
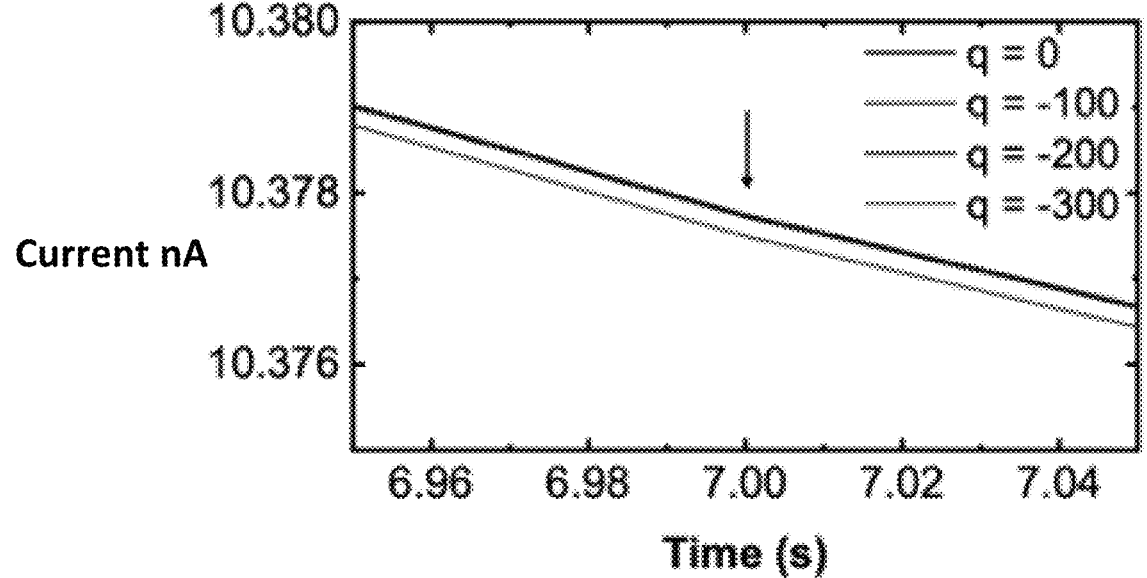
Figure 28:
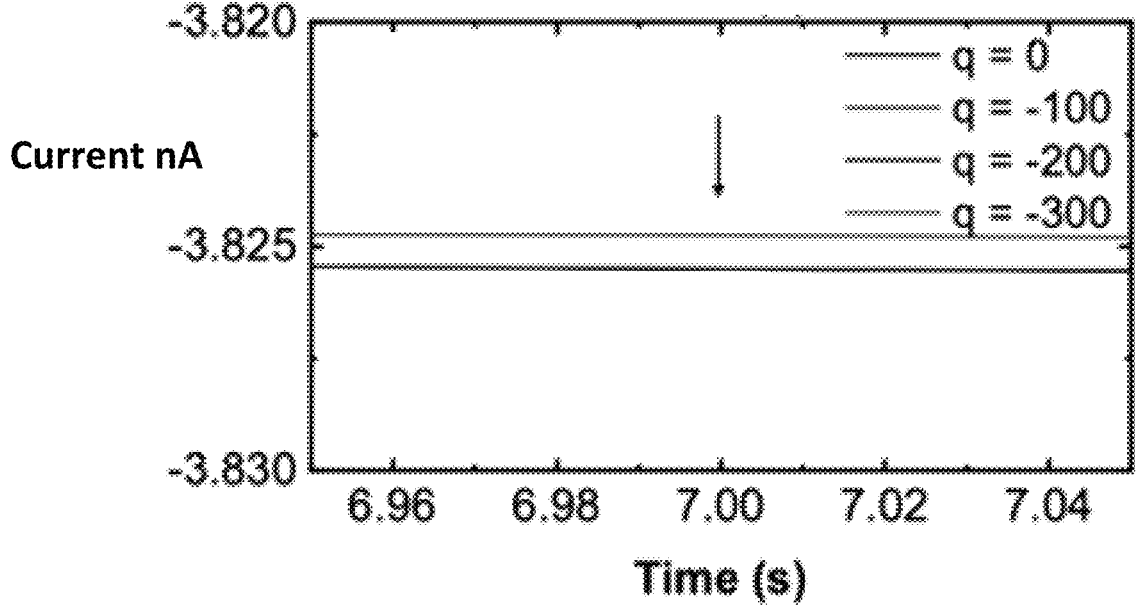
Figure 29:
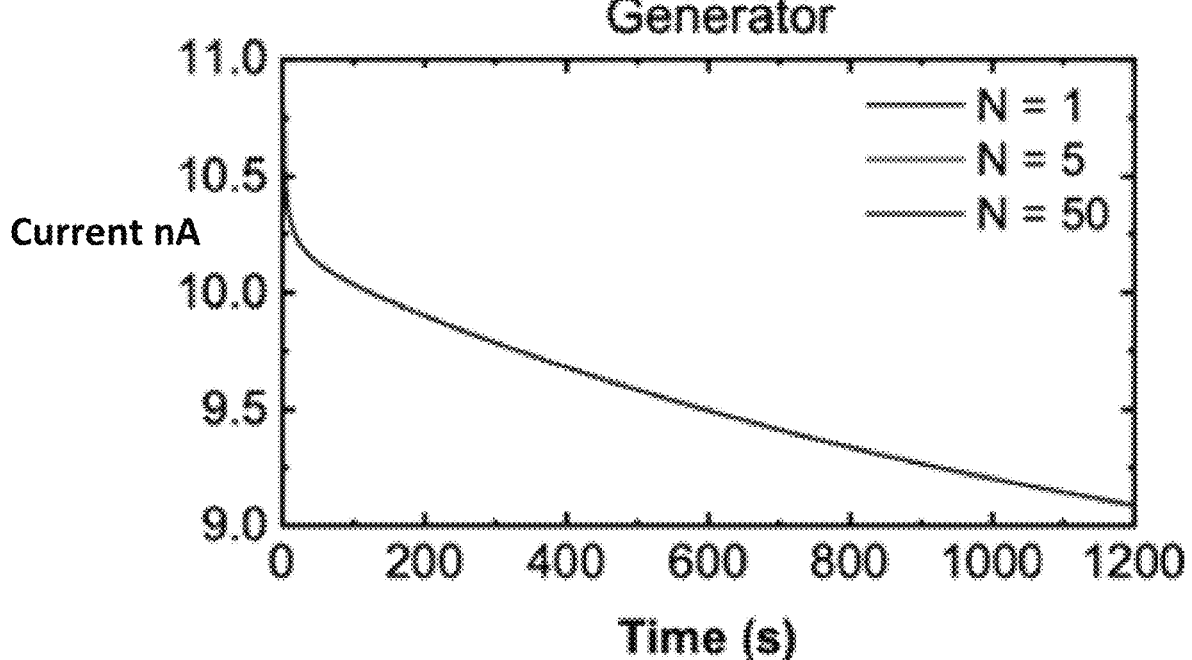
Figure 30:
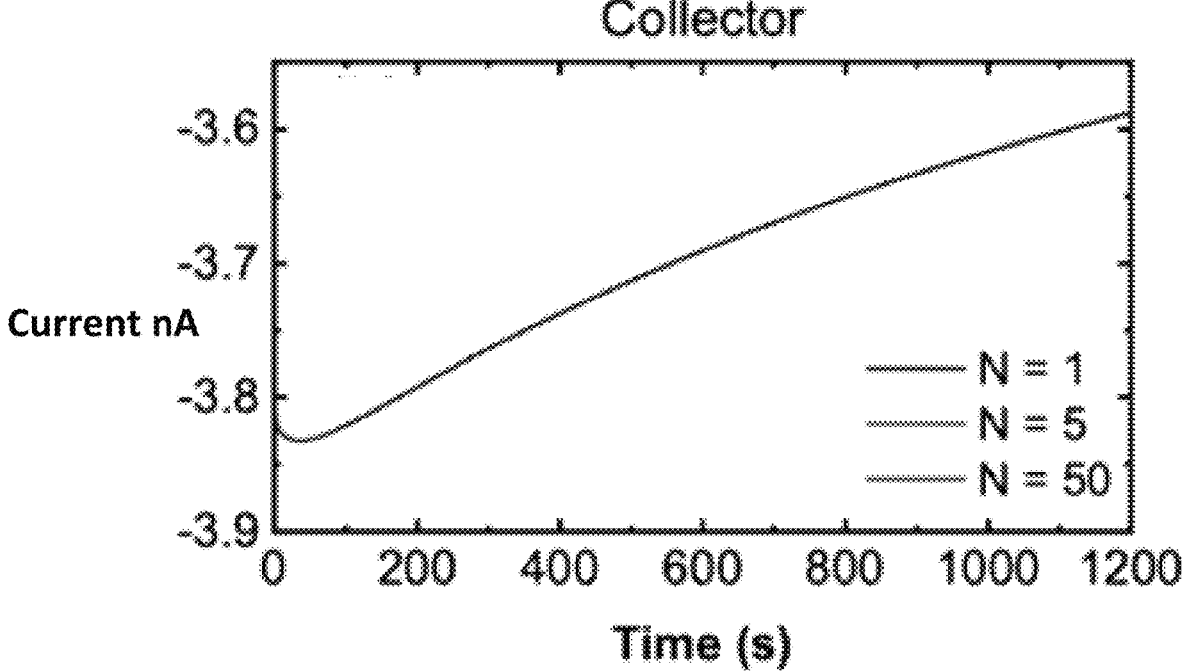
Figure 31:
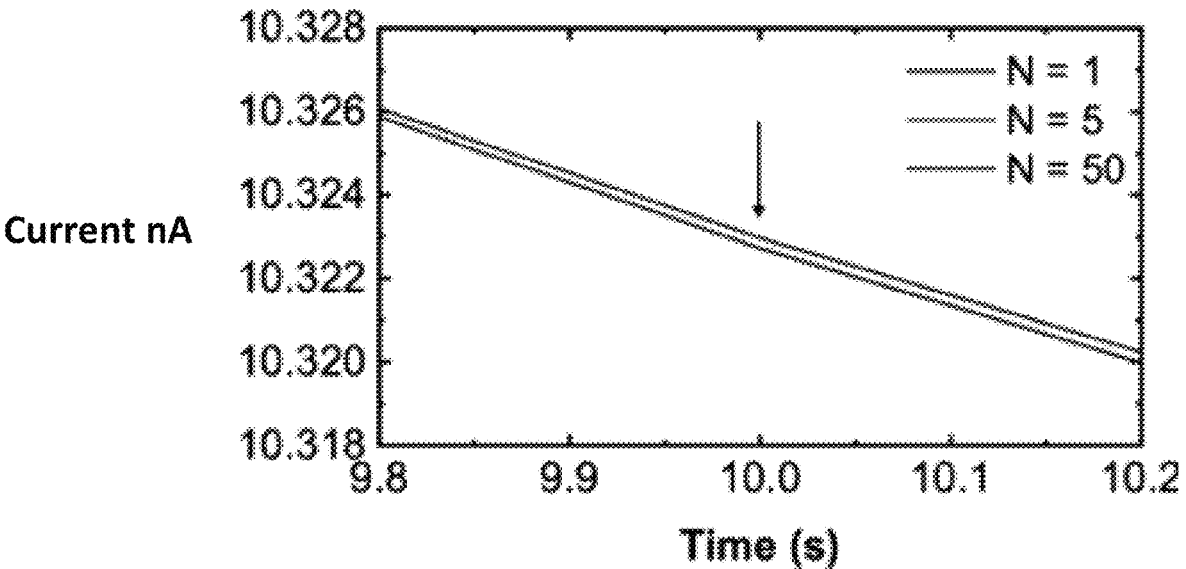
Figure 32:
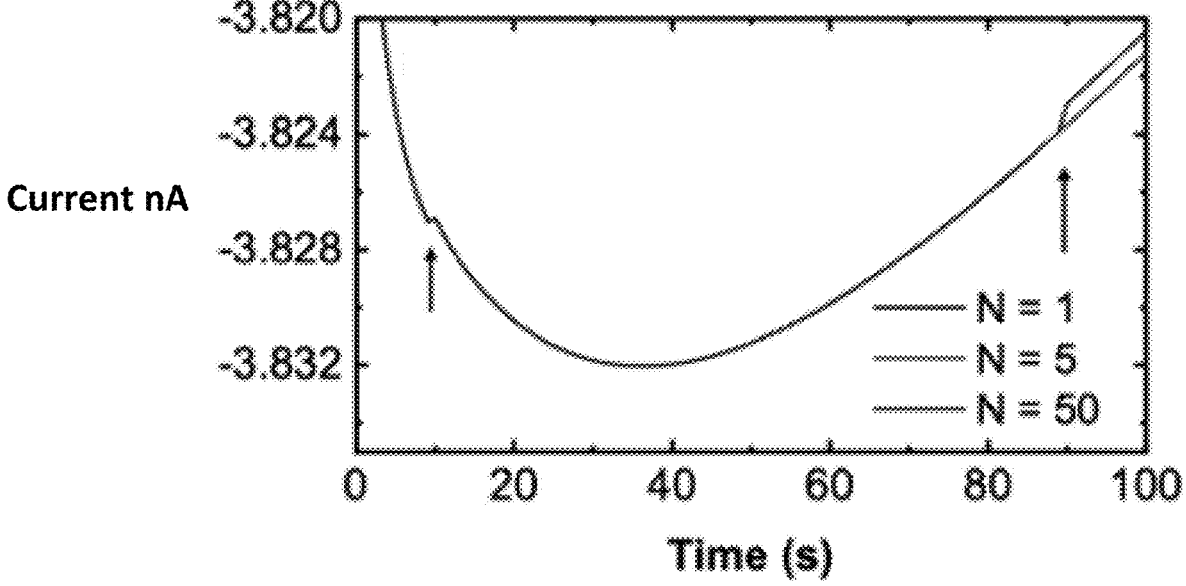
Figure 33:
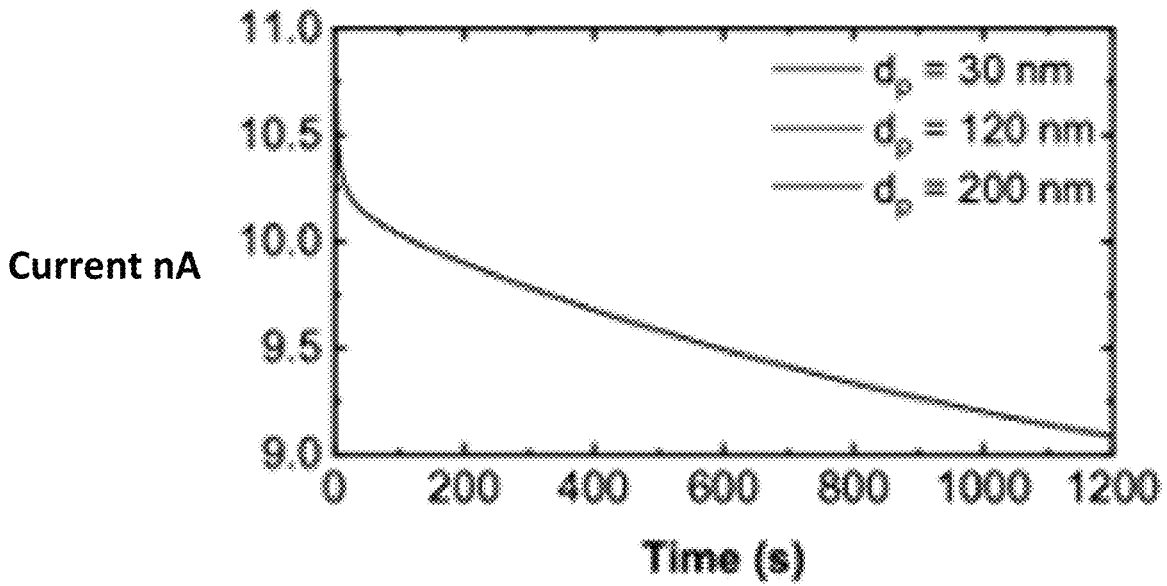
Figure 34:
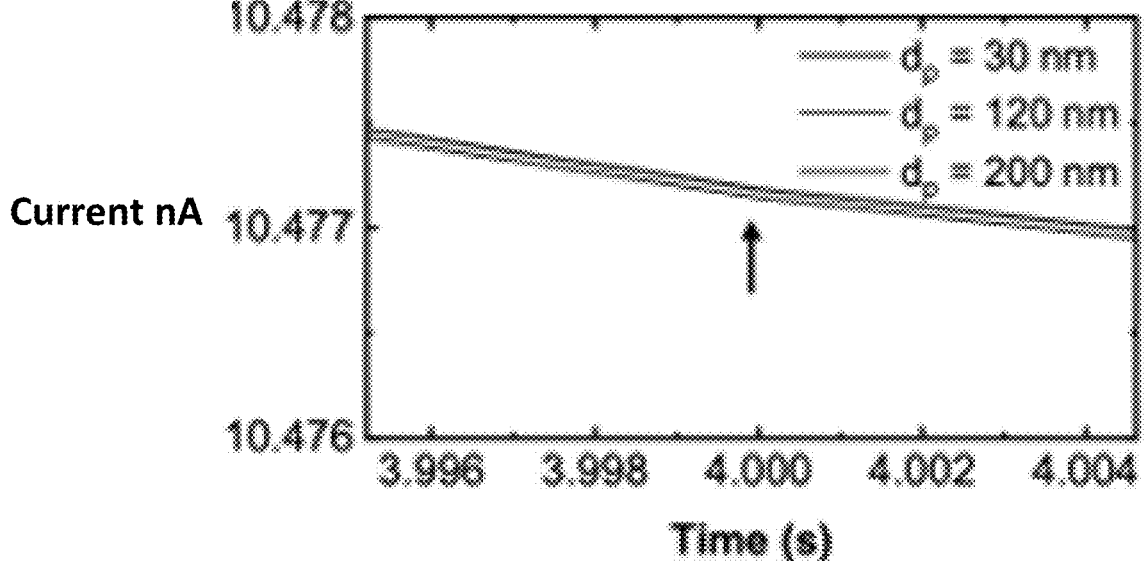
Figure 35:
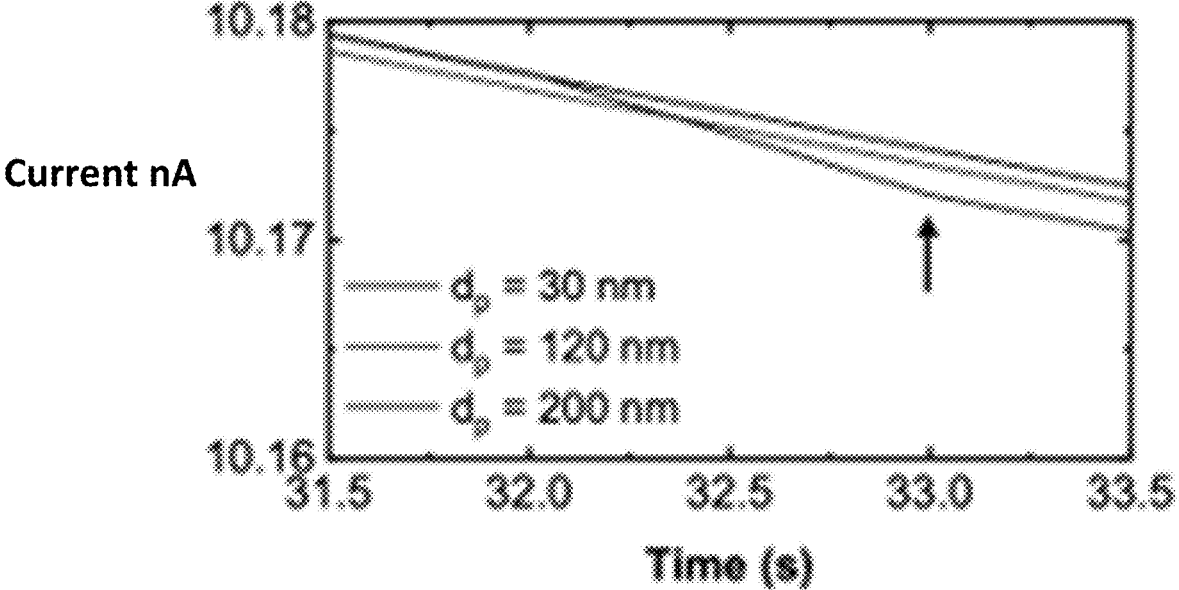
Figure 36:
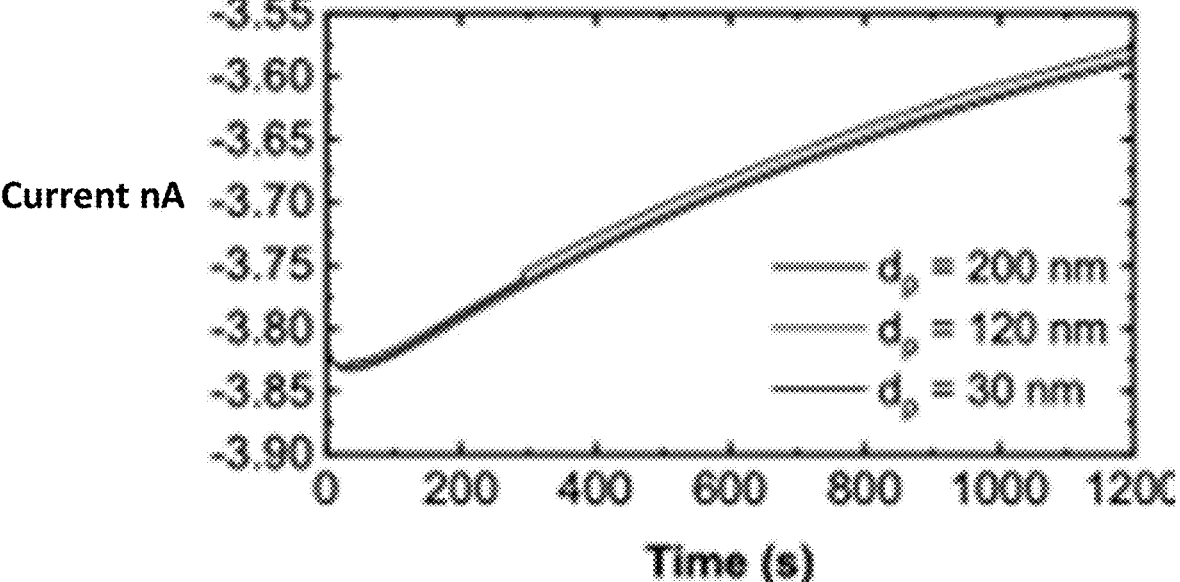
Figure 37:
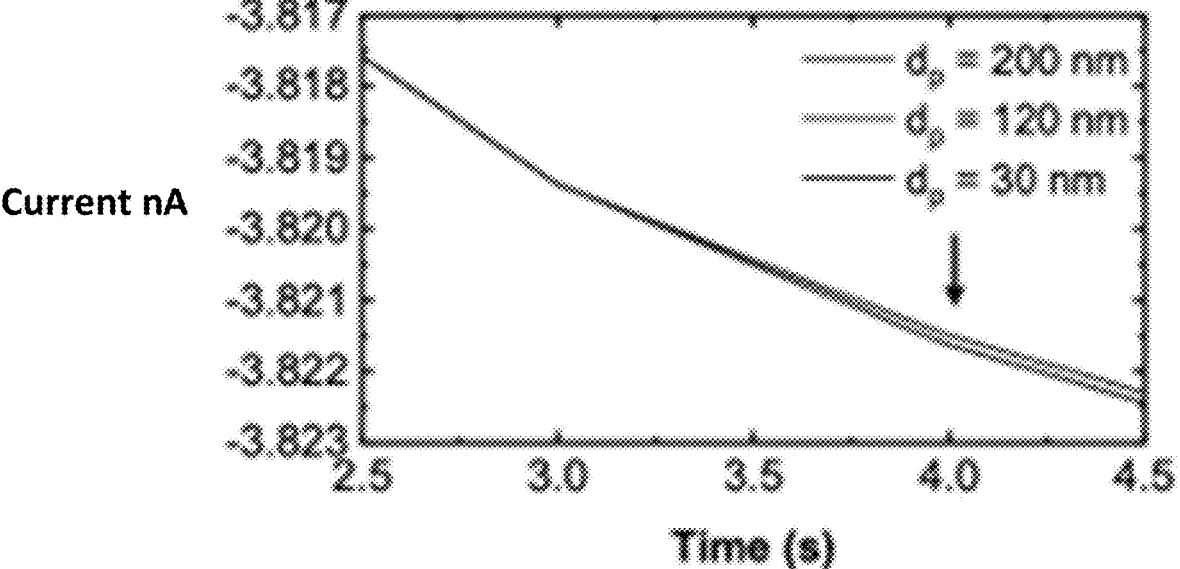
Figure 38:
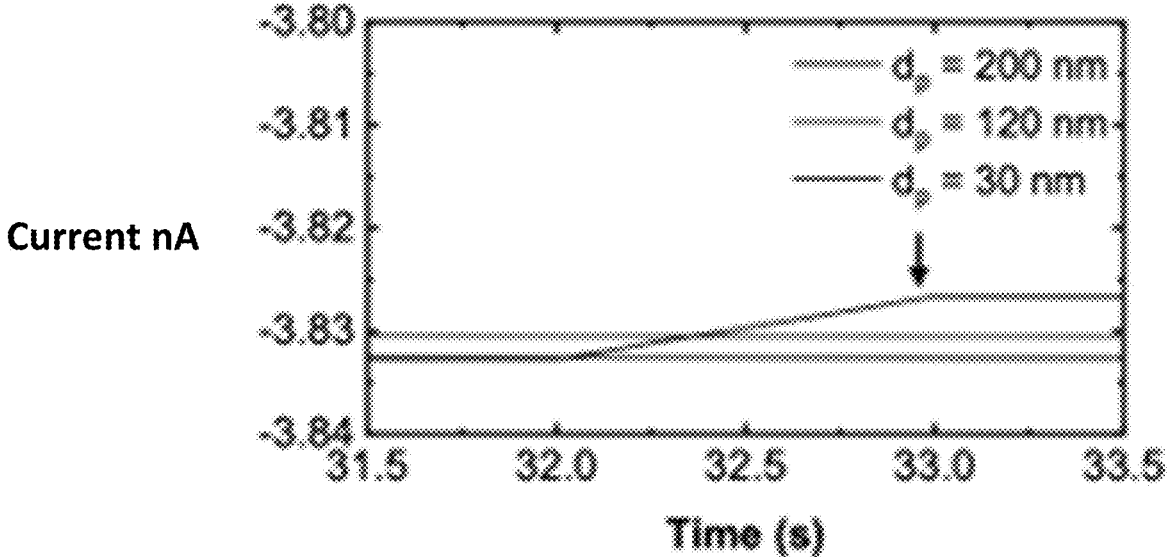

The chronoamperometric response (see FIGS. 25-38) is simulated for unprocessed amperometric data) with four different particle charges −0, −100, −200, and −300 (in units of e) —and three particle sizes −30, 120, and 200 nm—to better understand how the charge and size of a particle impacts the sensor response, specifically particle capture time and number of capture events. FIGS. 25-28 show raw chronoamperometric scans in the ring-disk 1 μl droplet configuration for varying particle charge, wherein FIG. 25 shows the generator current, FIG. 26 shows the collector current, and FIGS. 27 and 28 show close-up of specific capture events as indicated by the arrows. The parameters for FIGS. 25-28 are: mM KCl, 1 mM $[Fe(CN)_6]^{4-}$, $E_{coll}$=−0.15 V, $E_{gen}$=0.6 V, $d_{cap}$=0.5 μm, $d_e$=2 μm, $h_e$=8.5 μm, N=10, $d_p$=70 nm. FIGS. 29-32 show raw chronoamperometric scans in the ring-disk 1 μl droplet configuration for varying particle number, wherein FIG. 29 shows the generator current, FIG. 30 shows the collector current, and FIGS. 31 and 32 show close-up of specific capture events as indicated by the arrows. The parameters for FIGS. 29-32 are: 1 mM KCl, 1 mM $[Fe(CN)_6]^{4-}$, $E_{coll}$=−0.15 V, $E_{gen}$=0.6 V, $d_{cap}$=0.5 μm, $d_e$=2 μm, $h_e$=8.5 μm, q=−200, $d_p$=70 nm. FIGS. 33-38 show raw chronoamperometric scans in the ring-disk 1 μl droplet configuration for varying particle size, wherein FIG. 33 shows the generator current, FIGS. 34 and 35 show close-ups of individual capture events, FIG. 36 shows the collector current, and FIGS. 37 and 38 show close-ups of individual capture events. The parameters for FIGS. 33-38 are: 1 mM KCl, 1 mM $[Fe(CN)_6]^{4-}$, $E_{coll}$=−0.15 V, $E_{gen}$=0.6 V, $d_{cap}$=0.5 μm, $d_e$=2 μm, $h_e$=8.5 μm, N=10, q=−200.

Figure 39:
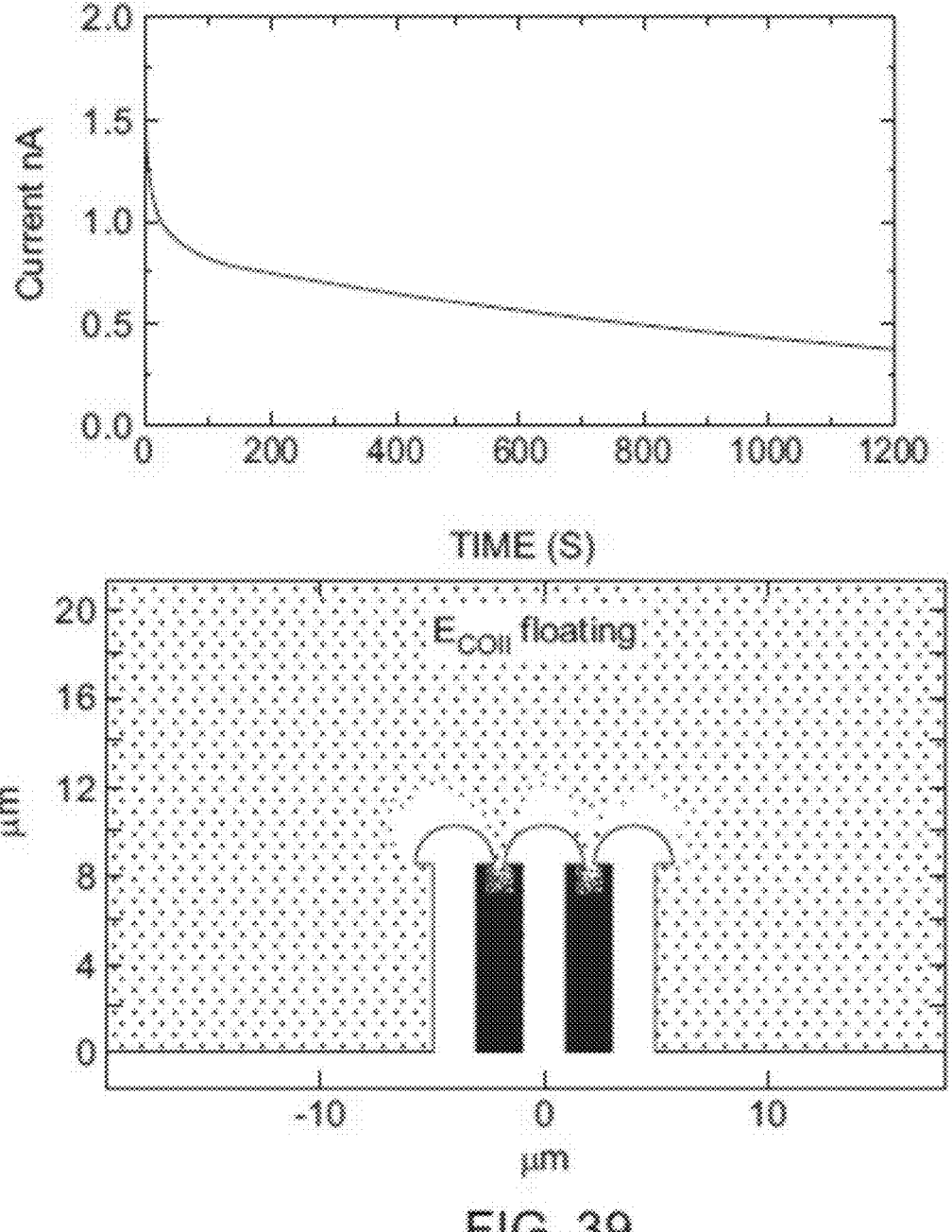
FIG. 39 shows chronoamperometric scan with $E_{coll}$=floating with an exemplary ring-disk 1 μl droplet configuration, and the electric field magnitude with $E_{coll}$=floating.
Figure 40:
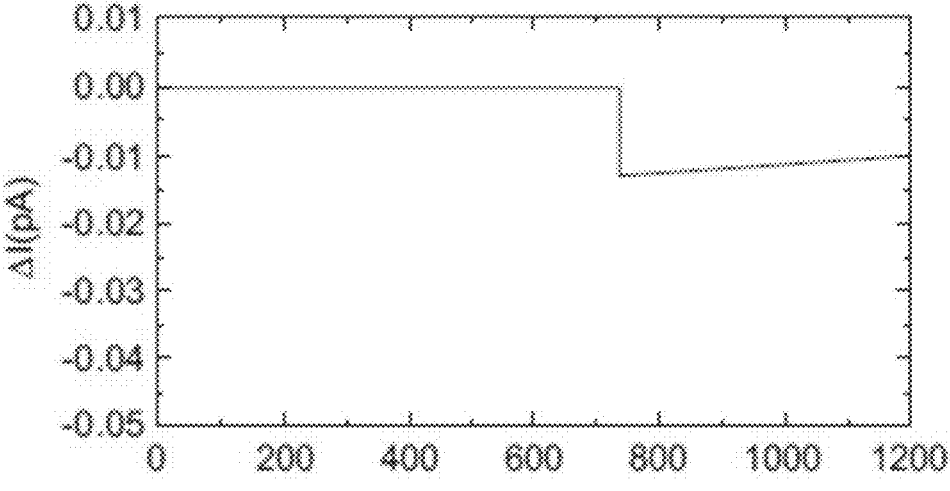
FIG. 40 show the background subtracted current illustrating a step at the instance of virus capture, and the electric field magnitude with $E_{coll}$=–0.15 V.
Figure 40:
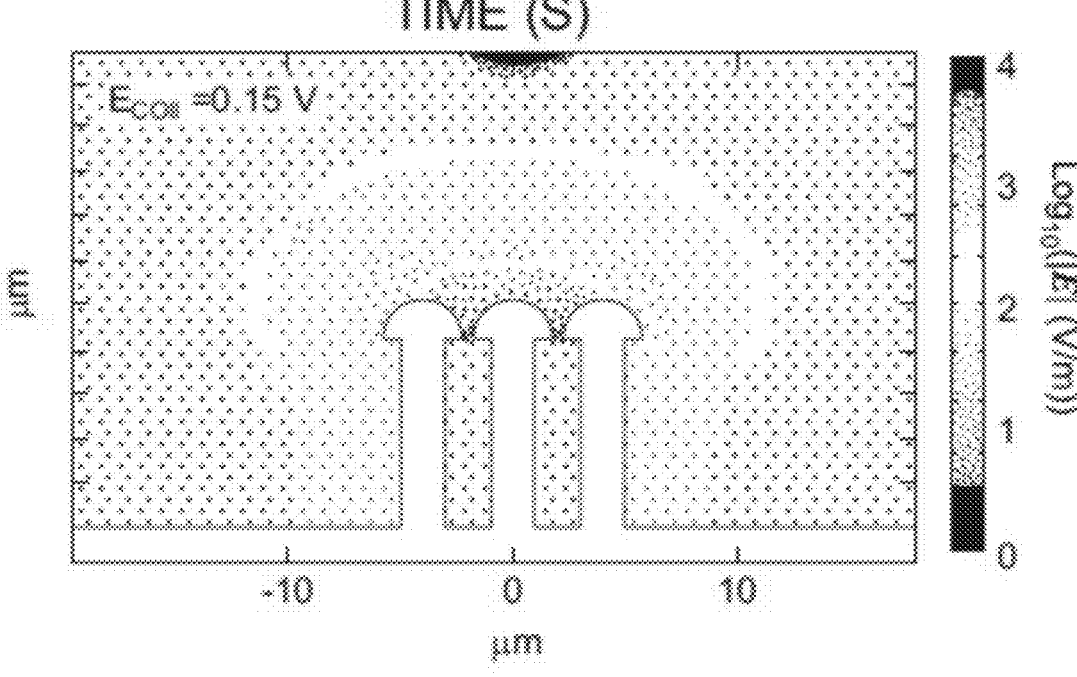

The chronoamperometric simulations are performed in dual-mode configuration with $E_{coll}$=−0.15 V and $E_{gen}$=0.6 V, which significantly reduces the virus capture time (~740 s to ~20 s), due to a stronger electric field, and results in larger current steps (~0.265 pA vs. 0.013 pA), due to the larger amplified current compared to single-mode (see FIGS. 39 and 40) for results of simulations done in single-mode). FIG. 39 shows a chronoamperometric scan with $E_{coll}$=floating with the ring-disk 1 μl droplet configuration, and the electric field magnitude with $E_{coll}$=floating. FIG. 40 show the background subtracted current illustrating a step at the instance of virus capture, and the electric field magnitude with $E_{coll}$=−0.15 V. For FIGS. 39 and 40 the parameters are: 1 mM KCl, 1 mM [Fe(CN)$_6$]$^{4-}$, $E_{coll}$=floating, $E_{gen}$=0.6 V, $d_{cap}$=0.5 μm, $d_e$=2 μm, $h_e$=8.5 μm, $d_p$=70 nm, N=10, q=−200.

Figure 41:
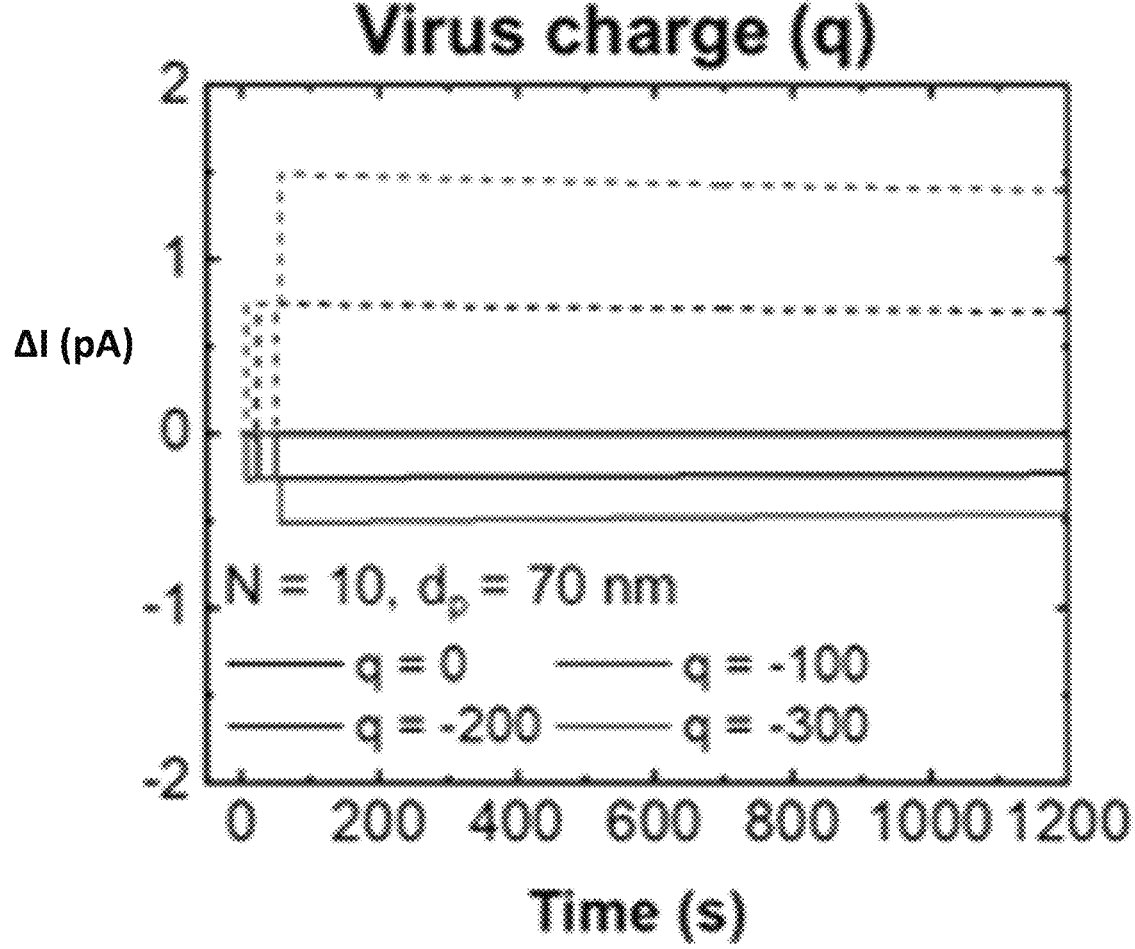
Figure 42:
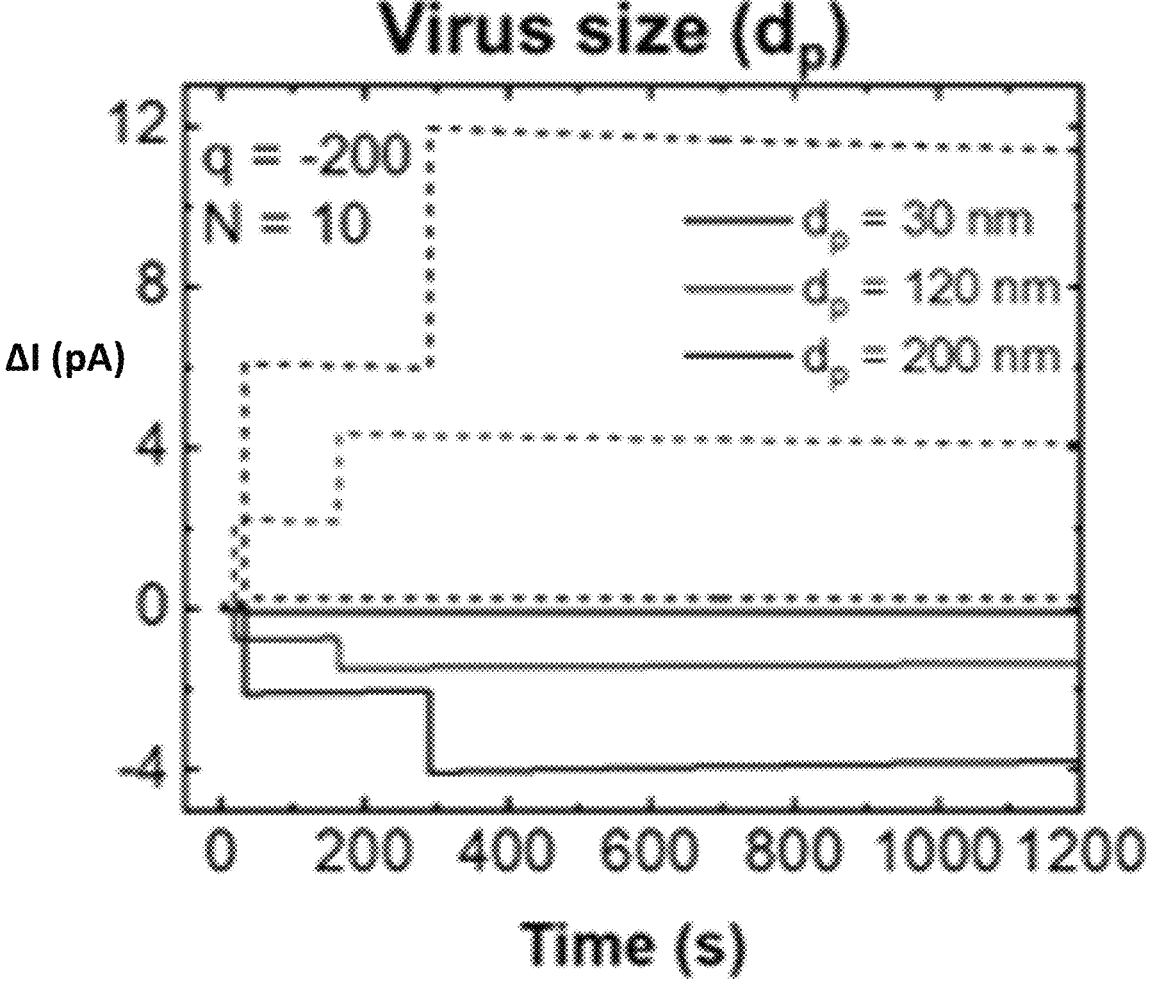
Figure 43:
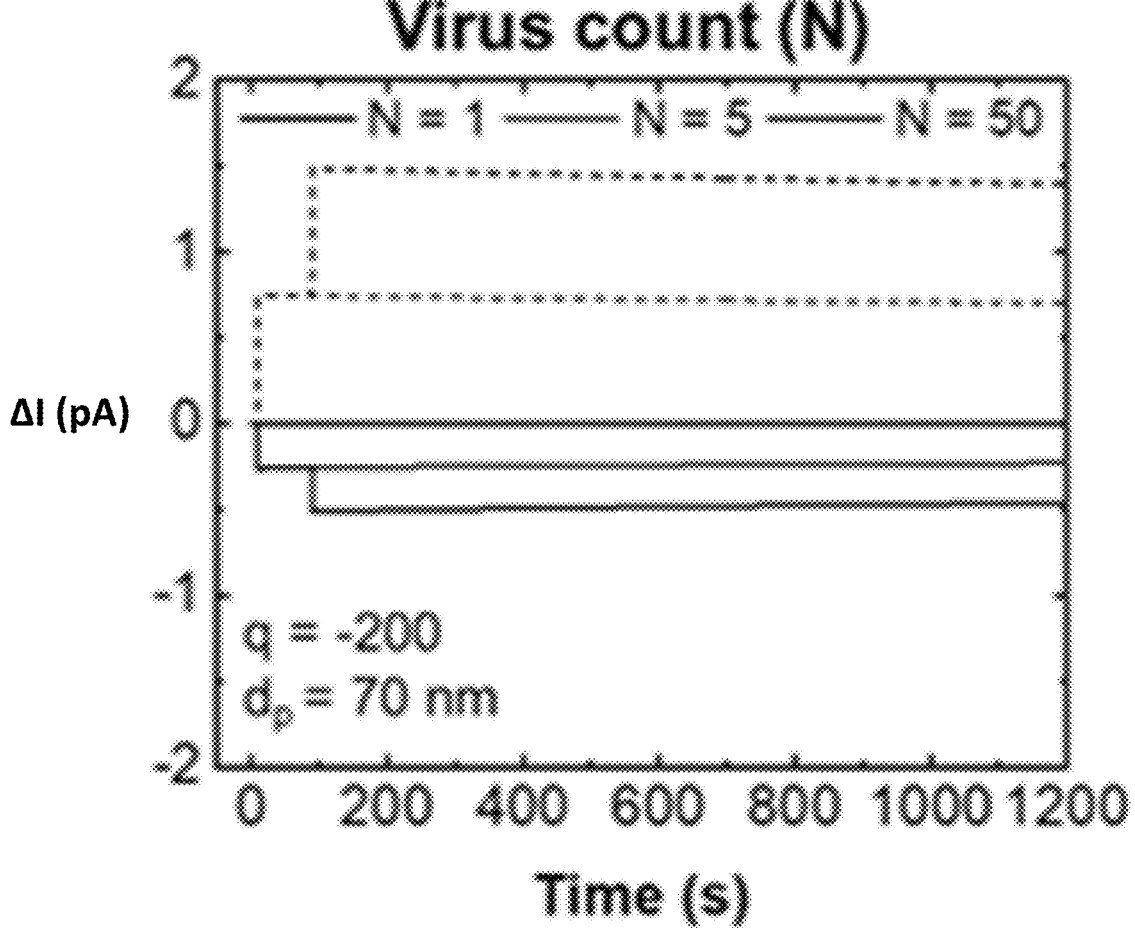
Figure 44:
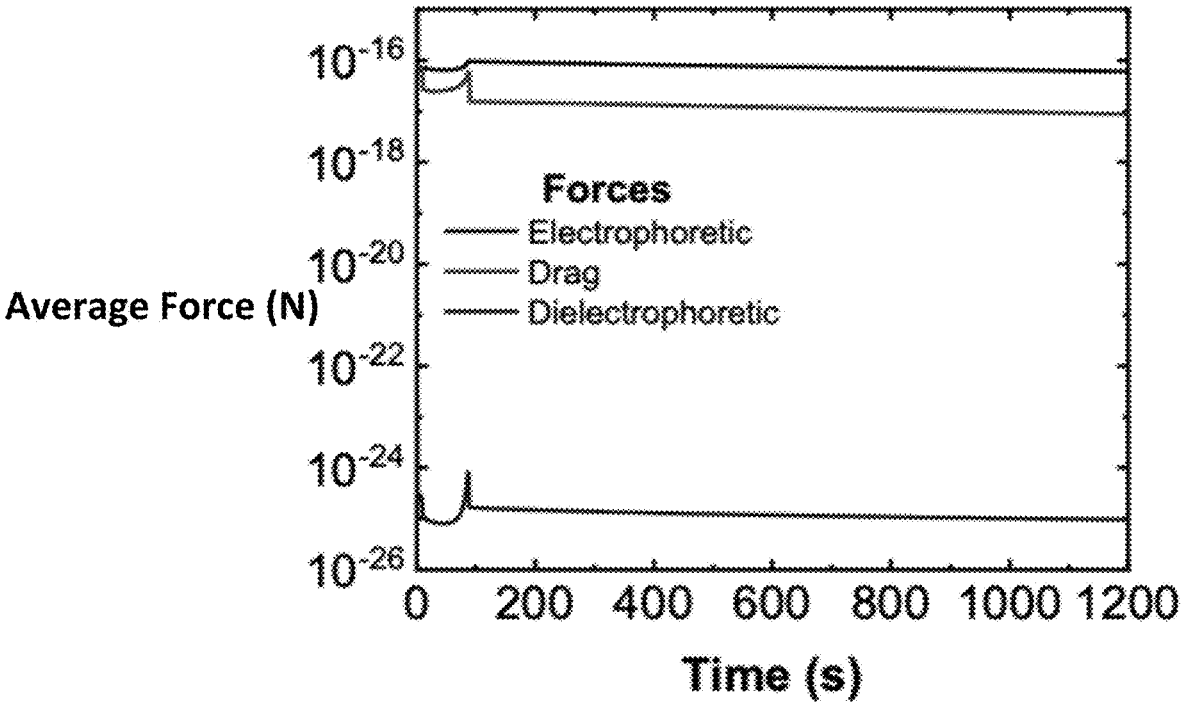
FIG. 44 shows a comparison of the average forces acting on the virus particles.

FIGS. 41-43 show the effect of various virus properties on the amperometric detection of capture events in a 1 μl droplet, wherein FIG. 41 shows the background subtracted current (ΔI) obtained from chronoamperometric measurements demonstrating the effect of the virus surface charge (q), FIG. 42 shows the effect of virus size ($d_p$), and FIG. 44 shows the effect of virus number (N). The solid and dashed lines represent the generator and collector current, respectively. Parameters: 1 mM [Fe(CN)$_6$]$^{4-}$, 1 mM KCl, $E_{coll}$= −0.15 V, $E_{gen}$=0.6 V. In the absence of any surface charge (q=0), no virus particles are attached to the electrode. As the charge increases, the electrophoretic force ($F_{EP}$) increases proportionally, resulting in more capture events (2 for q=−300 opposed to 1 for other charge values) and reduced capture time. The current steps shown are proportional to the surface area of the virus particle ($I_{step} \propto r_p^2$)[63] and result in a ~1 pA current step for a 70 nm particle, which is similar in magnitude to previously reported values using murine cytomegalovirus. More pronounced steps in current are seen for larger particles. Viruses such as SARS-CoV and SARS-CoV-2 have been reported to be on the order of 70-100 nm, with reports ranging from around 50 nm for SARS-CoV up to 140 nm for SARS-CoV-2. Other viruses, such as herpes simplex virus, can be 250 nm in size while hepatitis A virus particles have been reported to be just 27 nm in size. Sepunaru et al. demonstrated single-particle capture events of influenza virus (measured size ~125 nm) conjugated with silver nanoparticles. They showed current spikes on the order of 10 pA due to oxidation of the nanoparticles upon capture at the electrode. In the present case, for a particle size of 200 nm, step sizes of ~5 pA are observed, which is comparable to previous reports using silica nanoparticles.

Interestingly, the time required for the first capture event increases with particle size, likely a result of the larger drag force ($F_D$). Although particle size has implications in both the drag force ($F_D \propto d_p$) and dielectrophoretic force ($F_{DEP} \propto d_p^3$) acting on the particle, for DC measurements such as those here, $F_{DEP}$ does not contribute significantly to the transport of the virus particles (see FIG. 44 for a comparison of average forces acting on the virus particles). FIG. 44 shows a comparison of the average forces acting on the virus particles. Parameters: 1 mM KCl, 1 mM [Fe(CN)$_6$]$^{4-}$, $E_{coll}$=−0.15 V, $E_{gen}$=0.6 V, $d_{cap}$=0.5 μm, $d_e$=2 μm, $h_e$=8.5 μm, $d_p$=70 nm, N=10, q=−200. Increasing the number of particles results in more capture events, although no response is seen for N=1, there is only one capture event for N=5. In an effort to improve the number of capture events and achieve the ultimate goal of single-entity detection, droplet volume is confined from 1 μl down to 2 nl. Droplets of this scale and even smaller can be created and manipulated using a microcapillary pressure injection system.

Figure 45:
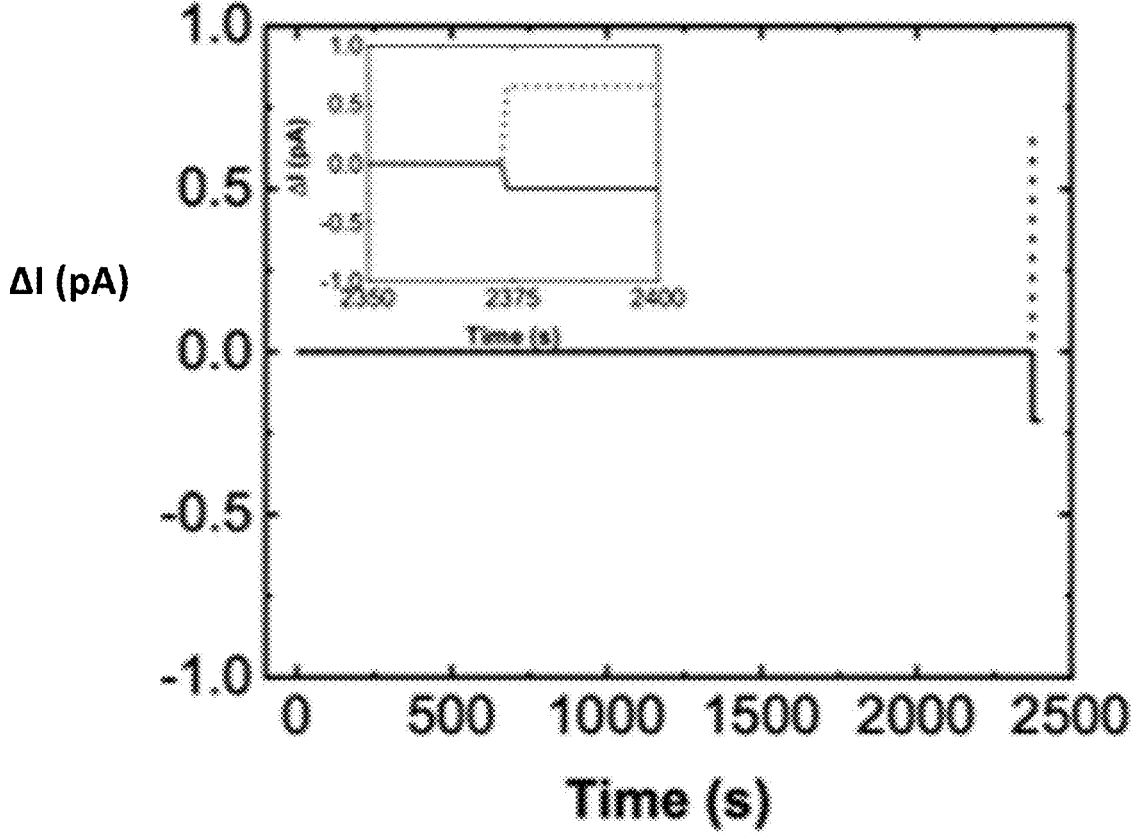
FIG. 45 shows background subtracted current (ΔI) obtained from chronoamperometric measurements within a 2 nl droplet demonstrating the current steps caused by virus particle attachment to the electrode surface for N=2.
Figure 46:
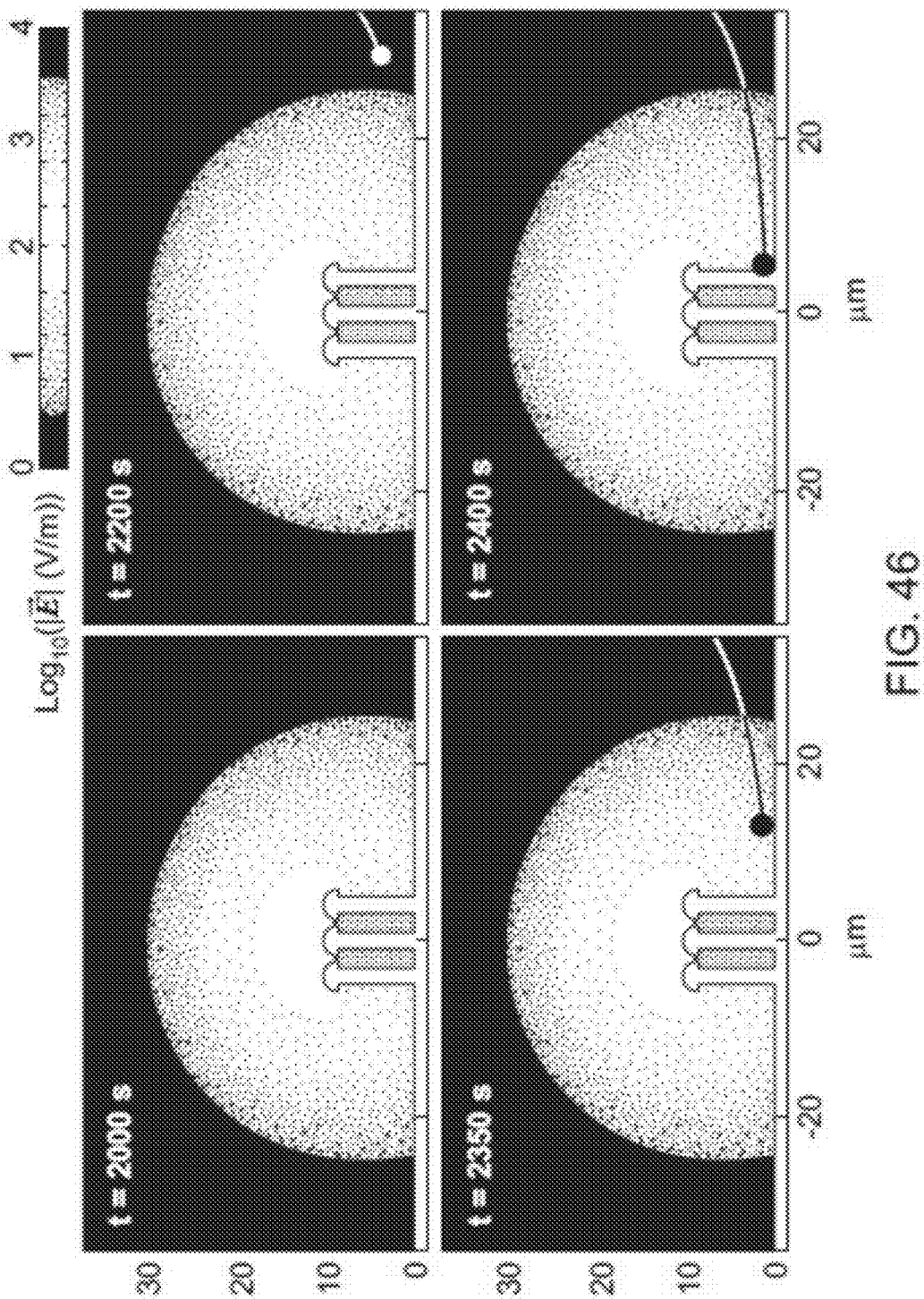
FIG. 46 show the electric field at a sampling of time points showing the evolution of the particle attachment to the electrode surface.

Alternatively, controlled evaporation of the droplet has been utilized as a preconcentration strategy as well. Nanoliter volumes are also commonly achieved in microfluidic channels which will be discussed in regard to the IDE structure. FIG. 45 shows background subtracted current (ΔI) obtained from chronoamperometric measurements within a 2 nl droplet demonstrating the current steps caused by virus particle attachment to the electrode surface for N=2. Solid and dashed lines represent the generator and collector currents, respectively. FIG. 46 shows the electric field at a sampling of time points showing the evolution of the particle attachment to the electrode surface. Parameters for FIGS. 45 and 46 are: 1 mM [Fe(CN)$_6$]$^{4-}$, 1 mM KCl, $E_{coll}$=−0.15 V, $E_{gen}$=0.6 V, $d_p$=70 nm, q=−200. The amperometric current for N=2 for a particle size of $d_p$=70 nm in a 2 nl droplet. With 2 virus particles present, one particle is sufficiently far away such that it is not attracted to the electrode over the time frame tested. The other particle can be seen attaching after ~40 min. The corresponding time evolution of the virus capture is also shown with the electric field.

Figure 47:
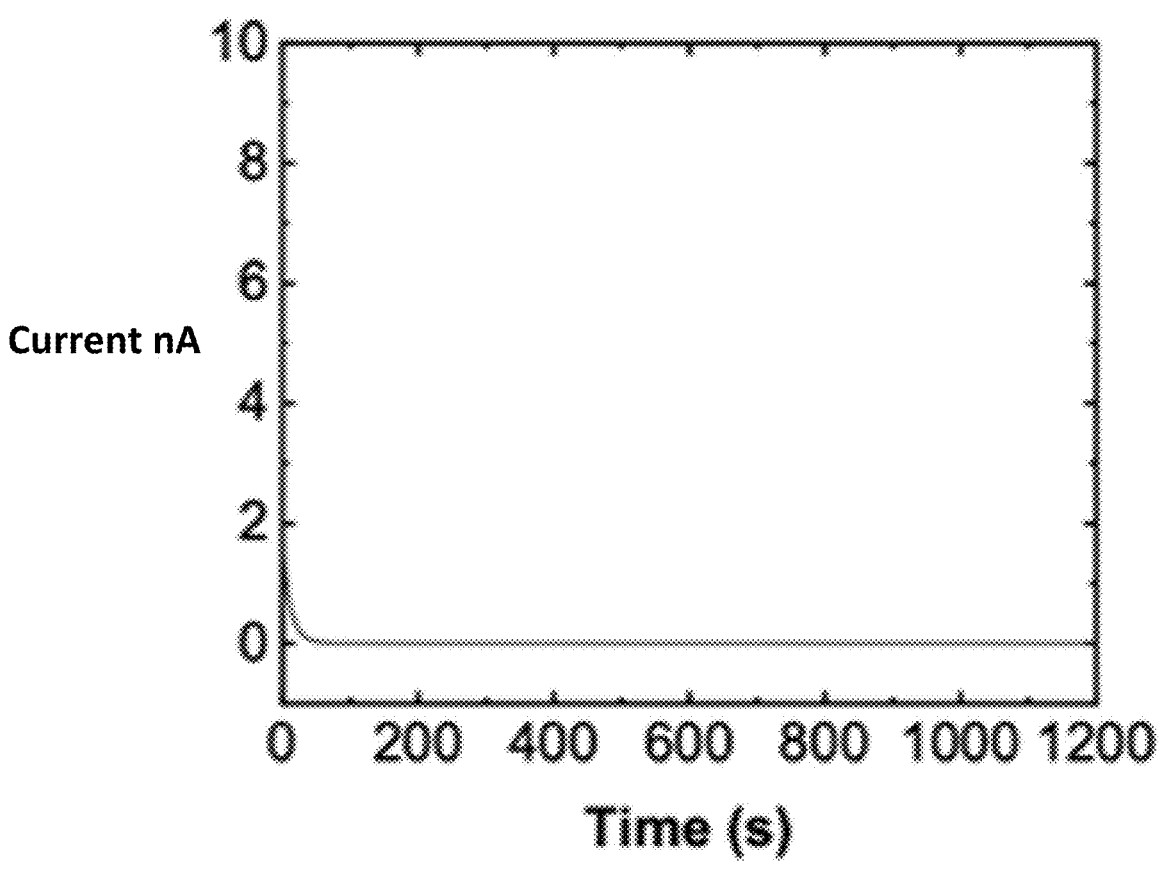
FIG. 47 shows a chronoamperometric scan with the collector left floating in the ring-disk 2 nl droplet configuration (generator current shown).
Figure 48:
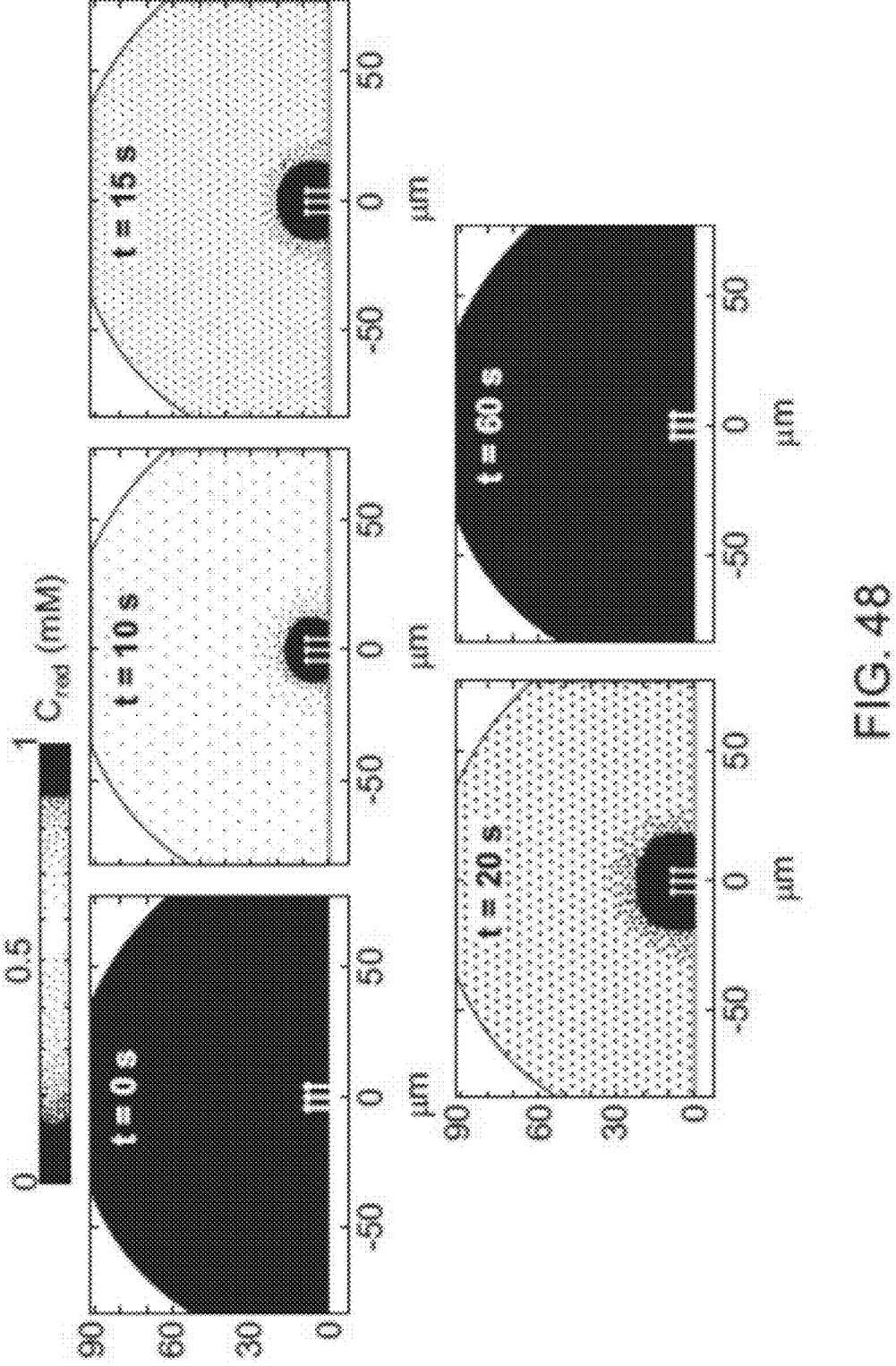
FIG. 48 shows time evolution of $c_{red}$.
Figure 49:
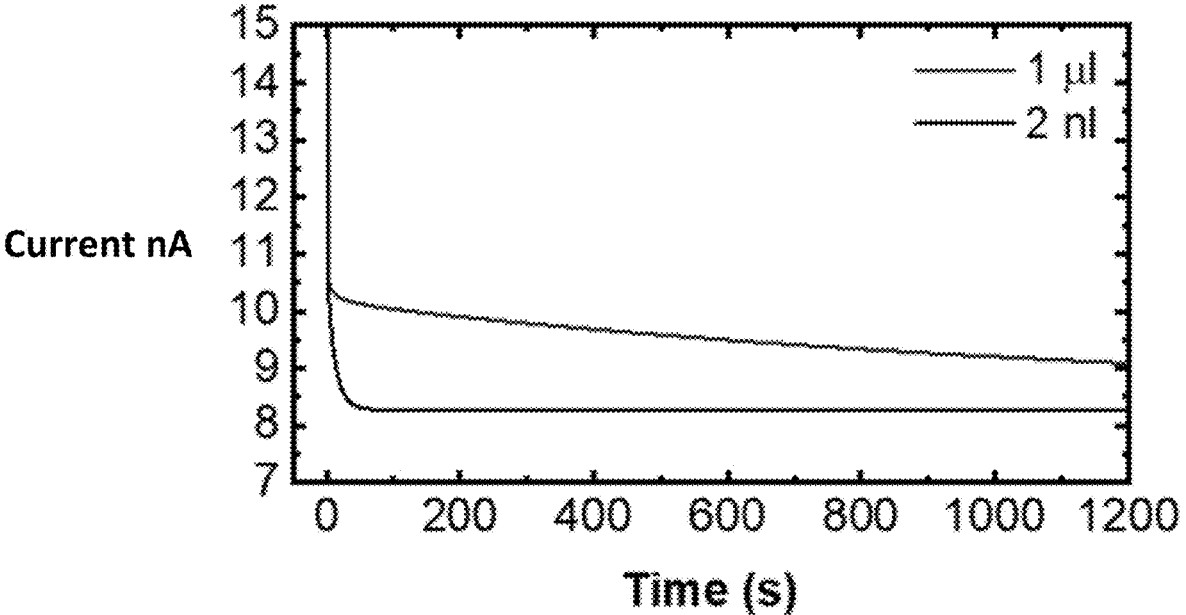
FIG. 49 shows the effect of the droplet size on the generator current during chronoamperometric scans.

One possible drawback of performing electrochemical measurements in such confined geometries on the timescales shown here is the extent of the diffusion layer. Estimating the diffusion layer as $l \sim (Dt)^{1/2}$, one obtains a layer of roughly 1 mm, well beyond the confines of the droplet. In the absence of redox cycling, the analyte supply is depleted after about 60 s, and the current diminishes to ~0 (see FIGS. 47-48). FIG. 47 shows a chronoamperometric scan with the collector left floating in the ring-disk 2 nl droplet configuration (generator current shown). FIG. 48 shows time evolution of $c_{red}$. Parameters for FIGS. 47 and 48 are: 1 mM KCl, 1 mM [Fe(CN)$_6$]$^{4-}$, $E_{coll}$=floating, $E_{gen}$=0.6 V, $d_{cap}$=0.5 μm, $d_e$=2 μm, $h_e$=8.5 μm. However, the inventive configuration takes advantage of redox cycling to constantly resupply [Fe(CN)$_6$]$^{3-/4-}$, leading to a finite steady-state current and allowing for virus detection to continue within the droplet. Due to these constraints associated with the droplet geometry, the amperometric current of the 2 nl droplet is slightly less than the 1 μl droplet (see FIG. 49). FIG. 49 shows the effect of the droplet size on the generator current during chronoamperometric scans. Parameters: 1 mM KCl, 1 mM [Fe(CN)$_6$]$^{4-}$, $E_{coll}$=−0.15 V, $E_{gen}$=0.6 V, $d_{cap}$=0.5 μm, $d_e$=2 μm, $h_e$=8.5 μm.

Electrochemical Analysis in the Presence of Virus Particles (IDE Configuration)

Figures 50A, 50B:
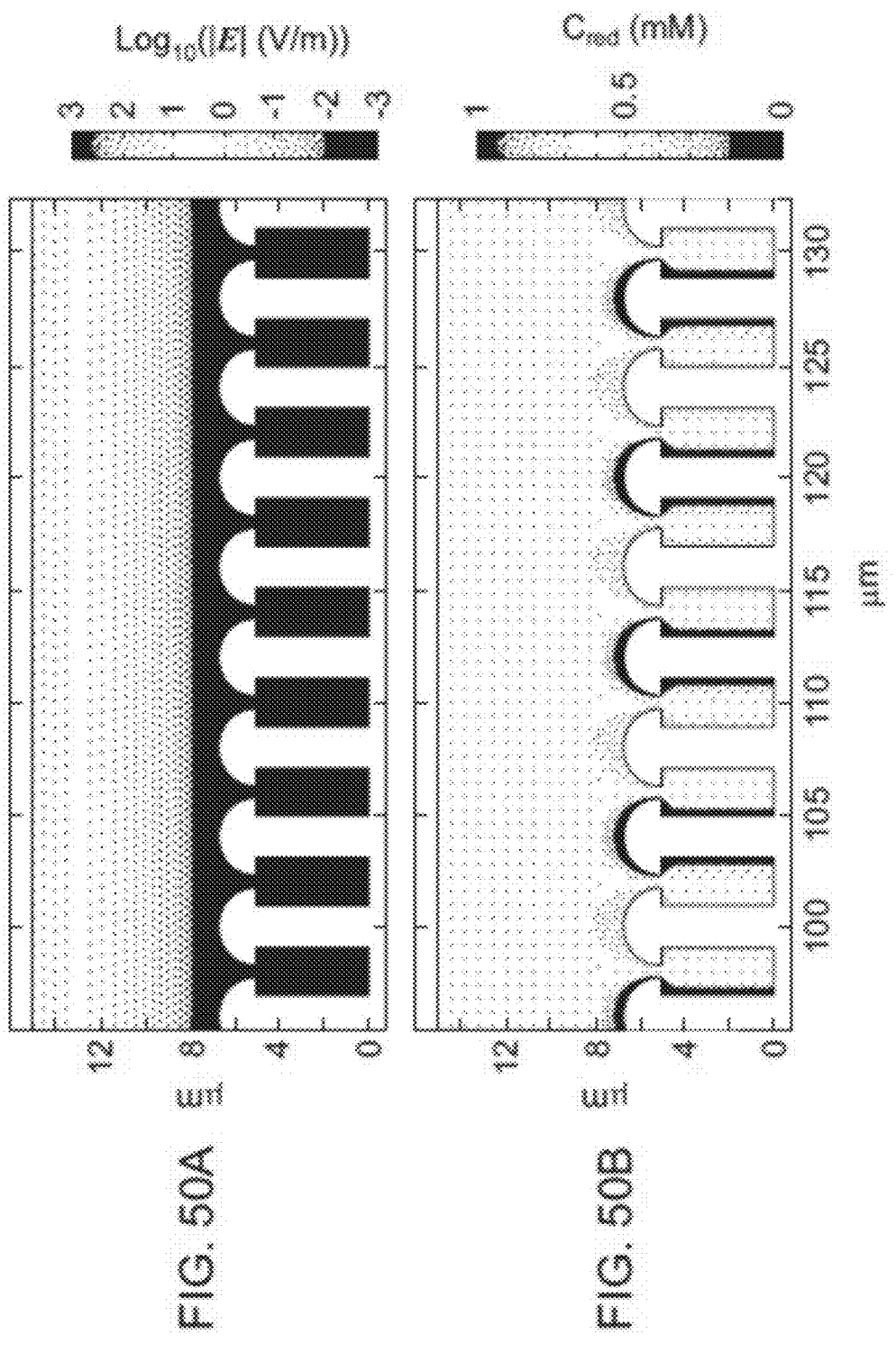
FIGS. 50A and 50B show electric field distribution of a cross section sample of an exemplary interdigitated electrode (IDE) and microchannel, and a concentration profile of $c_{red}$ showing the overlapping diffusion layers of adjacent generator and collector electrodes, respectively.
Figure 51:
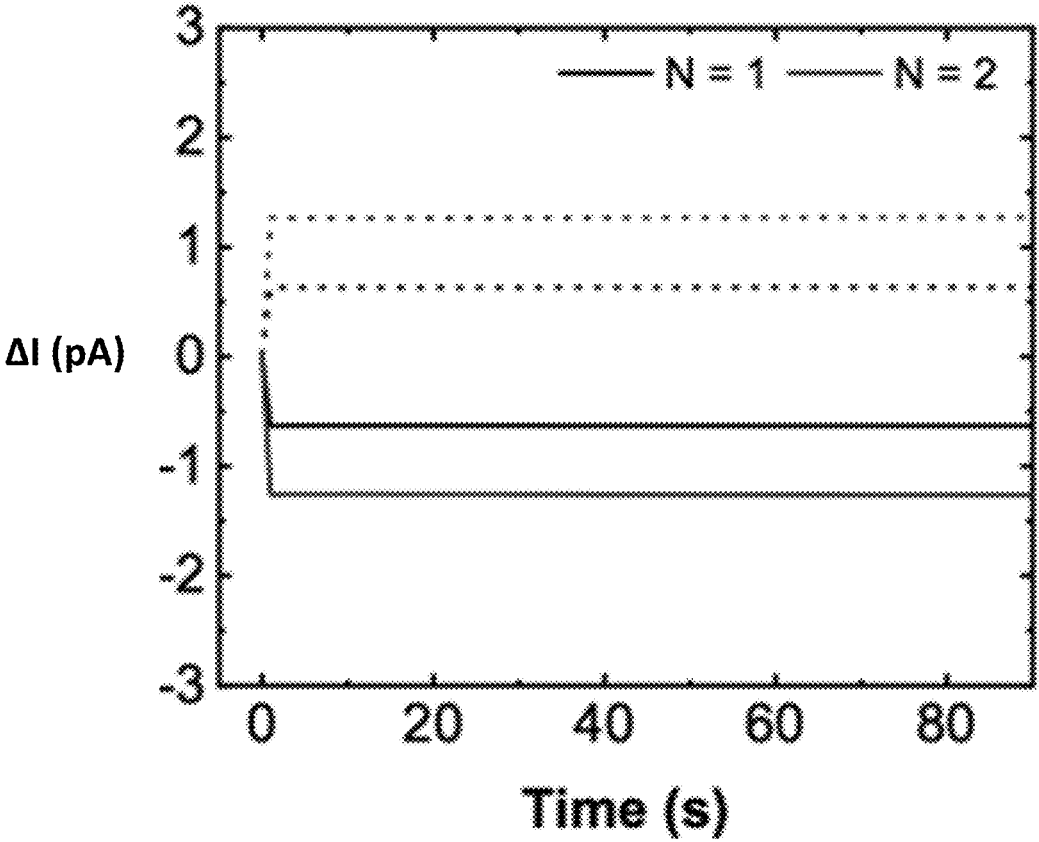
FIG. 51 shows background subtracted current (ΔI) obtained from chronoamperometric measurements demonstrating the current steps caused by virus particle attachment to the electrode surface.

FIGS. 50A and 50B show electric field distribution of a cross section sample of the interdigitated electrode (IDE) and microchannel, and a concentration profile of $c_{red}$ showing the overlapping diffusion layers of adjacent generator and collector electrodes, respectively. FIG. 51 shows background subtracted current (ΔI) obtained from chronoamperometric measurements demonstrating the current steps caused by virus particle attachment to the electrode surface. Note that the attachment occurs within 1 second for both N=1 and N=2. Solid and dashed lines represent the generator and collector currents, respectively. Parameters for FIGS. 50-51 are: 1 mM [Fe(CN)$_6$]$^{4-}$, 1 mM KCl, $E_{coll}$=−0.15 V, $E_{gen}$=0.6 V, $d_p$=70 nm, q=~200.

Figure 52:
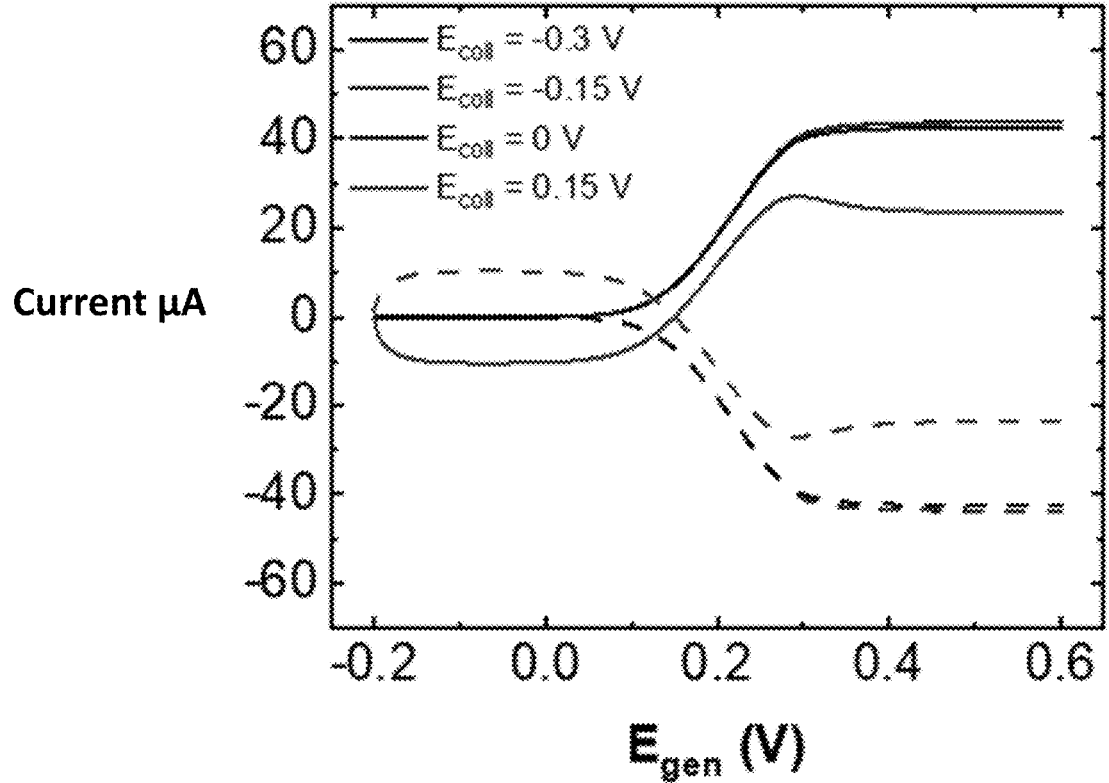
FIG. 52 shows the effect of varying the collector bias with an exemplary IDE configuration.
Figure 53:
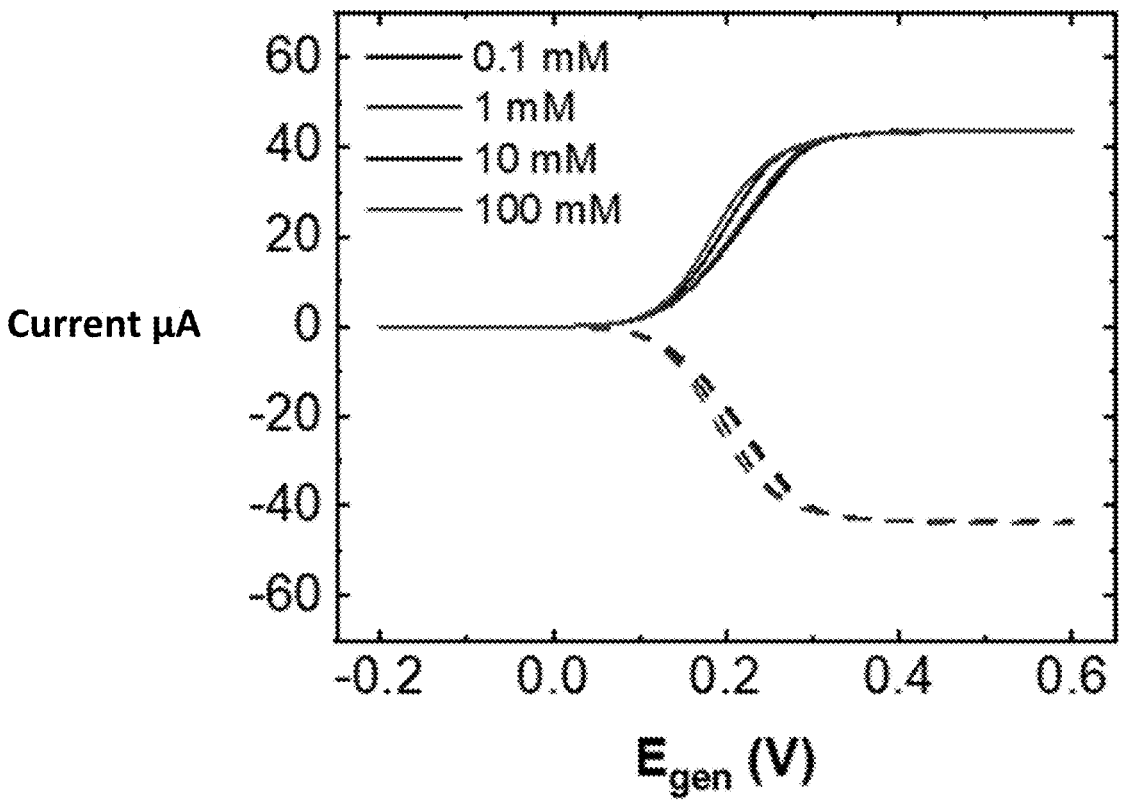
FIG. 53 shows the effect of KCl electrolyte concentration on the electrochemical response of an exemplary IDE geometry.
Figure 54:
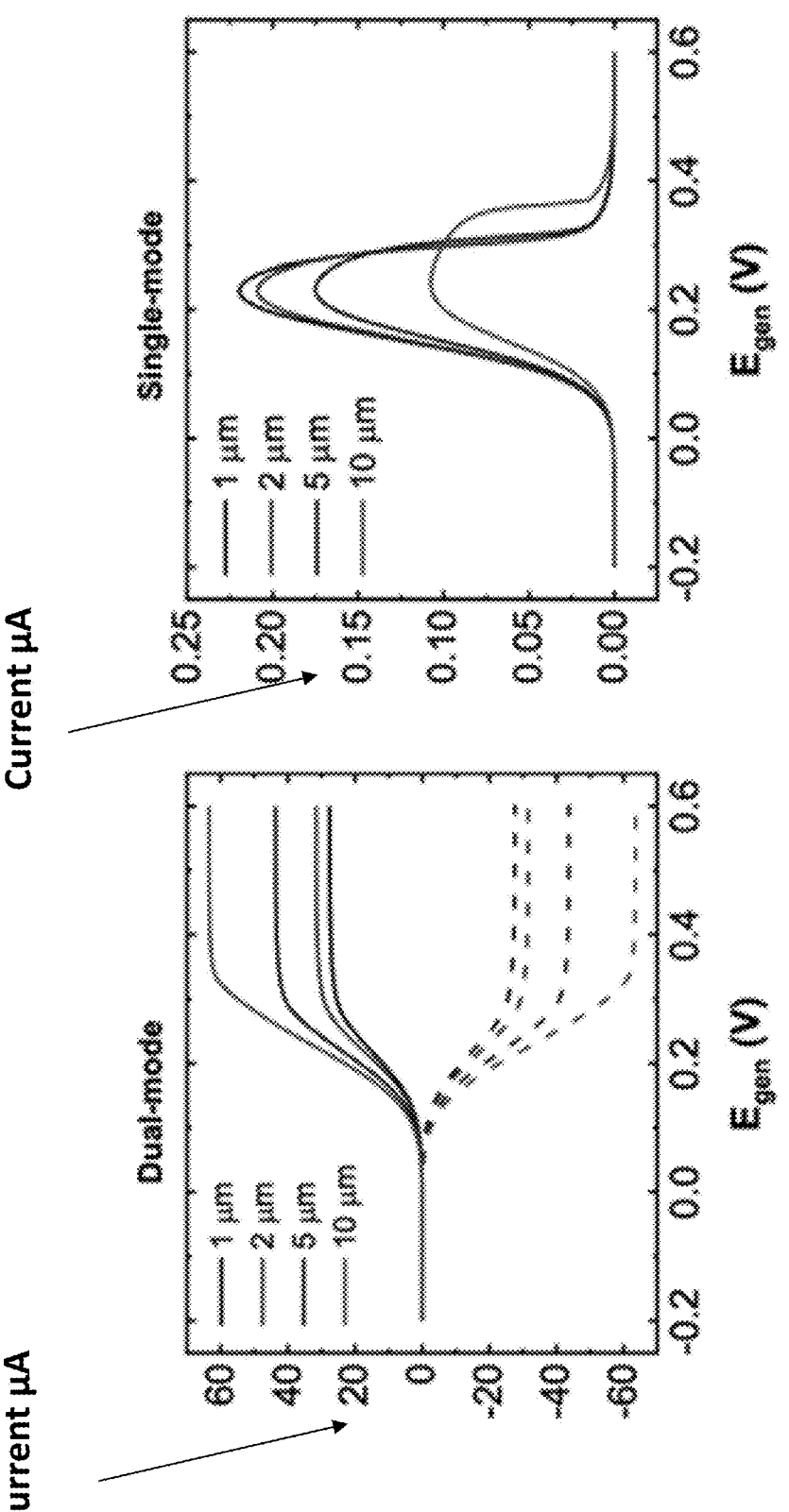
FIG. 54 shows the effect of the IDE electrode height ($h_e$) on the electrochemical response in dual-mode and single-mode configurations.
Figure 55:
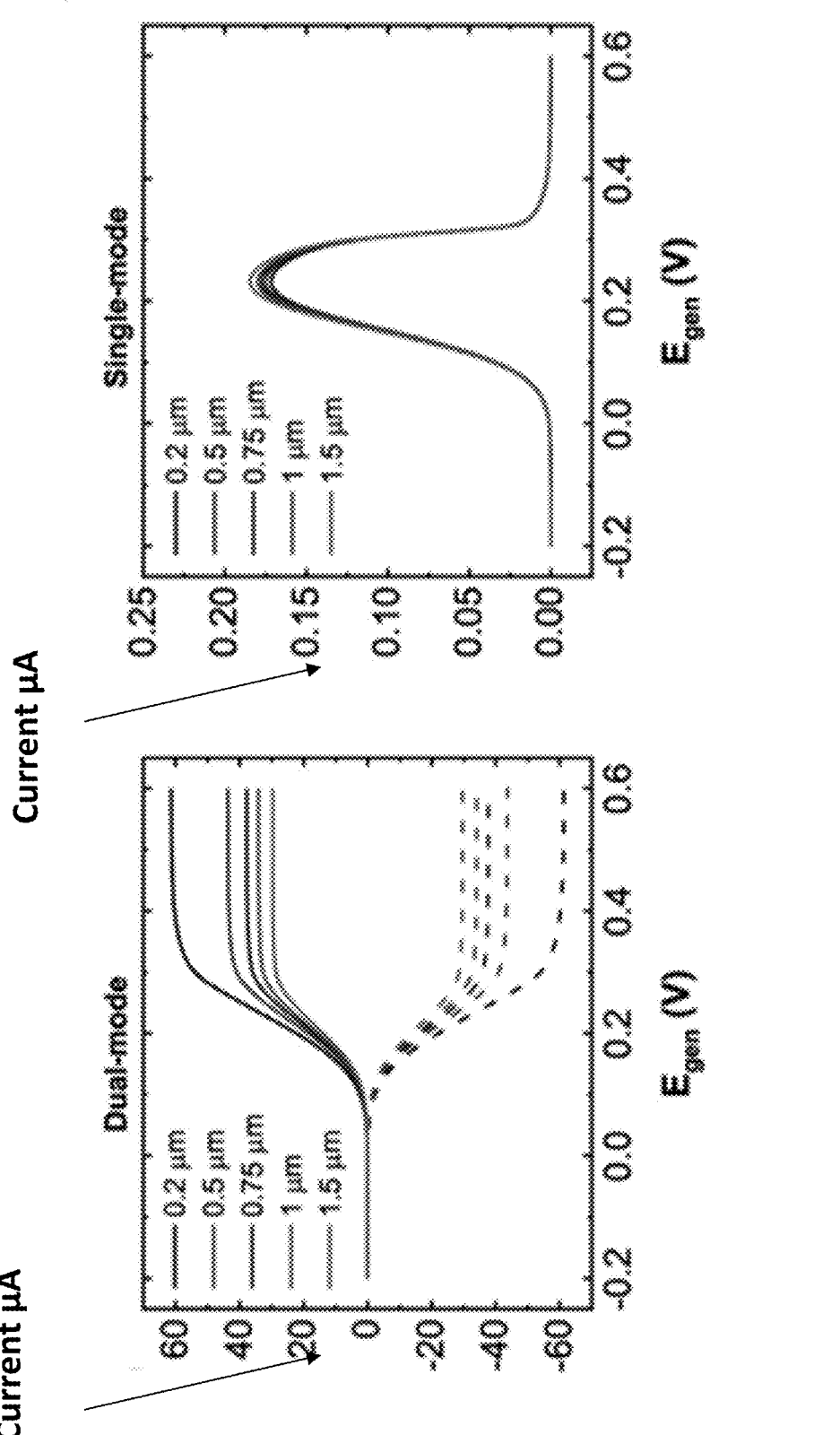
FIG. 55 shows the effect of the IDE electrode cap spacing ($d_{cap}$) on the electrochemical response in dual-mode and single-mode configurations.

After demonstrating the virus capture ability of an isolated generator-collector ring-disk pair in a droplet configuration, an interdigitated electrode (IDE) design was investigate which is more suitable for integration with microfluidic channels rather than individual droplets. As discussed below, the IDE also improves detection at lower particle number, which may be an issue with the droplet configuration. The IDE structure is a common generator-collector configuration whereby sub-micrometer spacing (α) is traditionally achieved using more costly fabrication methods, such as electron beam lithography. The proposed template-driven overgrowth method is also applicable here and can be used to further reduce the lateral spacing between generator and collector. The IDE with overgrown cap is placed within a microfluidic channel of 15 μm in height, which inherently confines the virus particles close to the electrodes. FIG. 50A shows the electric field distribution of an exemplary cross section of the IDE with electrode spacing $d_e$=2 μm, $h_e$=2 μm, and $d_{cap}$=0.5 μm. Again, $E_{coll}$= –0.15 V and $c_{KCl}$=1 mM (see FIGS. 52-53 for effect of collector bias and KCl concentration). FIG. 52 shows the effect of varying the collector bias with the IDE configuration. The solid lines represent the generator current while the dashed lines are the corresponding collector current. Parameters: 1 mM [Fe(CN)$_6$]$^{4-}$, 1 mm KCl, scan rate=50 mV s$^{-1}$, $d_{cap}$=0.5 μm, $d_e$=2 μm, $h_e$=5 μm. FIG. 53 shows the effect of the KCl electrolyte concentration on the electrochemical response of the IDE geometry. The solid lines represent the generator current while the dashed lines are the corresponding collector current. Parameters: 1 mM [Fe(CN)$_6$]$^{4-}$, $E_{coll}$=–0.15 V, scan rate=50 mVs$^{-1}$, $d_{cap}$=0.5 μm, $d_e$=2 μm, $h_e$=5 μm. Electric fields above 1 kV m$^{-1}$ in magnitude are seen in the immediate vicinity of the electrode, which is sufficient for electrophoretic manipulation. FIG. 50B highlights the concentration profile of [Fe(CN)$_6$]$^{4-}$ at the generator and collector. Significant overlap in the diffusion layers of adjacent electrodes is apparent, which allows the IDE to reach a steady-state current during the LSV scan that is not seen in single-mode. In fact, without redox cycling, the [Fe(CN)$_6$]$^{4-}$ is depleted very rapidly during LSV, resulting in the current dropping to near 0 before the scan is complete (see FIGS. 54-55). FIG. 54 shows the effect of the IDE electrode height ($h_e$) on the electrochemical response in dual-mode and single-mode configurations. Parameters: 1 mM [Fe(CN)$_6$]$^{4-}$, 1 mm KCl, $E_{coll}$=–0.15 V or floating, scan rate=50 m V s$^{-1}$, $d_{cap}$=0.5 μm, $d_e$=2 μm. FIG. 55 shows the effect of the IDE electrode cap spacing ($d_{cap}$) on the electrochemical response in dual-mode and single-mode configurations. Parameters: 1 mM [Fe(CN)$_6$]$^{4-}$, 1 mm KCl, $E_{coll}$=–0.15 V or floating, scan rate=50 mV s$^{-1}$, $d_e$=2 μm, $h_e$=5 μm.

Figure 56:
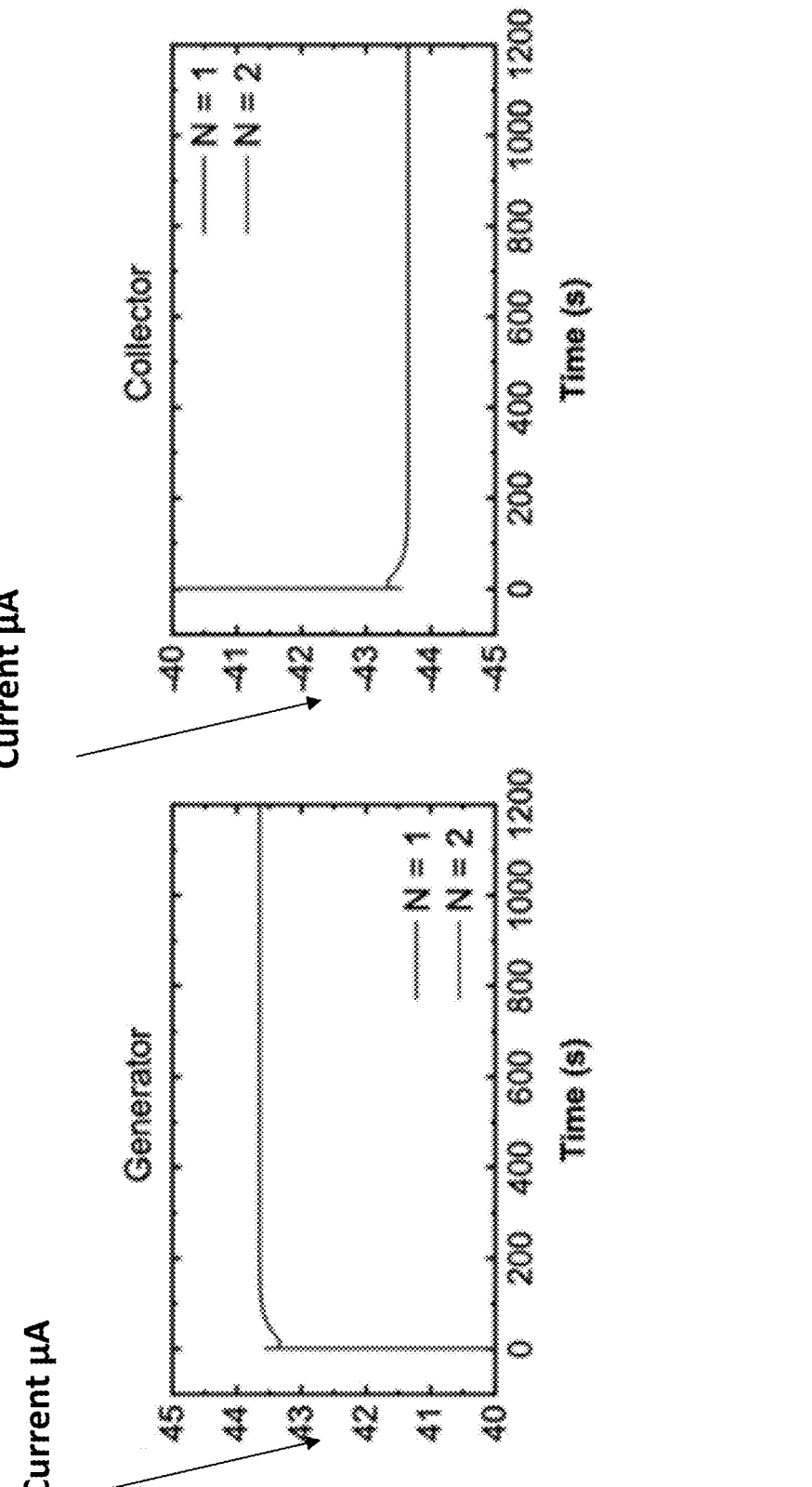
FIG. 56 shows the raw chronoamperometric scans in an exemplary IDE configuration with N=1 and 2 virus particles showing the generator current and the collector current.

The IDE structure is evaluated with N=1 and 2 virus particles of 70 nm size and q=–200, similar to our previous studies with the droplet configuration. The background subtracted current for both N=1 and 2 is presented in FIG. 51 (the unprocessed chronoamperometry data are shown in FIG. 56). FIG. 56 shows the raw chronoamperometric scans in the IDE configuration with N=1 and 2 virus particles showing the generator current and the collector current. Parameters: 1 mM [Fe(CN)$_6$]$^{4-}$, 1 mm KCl, $E_{coll}$=–0.15 V, $E_{coll}$=0.6 V, $d_e$=2 μm, $h_e$=5 μm, $d_{cap}$=0.5 μm, $d_p$=70 nm, q=–200. The particle attaches very quickly in the IDE configuration-after just 1 s. This is a significant improvement over the isolated generator-collector ring-disk geometry, which only recorded one capture event with N=2 and no capture events with N=1 in the 2 nl droplet. The main drawback of using such a large area electrode is the reduced blocking effect caused by the attachment of the virus particle compared with the smaller ring-disk geometry. As a result, the relative reduction in current per virus particle attachment is smaller.

The inventive biosensor scheme provides rapid and sensitive electrochemical "particle counting" with low fabrication costs. While the focus of this study was to demonstrate detection time and sensitivity, it can be complemented by other methods to enable selective detection as well. This can be achieved by incorporating biorecognition elements specific to the virus of interest. One example from Dick et al. used glucose oxidase (GOx)-modified antibodies that attached to the surface of the target virus. As the virus-antibody-GOx unit adsorbed on the electrode surface, the GOx acted as a reducing agent for the FcMeOH$^+$ being generated at the electrode surface, which allowed for reoxidation of the FcMeOH and significant amplification of the signal. An alternative approach could be to extract the target virus from the sample matrix using magnetic nanoparticles (MNPs) conjugated with the corresponding antibody or aptamer. The virus-MNP conjugate can then be selectively resuspended in the test solution for downstream counting. If needed, by using a thermally reversible conjugation mechanism, such as the Diels-Alder approach, the virus particles could be removed from the MNPs via heating.

As can be appreciated from the present disclosure, embodiments provide a means for single virus counting using two tunable generator-electrode configurations. The design combines redox cycling with electrophoresis-driven electrode-particle collision for rapid and sensitive virus detection. The impact of various experimental and geometric parameters on the electrochemical properties is investigated using detailed finite element analysis. These designs (either droplet-based or channel-based designs) have the potential for integration with microfluidic and other lab-on-a-chip platforms for portable, point-of-care virus detection. Amplification factors and collector efficiencies are highly dependent on the generator-collector spacing and range from beyond 4 to as little as ~1.1 for the amplification factor and from 0.8 down to less than 0.2 for the collector efficiency. While the redox amplification reported here is modest compared to previous reports, it should be emphasized that the dimensionality of the proposed platform is well within the capabilities of standard photolithography techniques. Moreover, the overgrowth strategy is compatible with scalable electrodeposition methods. Strategies to improve the amplification, such as nanocavity-based sensors, could be employed but may limit the reach of the electric field into the bulk solution and make the electrophoretic enrichment of viral particles challenging.

The detection scheme detailed herein relies on the virus particle blocking or hindering the mass transfer of the electrochemical redox probe upon colliding with the electrode, which causes a detectable step in the amperometric current. The nature of the collisions is found to depend on the virus surface charge, size, and quantity. Although the isolated generator-collector ring-disk (droplet configuration) is more sensitive to virus attachment due to its smaller surface area, the IDE takes advantage of a large capture area and particle confinement within the microchannel to detect virus particles on the order of seconds. The present FEA results provide valuable guidance for the practical fabrication of biosensors suitable for single particle counting, which has potentially broad applications ranging from electrochemical virus detection to immunoassays and molecular diagnostics.

REFERENCES

The following reference are incorporated herein by reference in their entries.

(1) Caygill, R. L.; Blair, G. E.; Millner, P. A. A Review on Viral Biosensors to Detect Human Pathogens. *Anal. Chim. Acta* 2010, 687, 8-15.

(2) Fox, J. D. Respiratory Virus Surveillance and Outbreak Investigation. *J. Clin. Virol.* 2007, 40, S24-S30.

(3) Baig, A. M. Chronic COVID Syndrome: Need for an Appropriate Medical Terminology for Long-CoVID and COVID Long-Haulers. *J. Med. Virol.* 2021, 93, 2555-2556.

(4) Johns Hopkins University. COVID-19 Dashboard by the Center for Systems Science and Engineering (CSSE) at Johns Hopkins University (JHU) https://coronavirus.jh-u.edu/map.html (accessed Feb. 22, 2022).

(5) Kisely, S.; Warren, N.; McMahon, L.; Dalais, C.; Henry, I.; Siskind, D. Occurrence, Prevention, and Management of the Psychological Effects of Emerging Virus Outbreaks on Healthcare Workers: Rapid Review and Meta-Analysis. *BMJ* 2020, 369, m1642.

(6) Bustin, S. A. Absolute Quantification of Mrna Using Real-Time Reverse Transcription Polymerase Chain Reaction Assays. *J. Mol. Endocrinol.* 2000, 25, 169-193.

(7) Voller, A.; Bartlett, A.; Bidwell, D. E.; Clark, M. F.; Adams, A. N. The Detection of Viruses by Enzyme Linked Immunosorbent Assay (ELISA). *J. Gen. Virol.* 1976, 33, 165-167.

(8) Kievits, T.; van Gemen, B.; van Strijp, D.; Schukkink, R., Dircks, M.; Adriaanse, H.; Malek, L.; Sooknanan, R.; Lens, P. NASBA™ Isothermal Enzymatic in Vitro Nucleic Acid Amplification Optimized for the Diagnosis of HIV-1 Infection. *J. Virol. Methods* 1991, 35, 273-286.

(9) Ito, M.; Watanabe, M.; Nakagawa, N.; Ihara, T.; Okuno, Y. Rapid Detection and Typing of Influenza A and B by Loop-Mediated Isothermal Amplification: Comparison with Immunochromatography and Virus Isolation. *J. Virol. Methods* 2006, 135, 272-275.

(10) Arai, H.; Petchclai, B., Khupulsup, K.; Kurimura, T.; Takeda, K. Evaluation of a Rapid Immunochromatographic Test for Detection of Antibodies to Human Immunodeficiency Virus. *J. Clin. Microbiol.* 1999, 37, 367-370.

(11) Zhao, Z.; Huang, C.; Huang, Z.; Lin, F.; He, Q.; Tao, D.; Jaffrezic-Renault, N.; Guo, Z. Advancements in Electrochemical Biosensing for Respiratory Virus Detection: A Review. *TrAC Trends Anal. Chem.* 2021, 139, 116253.

(12) Vishnu, N.; Sharma, C. S.; Senthil Kumar, A. A Low-Cost and Miniaturized Electrochemical Cell for Low-Sample Analyses. *Microchem. J.* 2020, 159, 105591.

(13) Wolfrum, B.; Kätelhön, E.; Yakushenko, A.; Krause, K. J.; Adly, N.; Hüske, M.; Rinklin, P. Nanoscale Electrochemical Sensor Arrays: Redox Cycling Amplification in Dual-Electrode Systems. *Acc. Chem. Res.* 2016, 49, 2031-2040.

(14) Guo, J.; Wei, T.; Huang, Q., Li, M.; Yang, C.; Mou, J.; Shi, L.; Gao, T.; Li, G. Direct Acupuncture of Nitric Oxide by an Electrochemical Microsensor with High Time-Space Resolution, *Biosens. Bioelectron.* 2022, 195, 113667.

(15) Ma, C.; Contento, N. M.; Gibson, L. R.; Bohn, P. W. Redox Cycling in Nanoscale-Recessed Ring-Disk Electrode Arrays for Enhanced Electrochemical Sensitivity. *ACS Nano* 2013, 7, 5483-5490.

(16) Lee, G.-Y.; Park, J.-H.; Wook Chang, Y.; Cho, S.; Kang, M.-J.; Pyun, J.-C. Chronoamperometry-Based Redox Cycling for Application to Immunoassays. *ACS Sensors* 2018, 3, 106-112.

(17) Bard, A. J., Faulkner, L. R. Electrochemical Methods: Fundamentals and Applications, $2^{nd}$ ed.; John Wiley and Sons, Inc: New York, 2001.

(18) Kätelhön, E.; Hofmann, B.; Lemay, S. G.; Zevenbergen, M. A. G.; Offenhäusser, A.; Wolfrum, B. Nanocavity Redox Cycling Sensors for the Detection of Dopamine Fluctuations in Microfluidic Gradients. *Anal. Chem.* 2010, 82, 8502-8509.

(19) Wolfrum, B.; Zevenbergen, M.; Lemay, S. Nanofluidic Redox Cycling Amplification for the Selective Detection of Catechol. *Anal. Chem.* 2008, 80, 972-977.

(20) Straver, M. G.; Odijk, M.; Olthuis, W., Van Den Berg, A. A Simple Method to Fabricate Electrochemical Sensor Systems with Predictable High-Redox Cycling Amplification. *Lab Chip* 2012, 12, 1548-1553.

(21) Goluch, E. D.; Wolfrum, B.; Singh, P. S.; Zevenbergen, M. A. G.; Lemay, S. G. Redox Cycling in Nanofluidic Channels Using Interdigitated Electrodes. *Anal. Bioanal. Chem.* 2009, 394, 447-456.

(22) Paixão, T. R. L. C.; Richter, E. M.; Brito-Neto, J. G. A.; Bertotti, M. Fabrication of a New Generator-Collector Electrochemical Micro-Device: Characterization and Applications. *Electrochem. commun.* 2006, 8, 9-14.

(23) Gross, A. J.; Holmes, S.; Dale, S. E. C.; Smallwood, M. J.; Green, S. J.; Peter Winlove, C.; Benjamin, N.; Winyard, P. G.; Marken, F. Nitrite/Nitrate Detection in Serum Based on Dual-Plate Generator-Collector Currents in a Microtrench. *Talanta* 2015, 131, 228-235.

(24) Ben-Yoav, H.; Winkler, T. E.; Kim, E.; Chocron, S. E.; Kelly, D. L.; Payne, G. F.; Ghodssi, R. Redox Cycling-Based Amplifying Electrochemical Sensor for in Situ Clozapine Antipsychotic Treatment Monitoring. *Electrochim. Acta* 2014, 130, 497-503.

(25) Winkler, T. E.; Dietrich, R.; Kim, E.; Ben-Yoav, H.; Kelly, D. L.; Payne, G. F.; Ghodssi, R. The Interplay of Electrode- and Bio-Materials in a Redox-Cycling-Based Clozapine Sensor. *Electrochem. commun.* 2017, 79, 33-36.

(26) Michen, B.; Graule, T. Isoelectric Points of Viruses. *J. Appl. Microbiol.* 2009, 109, 388-397.

(27) Hellberg, D.; Scholz, F.; Schauer, F.; Weitschies, W. Bursting and Spreading of Liposomes on the Surface of a Static Mercury Drop Electrode. *Electrochem. commun.* 2002, 4, 305-309.

(28) Hellberg, D.; Scholz, F.; Schubert, F.; Lovrić, M.; Omanović, D.; Hernández, V. A., Thede, R. Kinetics of Liposome Adhesion on a Mercury Electrode. *J. Phys. Chem. B* 2005, 109, 14715-14726.

(29) Rees, N. V.; Banks, C. E.; Compton, R. G. Ultrafast Chronoamperometry of Acoustically Agitated Solid Particulate Suspensions: Nonfaradaic and Faradaic Processes at a Polycrystalline Gold Electrode. *J. Phys. Chem. B* 2004, 108, 18391-18394.

(30) Clegg, A. D.; Rees, N. V; Banks, C. E.; Compton, R. G.; Clegg,] A D; Banks, C. E.; Compton, R. G.; Rees, N. V. Ultrafast Chronoamperometry of Single Impact Events in Acoustically Agitated Solid Particulate Suspensions. *ChemPhysChem* 2006, 7, 807-811.

(31) Xiao, X.; Bard, A. J. Observing Single Nanoparticle Collisions at an Ultramicroelectrode by Electrocatalytic Amplification. *J. Am. Chem. Soc.* 2007, 129, 9610-9612.

(32) Xiao, Y.; Fan, F. R. F.; Zhou, J.; Bard, A. J. Current Transients in Single Nanoparticle Collision Events. *J. Am. Chem. Soc.* 2008, 130, 16669-16677.

(33) Lee, J. Y.; Kim, B.-K.; Kang, M.; Park, J. H. Label-Free Detection of Single Living Bacteria via Electrochemical Collision Event. *Sci. Reports* 2016 61 2016, 6, 1-6.

(34) Frkonja-Kuczin, A.; Ray, L.; Zhao, Z.; Konopka, M. C.; Boika, A. Electrokinetic Preconcentration and Electrochemical Detection of *Escherichia Coli* at a Microelectrode. *Electrochim. Acta* 2018, 280, 191-196.

(35) Dick, J. E. Electrochemical Detection of Single Cancer and Healthy Cell Collisions on a Microelectrode. *Chem. Commun.* 2016, 52, 10906-10909.

(36) Dick, J. E.; Hilterbrand, A. T.; Strawsine, L. M.; Upton, J. W.; Bard, A. J. Enzymatically Enhanced Collisions on Ultramicroelectrodes for Specific and Rapid Detection of Individual Viruses. *Proc. Natl. Acad. Sci. U.S.A.* 2016, 113, 6403-6408.

27

(37) Goines, S.; Dick, J. E. Review—Electrochemistry's Potential to Reach the Ultimate Sensitivity in Measurement Science. *J. Electrochem. Soc.* 2020, 167, 037505.

(38) Quinn, B. M.; Hof, P. G. van't; Lemay, S. G. Time-Resolved Electrochemical Detection of Discrete Adsorption Events. *J. Am. Chem. Soc.* 2004, 126, 8360-8361.

(39) Boika, A.; Thorgaard, S. N.; Bard, A. J. Monitoring the Electrophoretic Migration and Adsorption of Single Insulating Nanoparticles at Ultramicroelectrodes. *J. Phys. Chem. B* 2012, 117, 4371-4380.

(40) Lebègue, E.; Anderson, C. M.; Dick, J. E.; Webb, L. J.; Bard, A. J. Electrochemical Detection of Single Phospholipid Vesicle Collisions at a Pt Ultramicroelectrode. *Langmuir* 2015, 31, 11734-11739.

(41) Chen, X.; Weibel, J. A.; Garimella, S. V. Water and Ethanol Droplet Wetting Transition during Evaporation on Omniphobic Surfaces. *Sci. Rep.* 2015, 5, 17110.

(42) Chandramohan, A.; Dash, S.; Weibel, J. A.; Chen, X.; Garimella, S. V. Marangoni Convection in Evaporating Organic Liquid Droplets on a Nonwetting Substrate. *Langmuir* 2016, 32, 4729-4735.

(43) Cerquido, M.; Proenca, M. P.; Dias, C.; Leitao, D. C.; Cardoso, S.; Freitas, P. P.; Aguiar, P.; Ventura, J. Tailoring the Cap's Morphology of Electrodeposited Gold Micro-Mushrooms. *Appl. Surf. Sci.* 2018, 445, 512-518.

(44) Rock, P. A. The Standard Oxidation Potential of the Ferrocyanide-Ferricyanide Electrode at 25° and the Entropy of Ferrocyanide Ion. *J. Phys. Chem.* 1966, 70, 576-580.

(45) Konopka, S. J.; McDuffie, B. Diffusion Coefficients of Ferri- and Ferrocyanide Ions in Aqueous Media, Using Twin-Electrode Thin-Layer Electrochemistry. *Anal. Chem.* 1970, 42, 1741-1746.

(46) Erickson, D.; Sinton, D.; Li, D. Joule Heating and Heat Transfer in Poly(Dimethylsiloxane) Microfluidic Systems. *Lab Chip* 2003, 3, 141-149.

(47) Cheng, N.-S. Formula for the Viscosity of a Glycerol-Water Mixture. *Ind. Eng. Chem. Res.* 2008, 47, 3285-3288.

(48) Takamura, K.; Fischer, H.; Morrow, N. R. Physical Properties of Aqueous Glycerol Solutions. J. Pet. Sci. Eng. 2012, 98-99, 50-60.

(49) Åkerlöf, G. Dielectric Constants of Some Organic Solvent-Water Mixtures at Various Temperature. *J. Am. Chem. Soc.* 1932, 54, 4125-4139.

(50) Ermolina, I.; Milner, J.; Morgan, H. Dielectrophoretic Investigation of Plant Virus Particles: Cow Pea Mosaic Virus and Tobacco Mosaic Virus. *Electrophoresis* 2006, 27, 3939-3948.

(51) Hughes, M. P.; Morgan, H.; Rixon, F. J. Measuring the Dielectric Properties of Herpes Simplex Virus Type 1 Virions with Dielectrophoresis. *Biochim. Biophys. Acta—Gen. Subj.* 2002, 1571, 1-8.

(52) Zafarani, H. R.; Mathwig, K.; Sudhölter, E. J. R.; Rassaei, L. Electrochemical Redox Cycling in a New Nanogap Sensor: Design and Simulation. *J. Electroanal. Chem.* 2016, 760, 42-47.

(53) Morita, M.; Hayashi, K.; Horiuchi, T.; Shibano, S.; Yamamoto, K.; Aoki, K. J. Enhancement of Redox Cycling Currents at Interdigitated Electrodes with Elevated Fingers. *J. Electrochem. Soc.* 2014, 161, H178.

(54) Odijk, M.; Olthuis, W.; Dam, V. A. T.; Van Den Berg, A. Simulation of Redox-Cycling Phenomena at Interdigitated Array (IDA) Electrodes: Amplification and Selectivity. *Electroanalysis* 2008, 20, 463-468.

28

(55) Cornejo, M. A.; Linz, T. H. Harnessing Joule Heating in Microfluidic Thermal Gel Electrophoresis to Create Reversible Barriers for Cell Enrichment. *Electrophoresis* 2021, 42, 1238-1246.

(56) Yan, H.; Wu, H. In *Encyclopedia of Microfluidics and Nanofluidics*; Li, D., Ed.; Springer US: Boston, MA, 2008; pp 886-896.

(57) Xiong, J.; Chen, Q.; Edwards, M. A.; White, H. S. Ion Transport within High Electric Fields in Nanogap Electrochemical Cells. *ACS Nano* 2015, 9, 8520-8529.

(58) MacCuspie, R. I.; Nuraje, N.; Lee, S. Y.; Runge, A.; Matsui, H. Comparison of Electrical Properties of Viruses Studied by AC Capacitance Scanning Probe *Microscopy. J. Am. Chem. Soc.* 2008, 130, 887-891.

(59) Hughes, M. P.; Morgan, H.; Rixon, F. J.; Burt, J. P. H.; Pethig, R. Manipulation of Herpes Simplex Virus Type 1 by Dielectrophoresis. *Biochim. Biophys. Acta*-Gen. Subj. 1998, 1425, 119-126.

(60) Morgan, H.; Hughes, M. P.; Green, N. G. Separation of Submicron Bioparticles by Dielectrophoresis. *Biophys. J.* 1999, 77, 516-525.

(61) Vega-Acosta, J. R., Cadena-Nava, R. D.; Gelbart, W. M.; Knobler, C. M.; Ruiz-García, J. Electrophoretic Mobilities of a Viral Capsid, Its Capsid Protein, and Their Relation to Viral Assembly. *J. Phys. Chem. B* 2014, 118, 1984-1989.

(62) Ermolina, I.; Morgan, H.; Green, N. G.; Milner, J. J.; Feldman, Y. Dielectric Spectroscopy of Tobacco Mosaic Virus. *Biochim. Biophys. Acta*-Gen. Subj. 2003, 1622, 57-63.

(63) Bonezzi, J.; Boika, A. Deciphering the Magnitude of Current Steps in Electrochemical Blocking Collision Experiments and Its Implications. *Electrochim. Acta* 2017, 236, 252-259.

(64) Goldsmith, C. S.; Tatti, K. M.; Ksiazek, T. G.; Rollin, P. E.; Comer, J. A.; Lee, W. W.; Rota, P. A.; Bankamp, B.; Bellini, W. J.; Zaki, S. R. Ultrastructural Characterization of SARS Coronavirus. *Emerg. Infect. Dis.* 2004, 10, 320-326.

(65) Menter, T.; Haslbauer, J. D.; Nienhold, R., Savic, S.; Hopfer, H.; Deigendesch, N.; Frank, S.; Turek, D.; Willi, N.; Pargger, H.; Bassetti, S.; Leuppi, J. D.; Cathomas, G.; Tolnay, M.; Mertz, K. D.; Tzankov, A. Postmortem Examination of COVID-19 Patients Reveals Diffuse Alveolar Damage with Severe Capillary Congestion and Variegated Findings in Lungs and Other Organs Suggesting Vascular Dysfunction. *Histopathology* 2020, 77, 198-209.

(66) Shich, W. J.; Hsiao, C. H.; Paddock, C. D.; Guarner, J., Goldsmith, C. S.; Tatti, K.; Packard, M.; Mueller, L.; Wu, M. Z.; Rollin, P.; Su, I. J.; Zaki, S. R. Immunohistochemical, in Situ Hybridization, and Ultrastructural Localization of SARS-Associated Coronavirus in Lung of a Fatal Case of Severe Acute Respiratory Syndrome in Taiwan. *Hum. Pathol.* 2005, 36, 303-309.

(67) Zhu, N.; Zhang, D.; Wang, W.; Li, X.; Yang, B.; Song, J.; Zhao, X.; Huang, B.; Shi, W., Lu, R.; Niu, P.; Zhan, F.; Ma, X.; Wang, D.; Xu, W.; Wu, G.; Gao, G. F.; Tan, W. A Novel Coronavirus from Patients with Pneumonia in China, 2019. *N. Engl. J. Med.* 2020, 382, 727-733.

(68) Grom, F.; Kentsch, J.; Müller, T.; Schnelle, T.; Stelzle, M. Accumulaion and Trapping of Hepatitis A Virus Particles by Electrohydrodynamic Flow and Dielectrophoresis. *Electrophoresis* 2006, 27, 1386-1393.

(69) Sepunaru, L.; Plowman, B. J.; Sokolov, S. V.; Young, N. P.; Compton, R. G. Rapid Electrochemical Detection of Single Influenza Viruses Tagged with Silver Nanoparticles. *Chem. Sci.* 2016, 7, 3892-3899.

(70) Salm, E.; Guevara, C. D.; Dak, P.; Dorvel, B. R.; Reddy, B.; Alam, M. A.; Bashir, R. Ultralocalized Thermal Reactions in Subnanoliter Droplets-in-Air. *Proc. Natl. Acad. Sci. U.S.A.* 2013, 110, 3310-3315.

(71) Ebrahimi, A.; Dak, P.; Salm, E.; Dash, S.; Garimella, S. V.; Bashir, R.; Alam, M. A. Nanotextured Superhydrophobic Electrodes Enable Detection of Attomolar-Scale DNA Concentration within a Droplet by Non-Faradaic Impedance *Spectroscopy. Lab Chip* 2013, 13, 4248-4256.

(72) Gregoritza, M.; Brandl, F. P. The Diels-Alder Reaction: A Powerful Tool for the Design of Drug Delivery Systems and Biomaterials. *Eur. J. Pharm. Biopharm.* 2015, 97, 438-453.

(73) Ermolina, I.; Milner, J.; Morgan, H. Dielectrophoretic Investigation of Plant Virus Particles: Cow Pea Mosaic Virus and Tobacco Mosaic Virus. *Electrophoresis* 2006, 27, 3939-3948.

(74) Vega-Acosta, J. R.; Cadena-Nava, R. D.; Gelbart, W. M.; Knobler, C. M.; Ruiz-García, J. Electrophoretic Mobilities of a Viral Capsid, Its Capsid Protein, and Their Relation to Viral Assembly. *J. Phys. Chem. B* 2014, 118, 1984-1989.

(75) Ermolina, I.; Morgan, H.; Green, N. G., Milner, J. J.; Feldman, Y. Dielectric Spectroscopy of Tobacco Mosaic Virus. *Biochim. Biophys. Acta*-Gen. Subj. 2003, 1622, 57-63.

It should be understood that the disclosure of a range of values is a disclosure of every numerical value within that range, including the end points. It should also be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be apparent to those skilled in the art that numerous modifications and variations of the described examples and embodiments are possible considering the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof.

It should be understood that modifications to the embodiments disclosed herein can be made to meet a particular set of design criteria. Therefore, while certain exemplary embodiments of the apparatuses and methods of using and making the same disclosed herein have been discussed and illustrated, it is to be distinctly understood that the invention is not limited thereto but may be otherwise variously embodied and practiced within the scope of the following claims.

What is claimed is:

1. A redox cycling electrochemical system, comprising:
a first working electrode having a cross-section, the first working electrode being a generator electrode;
a second working electrode having a cross-section, the second working electrode being a collector electrode; and electrolyte;
wherein:
each of the cross-sections of the first working electrode and the second working electrode includes a pillar and a particle capture region, the particle capture region being a portion configured to attract a particle supported within the electrolyte;
for each of the first working electrode and the second working electrode, the pillar and the particle capture region are electrically the same conductor; and
each of the cross-sections of the first working electrode and the second working electrode exhibits an undercut formation at an interface between the pillar and the particle capture region, resulting in a gap between the particle capture region of the first working electrode and the particle capture region of the second working electrode that is less than a gap between the pillar of the first working electrode and the pillar of the second working electrode;
wherein the particle capture region of the second working electrode is part of an annular member;
wherein the second working electrode surrounds the first working electrode in a concentric manner;
wherein the pillar of the first working electrode extends from a generator electrode base, the pillar being an elongate member, and the particle capture region being located at a distal end of the pillar; and
the pillar of the second working electrode extends from a collector electrode base, the pillar being an elongate member, and the particle capture region being located at a distal end of the pillar.

2. The electrochemical system of claim 1, wherein:
the electrochemical system is a component of a biosensor;
each of the particle capture region of the first working electrode and the particle capture region of the second working electrode is a virion capture region.

3. The electrochemical system of claim 1, wherein:
each of the pillar of the first working electrode and the second working electrode is an elongate member; and
the particle capture region of the first working electrode is located at a distal end of the pillar of the first working electrode, and the particle capture region of the second working electrode is located at a distal end of the pillar of the second working electrode.

4. The electrochemical system of claim 1, wherein:
the cross-section of the particle capture region of the first working electrode is a square shape or a trapezoid shape; and
the cross-section of the particle capture region of the second working electrode is a square shape of a trapezoid shape.

5. The electrochemical system of claim 1, wherein:
for each of the first working electrode and the second working electrode, a combination of the pillar with the particle capture region exhibits a mushroom shape cross-section.

6. The electrochemical system of claim 1, wherein:
the second working electrode at least partially surrounds the first working electrode.

7. The electrochemical system of claim 1, wherein:
the particle capture region of the first working electrode does not make physical contact with the second working electrode; and
the particle capture region of the second working electrode does not make physical contact with the first working electrode.

8. The electrochemical system of claim 1, wherein:

the first working electrode includes plural pillars; and the second working electrode includes plural pillars.

\* \* \* \* \*